(12) United States Patent
Muraca

(10) Patent No.: US 7,897,354 B2
(45) Date of Patent: Mar. 1, 2011

(54) KINASE PEPTIDES AND ANTIBODIES

(75) Inventor: Patrick J. Muraca, Pittsfield, MA (US)

(73) Assignee: Nuclea Biotechnologies, Inc., Pittsfield, MA (US)

( * ) Notice: Subject to any disclaimer, the term of this patent is extended or adjusted under 35 U.S.C. 154(b) by 0 days.

(21) Appl. No.: 12/080,868

(22) Filed: Apr. 7, 2008

(65) Prior Publication Data

US 2009/0111124 A1 Apr. 30, 2009

Related U.S. Application Data

(63) Continuation-in-part of application No. 11/435,570, filed on May 17, 2006, now Pat. No. 7,354,725.

(60) Provisional application No. 60/682,115, filed on May 18, 2005.

(51) Int. Cl.
*G01N 33/53* (2006.01)
(52) U.S. Cl. .......................... 435/7.1; 435/7.2; 436/518
(58) Field of Classification Search ........................ None
See application file for complete search history.

(56) References Cited

U.S. PATENT DOCUMENTS

| 6,001,580 | A | 12/1999 | Tani et al. ................. 435/7.1 |
| 6,133,032 | A * | 10/2000 | Monia et al. ............... 435/375 |
| 6,258,776 | B1 | 7/2001 | Hemmings et al. .............. 514/2 |
| 6,582,927 | B2 * | 6/2003 | Aronheim .................... 435/7.2 |
| 7,108,992 | B2 | 9/2006 | Kastan et al. ................. 435/7.4 |
| 7,595,154 | B2 | 9/2009 | Heinrich et al. | |

2004/0014095 A1 *  1/2004  Gerber et al. ................. 435/6

FOREIGN PATENT DOCUMENTS

| WO | WO 01/27315 | 4/2001 |
| WO | WO 02/083933 | 10/2002 |
| WO | WO 03/087400 | 10/2003 |
| WO | WO 2004/038040 | 5/2004 |

OTHER PUBLICATIONS

Campbell (Monoclonal Antibody Technology 1984, Elsevier Science Publisher; Section 1.3.4, p. 29).*
Clifton, et al., "A comparison of the substrate specificity of MAKAP kinase-2 and MAPKAP kinase-3 and their activation by cytokines and cellular stress"; FEBS Letts.; (1996); 392: 209-214.
Leighton, et al., "Comparison of the specificiies of p. 70 S6 kinase and MAPKAP kinase-1 identifies a relatively specific substrate for p. 70 S6 kinase: the N-terminal kinase domain of MAPKAP kinase-1 is essential for peptide phosphorylation"; FEBS Letts.; (1995); 375: 289-293.
Stokoe, et al.; "The Substrate specificity and structure of mitogen-activated protein (MAP) kinase-activated protein kinase-2"; Biochem. J.; (1993); 296: 843-849.
Wadsworth, et al., "RWJ 67657, a Potent, Orally Active Inhibitor of p. 38 Mitogen-Activated Protein Kinase"; J. Pharmacol & Experimental Therapeutics; (1999); 291: 680-687.
Kim et al., Biochem. Biophys. Res. Comm., vol. 310(2), pp. 542-549 (2003).
Heinrich et al., Science, vol. 299(5607), pp. 708-710 (2003).

* cited by examiner

*Primary Examiner*—Jacob Cheu
(74) *Attorney, Agent, or Firm*—Paula C. Evans

(57) ABSTRACT

The invention relates to novel kinase peptides and antibodies, as well as nucleic acids related to them. The peptides, antibodies and the nucleic acids are useful for the detection, staging and monitoring of the progression of a kinase-mediated disease, as well as for determining or monitoring the efficacy of treatment.

2 Claims, 21 Drawing Sheets

KINASE PEPTIDES AND ANTIBODIES

RELATED APPLICATIONS

This application is a continuation-in-part of Ser. No. 11/435,570 filed 17 May 2006, which claims priority under 35 U.S.C. §119(e) to U.S. Provisional Application Ser. No. 60/682,115 filed May 18, 2005, the entirety of which are incorporated herein by reference.

FIELD OF INVENTION

The invention relates to kinase peptides and antibodies having immunospecificity for kinase polypeptides and proteins, as well as nucleic acids related to these peptides and antibodies, and methods for using the peptides and antibodies.

BACKGROUND OF THE INVENTION

Protein kinases are enzymes that covalently modify proteins by attaching phosphate groups (from ATP) to serine, threonine, and/or tyrosine residues. In so doing, the functional properties of the protein kinase's substrates are modified. Protein kinases transduce signals from the cell membrane into the interior of the cell. Such signals include not only those arising from ligand-receptor interactions but also environmental perturbations when the membrane undergoes mechanical deformation (i.e., cell stretch or shear stress). Ultimately, the activation of signaling pathways that use protein kinases often culminate in the reprogramming of gene expression through the direct regulation of transcription factors or through the regulation of mRNA stability or protein translation. Protein kinases regulate most aspects of normal cellular function.

Many signal transduction pathways involved in the control of cell proliferation and differentiation originate with transmembrane receptors containing cytoplasmic protein kinase domains. For instance, there are many kinds of cytokine and growth factor receptors that belong to different receptor families. Most of these receptors function as: (1) receptor tyrosine kinase and tyrosine-kinase-associated receptor (see, for example, Fanti et al. (1993) Annu. Rev. Biochem, 62:453); (2) receptors serine/threonine kinase (for example, Josso and di Clemente, (1997) Curr Opin Genet Dev., 7:371-7; Dijke et al. (1996), Curr Opin Cell Biol., 8(2):139-45); or (3) G-protein linked receptors (Piper and Zeuzem (2004) Curr Pharm Des., 10(28):3539-45; Presland (2004) Biochem Soc Trans., 32(Pt 5):888-91). Following binding with an extracellular ligand and activation, the receptors trigger different cascade of intracellular protein phosphorylation to transduction signals, thereby altering the cell's pattern of gene expression and leading to biological effects.

The pathophysiological dysfunction of protein kinase signaling pathways underlies the molecular basis of many cancers and of several manifestations of cardiovascular disease, such as hypertrophy and other types of left ventricular remodeling, ischemia/reperfusion injury, angiogenesis, and atherogenesis. Because of the important roles the protein kinases play, they have emerged as crucial targets for a variety of diagnostic and therapeutic indications, including, cancer, inflammatory disorders, autoimmune diseases (e.g., diabetes), cardiovascular diseases, and neurological disorders.

SUMMARY OF THE INVENTION

The present invention provides kinase peptides, antibodies, and related nucleic acids. The present invention also provides diagnostic and therapeutic compositions and methods using these peptides, antibodies and nucleic acids.

The present invention provides an isolated and/or recombinant kinase peptide comprising an amino acid sequence selected from the group consisting of: SEQ ID NOs. 1-23.

In one embodiment, a mixture comprising two or more isolated and/or recombinant kinase peptides is provided.

The invention further provides an antibody specifically immunoreactive with one or more kinase peptides comprising an amino acid sequence selected from the group consisting of: SEQ ID NOs. 1-23.

In one embodiment, a mixture comprising two or more antibodies is provided.

The present invention provides an isolated nucleic acid comprising a sequence encoding a peptide selected from the group consisting of SEQ ID NOs. 1-23, or a complementary nucleotide sequence.]

In one embodiment, a mixture comprising two or more nucleic acids is provided.

The kinase peptide, antibody, or nucleic acid of the invention may further comprise a detectable label. The kinase peptide, antibody, or nucleic acid of the invention may be immobilized on a substrate.

The present invention also provides an expression vector comprising a nucleic acid which comprises a sequence encoding a peptide selected from the group consisting of: SEQ ID NOs. 1-23, or a complementary nucleotide sequence. The present invention further provides a host cell transfected with the expression vector.

The present invention provides a composition for detecting kinase polypeptides or proteins in a sample, comprising a primary antibody specifically immunoreactive with one or more kinase peptides comprising an amino acid sequence selected from the group consisting of SEQ ID NOs. 1-23. The primary antibody may be labeled with a detectable label.

The composition of the invention may further comprise a secondary antibody. In one embodiment, the secondary antibody reacts with the primary antibody. In another embodiment, the secondary antibody is specifically immunoreactive with one or more kinase peptides comprising an amino acid sequence selected from the group consisting of SEQ ID NOs. 1-23. The secondary antibody may be labeled with a detectable label.

The present invention provides a composition for detecting one or more kinase polypeptides or proteins in a sample, comprising a nucleic acid which comprises at least a portion of a sequence encoding a peptide selected from the group consisting of: SEQ ID NOs. 1-23, or a complementary nucleotide sequence. The nucleic acid preferably comprises at least about 5 up to about 30 nucleic acid bases encoding a portion of a peptide selected from the group consisting of: SEQ ID NOs. 1-23, or a complementary nucleotide sequence.

The nucleic acid may be labeled with a detectable label.

The present invention provides a method for detecting, diagnosing, staging or monitoring the progression of a kinase-mediated disease in a subject, the method comprising the steps of a) providing a sample from the subject, b) detecting a level of a kinase polypeptide or protein in the sample using an antibody specifically immunoreactive with a kinase peptide comprising an amino acid sequence selected from the group consisting of SEQ ID NOs. 1-23; and c) comparing the level(s) of the kinase polypeptide(s) in the sample to a baseline level of the kinase polypeptide(s); where a difference in level(s) of the kinase polypeptide(s) is indicative of the presence, stage or progression of the disease in the subject.

The step of detecting or monitoring is may be accomplished by a method selected from the group consisting of immunoblot, enzyme-linked immunosorbant assay (ELISA), radioimmunoassay (RIA), immunoprecipitation, immunohistochemistry and immunofluorescence.

The present invention provides a method for detecting, diagnosing, staging or monitoring the progression of a kinase-mediated disease in a subject, the method comprising the steps of: a) providing a sample from the subject, b) detecting a level of a kinase nucleic acid in the sample using a nucleic acid which comprises a sequence encoding a peptide selected from the group consisting of: SEQ ID NOs. 1-23, or a complementary nucleotide sequence; and c) comparing the level of the kinase nucleic acid in the sample to a baseline level of the kinase nucleic acid; where a difference in level of the kinase nucleic acid is indicative of the presence, stage or progression of the disease in the subject.

The kinase nucleic acid may be a DNA or an RNA.

The step of detecting or monitoring is may be accomplished by a method selected from the group consisting of polymerase chain reaction (PCR), reverse transcriptase-PCR (RT-PCR), in situ hybridization, Southern blot, Northern blot, sequence analysis, gene microarray analysis, and detection of a reporter gene.

In one aspect, the method of the invention further comprises determining the efficacy of therapeutic intervention or treatment by a step of (d) modifying therapeutic intervention or treatment of the disease based on the difference in kinase level(s) as indicated in step (c).

In one embodiment, the sample is obtained from a patient to be diagnosed monitored or treated for the disease, and the baseline level is from a control sample from a patient not having the disease.

In another embodiment, the sample is from a patient who is known to have the disease, and the baseline level comprises a level of kinase from a previous disease sample from the same patient, wherein a difference in the level of the kinase indicates that the patient is at a different disease stage, or is indicative of the efficacy of therapeutic intervention or treatment, e.g, the responsiveness of the patient to therapy.

The sample of the invention may comprise, for example, a bodily fluid sample, a tissue sample, or a cell sample. The sample may be immobilized on a substrate.

In one embodiment, the method of the invention is used to determine the prognosis of the disease in a patient. In another embodiment, the method of the invention is used to determine the susceptibility of a patient to a therapeutic treatment.

BRIEF DESCRIPTION OF DRAWINGS

FIG. 8b shows the results at a later date using reduced samples, and FIG. 8c shows the results at a later date using non-reduced samples.

FIGS. 10 a-c are graphs showing the accuracy, specificity and sensitivity of the anti-MAPKAP antibodies raised against SEQ ID NOs. 7-11.

FIGS. 11 a-c are graphs showing the accuracy, specificity and sensitivity of the anti-PI3 antibodies raised against SEQ ID NOs. 12-19.

In FIG. 12a, Lane 1 is a reference ladder; Lane 2 shows the results for SEQ ID NO. 12; Lane 3, shows the results for SEQ ID NO. 13; Lane 4 shows the results for SEQ ID NO. 14; Lane 5 shows the results for SEQ ID NO. 15; Lane 6 shows the results for SEQ ID NO. 16; Lane 7 shows the results for SEQ ID NO. 17; Lane 8 shows the results for SEQ ID NO. 18; Lane 9 shows the results for SEQ ID NO. 19; and Lane 10 shows the results for a commercial anti-MAPK antibody used as a control. In FIG. 12b, Lane 1 is a reference ladder; Lane 2 shows the results for SEQ ID NO. 20; Lane 3, shows the results for SEQ ID NO. 21; Lane 4 shows the results for SEQ ID NO. 22; Lane 5 shows the results for SEQ ID NO. 23; Lane 6 shows the results for SEQ ID NO. 17; Lane 7 shows the results for SEQ ID NO. 18; Lane 8 shows the results for SEQ ID NO. 15; Lane 9 shows the results for SEQ ID NO. 19; and Lane 10 shows the results for a commercial anti-MAPK antibody used as a control.

DETAILED DESCRIPTION OF THE INVENTION

Figure 1:
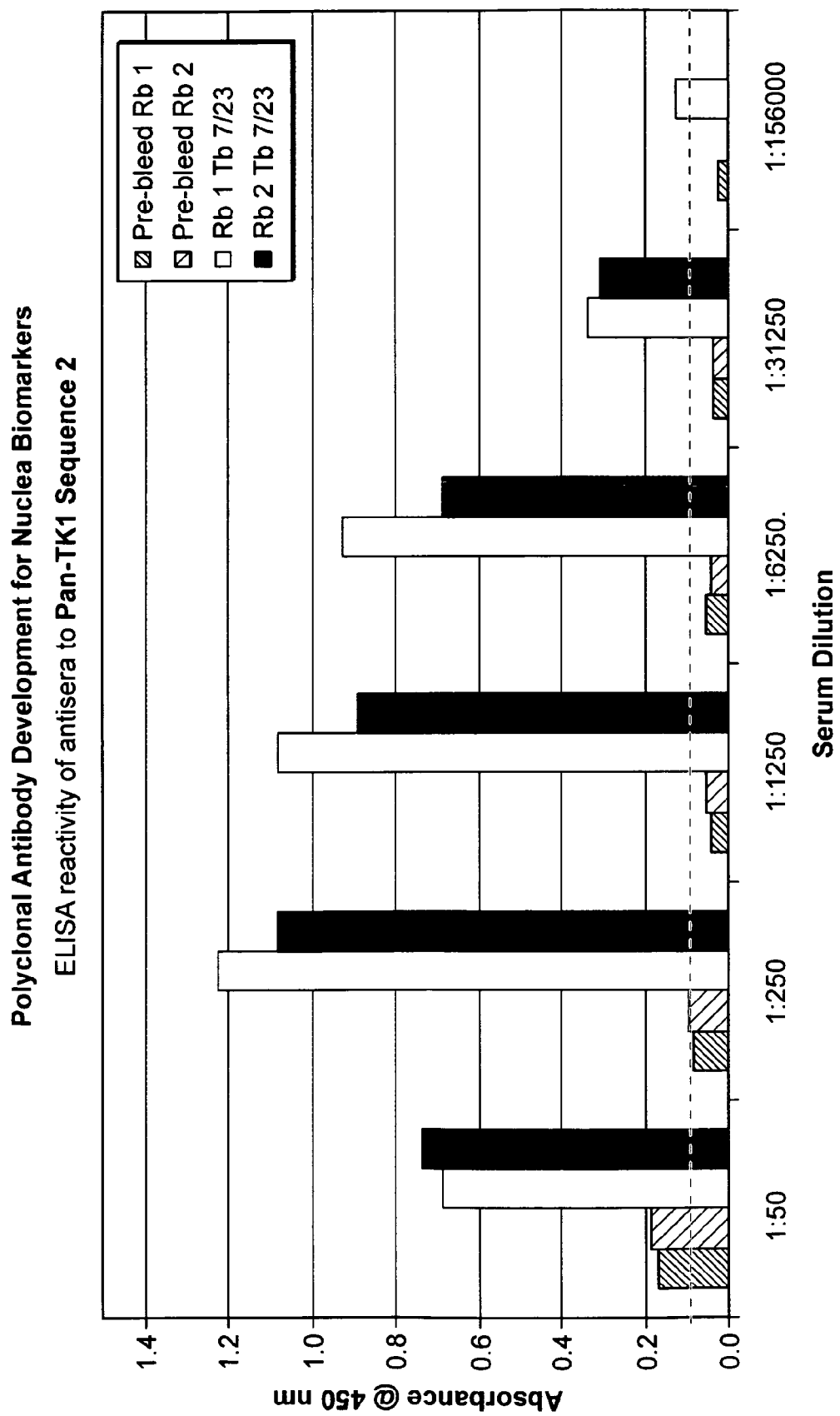
FIG. 1 is a graph showing the ELISA reactivity of polyclonal antisera pan-TK1 to kinase peptide sequence 2 (SEQ ID NO. 1) before and after incubation.

The present invention provides novel kinase peptides, and antibodies specifically immunoreactive to these kinase peptides. Also provided are nucleic acids encoding the peptides and antibodies of the invention, as well as probes/primers which hybridize to kinase peptides or proteins. The peptides, antibodies, and nucleic acids may be used in researching kinase-related biological activities, e.g., signal transduction, as well as in disease diagnosis, monitoring, prognosis and therapy.

Protein Kinases

Different kinases phosphorylate different amino acid residues, and they may play different yet overlapping roles. There are over 500 protein kinases encoded in the human genome. For example, tyrosine protein kinases in general respond to growth factors or mitogenic signals and phosphorylate proteins that initiate rapid signal transduction. Serine/threonine protein kinases typically phosphorylate proteins that integrate and amplify intracellular signals, leading in some cases to regulation of certain transcription factors and expression of genes. Many kinases have been implicated as playing a role in diseases, including cancer and other inflammatory diseases, autoimmune diseases (e.g., diabetes), cardiovascular diseases and neurological disorders. (Chapter 2 and Tables 1-6 in Kinases: From Targets to Therapeutics, CHA Advances Reports, July 2003, hereby incorporated by reference in its entirety). A disease or disorder in which a kinase is implicated is referred to herein as a "kinase-mediated disease."

Useful kinases of the present invention include both receptor and nonreceptor kinases. The kinases serve as the targets for research, diagnostic or therapeutic application of the present invention. Tables 1-4 list some nonlimiting examples. * in Tables 1-4 refers to the OMIM™. (Online Mendelian Inheritance in Man™) Accession Number.

TABLE 1

Examples of Useful Kinases--Tyrosine Protein Kinases

*191315 NEUROTROPHIC TYROSINE KINASE, RECEPTOR, TYPE 1; NTRK1
*600758 PROTEIN-TYROSINE KINASE, CYTOPLASMIC; PTK2
*176947 SYK-RELATED TYROSINE KINASE; SRK
*600038 PROTEIN TYROSINE KINASE CTK; CTK
*600341 TYRO3 PROTEIN TYROSINE KINASE; TYRO3
*300300 BRUTON AGAMMAGLOBULINEMIA TYROSINE KINASE; BTK
*151520 LEUKOCYTE TYROSINE KINASE; LTK
*600085 PROTEIN-TYROSINE KINASE SYK; SYK
601951 PROTEIN-TYROSINE KINASE STY
*600221 TEK TYROSINE KINASE, ENDOTHELIAL; TEK
*176946 ELK-RELATED TYROSINE KINASE; ERK
*600222 TYROSINE KINASE WITH IMMUNOGLOBULIN AND EGF FACTOR HOMOLOGY DOMAINS; TIE
*176944 PROTEIN TYROSINE KINASE TKF
*191316 NEUROTROPHIC TYROSINE KINASE, RECEPTOR, TYPE 3; NTRK3
*600050 MIXED-LINEAGE PROTEIN KINASE-3; MLK3
*176949 PROTEIN KINASE, MITOGEN-ACTIVATED 4; PRKM4
*176948 PROTEIN KINASE, MITOGEN-ACTIVATED 1; PRKM1
*601890 PROTEIN TYROSINE KINASE PTK7; PTK7
*176945 PROTEIN TYROSINE KINASE EEK
*600855 MINIBRAIN (DROSOPHILA) HOMOLOG; MNBH
*600612 BONE MARROW KINASE, X-LINKED; BMX
*179611 EPH-LIKE TYROSINE KINASE 1; ETK1
*600168 MACROPHAGE STIMULATING 1 RECEPTOR; MST1R
*601679 BTK-ASSOCIATED PROTEIN, 135 KD
*153390 LYMPHOCYTE-SPECIFIC PROTEIN TYROSINE KINASE; LCK
*176943 FIBROBLAST GROWTH FACTOR RECEPTOR-2; FGFR2
*176942 PROTEIN TYROSINE KINASE-3; TYK3; FER
*600058 PROTEIN TYROSINE KINASE TXK; TXK
*600583 TEC PROTEIN TYROSINE KINASE; TEC
*176941 PROTEIN TYROSINE KINASE-2; TYK2
*191164 EPH-RELATED RECEPTOR TYROSINE KINASE LIGAND 1; EPLG1
*186973 T-CELL TYROSINE KINASE EMT; EMT
*179610 EPH TYROSINE KINASE 1; EPHT1
*601050 ZONA PELLUCIDA RECEPTOR TYROSINE KINASE, 95 KD; ZRK
*176872 PROTEIN KINASE, MITOGEN-ACTIVATED,

TABLE 1-continued

Examples of Useful Kinases--Tyrosine Protein Kinases

KINASE 1; PRKMK1
*600997 EPH TYROSINE KINASE 3; EPHT3
*600441 GROWTH ARREST-SPECIFIC GENE-6; GAS6
*191306 KINASE INSERT DOMAIN RECEPTOR; KDR
*109135 AXL RECEPTOR TYROSINE KINASE; AXL
*136350 FIBROBLAST GROWTH FACTOR RECEPTOR-1; FGFR1
*164870 V-ERB-B2 AVIAN ERYTHROBLASTIC LEUKEMIA VIRAL ONCOGENE HOMOLOG 2; ERBB2
*136351 FMS-LIKE TYROSINE KINASE-3; FLT3
*600408 NEUROEPITHELIAL TYROSINE KINASE; NEP
*191311 NEUROTROPHIC TYROSINE KINASE RECEPTOR-RELATED 3; NTRKR3
*600527 EPH-RELATED RECEPTOR TYROSINE KINASE LIGAND 5; EPLG5
*600456 NEUROTROPHIC TYROSINE KINASE, RECEPTOR, TYPE 2; NTRK2
*600524 RYK RECEPTOR-LIKE TYROSINE KINASE
*191305 TYROSINE KINASE, B-LYMPHOCYTE SPECIFIC; BLK
*600600 EPH TYROSINE KINASE 2; EPHT2
*300035 EPH-RELATED RECEPTOR TYROSINE KINASE LIGAND 2; EPLG2
*306000 GLYCOGEN STORAGE DISEASE VIII
*601535 EPH-RELATED RECEPTOR TYROSINE KINASE LIGAND 7; EPLG7
*147795 JANUS KINASE 1; JAK1
*165070 FMS-RELATED TYROSINE KINASE-1; FLT1
*188830 PROTEIN KINASE, cAMP-DEPENDENT, REGULATORY, TYPE I, ALPHA; PRKAR1A
*193525 WEE-1 TYROSINE KINASE; WEE1
*601839 EPH-LIKE TYROSINE KINASE 2; ETK2
*601296 RECEPTOR TYROSINE KINASE MuSK
*147670 INSULIN RECEPTOR; INSR
*600173 JANUS KINASE 3 JAK3
*600007 FMS-RELATED TYROSINE KINASE-3 LIGAND
*176970 PROTEIN KINASE C, BETA 1; PRKCB1
*191309 TYROSINE KINASE-TYPE CELL SURFACE RECEPTOR HER3; HER3
*147796 JANUS KINASE 2; JAK2
*601329 LIM DOMAIN KINASE 1; LIMK1
*600714 DUAL SPECIFICITY PHOSPHATASE 1; DUSP1
*310200 MUSCULAR DYSTROPHY, PSEUDOHYPERTROPHIC PROGRESSIVE, DUCHENNE AND BECKER TYPES; DMD
*142370 HEMOPOIETIC CELL KINASE; HCK
*113508 TYROSINE 3-MONOOXYGENASE/TRYPTOPHAN 5-MONOOXYGENASE ACTIVATION PROTEIN, ETA POLYPEPTIDE; YWHAH
*164761 RET PROTO-ONCOGENE; RET
*601288 TYROSINE 3-MONOOXYGENASE/TRYPTOPHAN 5-MONOOXYGENASE ACTIVATION PROTEIN, ZETA POLYPEPTIDE; YWHAZ
*601289 TYROSINE 3-MONOOXYGENASE/TRYPTOPHAN 5-MONOOXYGENASE ACTIVATION PROTEIN, BETA POLYPEPTIDE; YWHAB
*600011 HEPATOMA TRANSMEMBRANE KINASE; HTK
*601254 MAP KINASE KINASE 6
*171834 PHOSPHATIDYLINOSITOL 3-KINASE, CATALYTIC, ALPHA POLYPEPTIDE; PIK3CA
*123832 CYCLIN-DEPENDENT KINASE INHIBITOR 3; CDKN3
*601826 DIACYLGLYCEROL KINASE, DELTA, 130 KD
*600267 PROTEIN-TYROSINE PHOSPHATASE, NONRECEPTOR TYPE, 13; PTPN13
*189980 ABELSON MURINE LEUKEMIA VIRAL ONCOGENE HOMOLOG 1; ABL1
*125855 DIACYLGLYCEROL KINASE, ALPHA; DAGK1
*601212 FOCAL ADHESION KINASE 2
*600452 EPITHELIAL DISCOIDIN DOMAIN RECEPTOR 1; EDDR1
*105590 ANAPLASTIC LYMPHOMA KINASE; ALK
*601232 PHOSPHATIDYLINOSITOL 3-KINASE, CATALYTIC, GAMMA POLYPEPTIDE; PIK3CG
*171833 PHOSPHATIDYLINOSITOL 3-KINASE REGULATORY SUBUNIT; PIK3R1
*600004 EPH HOMOLOGY KINASE-1; EHK1
*164920 V-KIT HARDY-ZUCKERMAN 4 FELINE SARCOMA VIRAL ONCOGENE HOMOLOG; KIT
*134934 FIBROBLAST GROWTH FACTOR RECEPTOR-3; FGFR3
*601528 VASCULAR ENDOTHELIAL GROWTH FACTOR C; VEGFC
*142408 MACROPHAGE STIMULATING 1; MST1

TABLE 1-continued

Examples of Useful Kinases--Tyrosine Protein Kinases

*143890 HYPERCHOLESTEROLEMIA, FAMILIAL; FHC
*131550 EPIDERMAL GROWTH FACTOR RECEPTOR; EGFR
*114085 S100 CALCIUM-BINDING PROTEIN A10; S100A10
*162200 NEUROFIBROMATOSIS, TYPE I; NF1
164970 ONCOGENE TRK
*151410 LEUKEMIA, CHRONIC MYELOID; CML
*601522 GROWTH FACTOR RECEPTOR-BOUND PROTEIN-7; GRB7
*114210 S100 CALCIUM-BINDING PROTEIN A4; S 100A4
*601589 RAS p21 PROTEIN ACTIVATOR; RASA2
*175100 ADENOMATOUS POLYPOSIS OF THE COLON; APC
*164860 MET PROTO-ONCOGENE; MET
*102582 SIGNAL TRANSDUCER AND ACTIVATOR OF TRANSCRIPTION 3; STAT3
*601836 smg GDS-ASSOCIATED PROTEIN
*601530 UBIQUITIN-BINDING PROTEIN P62
*601603 LYMPHOCYTE CYTOSOLIC PROTEIN 2; LCP2
*600051 EPIDERMAL GROWTH FACTOR RECEPTOR PATHWAY SUBSTRATE-15; EPS15
*601523 GROWTH FACTOR RECEPTOR-BOUND PROTEIN-10; GRB10
*601496 GLIAL CELL LINE-DERIVED NEUROTROPHIC FACTOR RECEPTOR-ALPHA; GDNFRA
*600560 SHC TRANSFORMING PROTEIN; SHC1
*219700 CYSTIC FIBROSIS; CF
*191030 TROPOMYOSIN 3; TPM3
*116940 CELL DIVISION CYCLE 2, G1 TO S AND G2 TO M; CDC2
*253700 MUSCULAR DYSTROPHY, LIMB GIRDLE, TYPE 2C; LGMD2C
*108355 ASH PROTEIN
*272800 TAY-SACHS DISEASE; TSD
*103320 AGRIN; AGRN
*114110 S100 CALCIUM-BINDING PROTEIN A6; S100A6
202700 AGRANULOCYTOSIS, INFANTILE GENETIC
*601893 TRIPLE FUNCTIONAL DOMAIN; TRIO
*308000 HYPOXANTHINE GUANINE PHOSPHORIBOSYLTRANSFERASE 1; HPRT1
*123900 CYTOVILLIN
*600753 GOLGI APPARATUS PROTEIN 1; GLG1
*601524 GROWTH FACTOR RECEPTOR-BOUND PROTEIN-14; GRB14
*190030 V-FES FELINE SARCOMA VIRAL/V-FPS FUJINAMI AVIAN SARCOMA VIRAL ONCOGENE HOMOLOG; FES
*189940 TRANSLOCATED PROMOTER REGION
601269 P32 SPLICING FACTOR SF2 ASSOCIATED PROTEIN
*601146 CARTILAGE-DERIVED MORPHOGENETIC PROTEIN 1
*167414 PAIRED BOX HOMEOTIC GENE 5; PAX5
*147545 INSULIN RECEPTOR SUBSTRATE 1; IRS1
*601247 SON OF SEVENLESS (DROSOPHILA) HOMOLOG 2; SOS2
*311770 PHOSPHATIDYLINOSITOL GLYCAN CLASS A; PIGA
*308100 ICHTHYOSIS, X-LINKED
*180380 RHODOPSIN; RHO
*600802 SEVERE COMBINED IMMUNODEFICIENCY DISEASE, AUTOSOMAL RECESSIVE, T-NEGATIVE/B-POSITIVE TYPE
*165360 CAS-BR-M (MURINE) ECOTROPIC RETROVIRAL TRANSFORMING SEQUENCE; CBL
*190182 TRANSFORMING GROWTH FACTOR-BETA RECEPTOR, TYPE II; TGFBR2
*164770 COLONY-STIMULATING FACTOR-1 RECEPTOR; CSF1R
*173335 PHOSPHODIESTERASE I/NUCLEOTIDE PYROPHOSPHATASE 1; PDNP1
*164040 NUCLEOPHOSMIN; NPM1
*102680 ADDUCIN 1; ADD1
*162300 NEUROMATA, MUCOSAL, WITH ENDOCRINE TUMORS
*600936 HYALURONAN-MEDIATED MOTILITY RECEPTOR; HMMR
*133430 ESTROGEN RECEPTOR; ESR
*601099 SRC-LIKE ADAPTER; SLA
*130650 BECKWITH-WIEDEMANN SYNDROME; BWS
*148500 TYLOSIS WITH ESOPHAGEAL CANCER; TOC
*601121 PLACENTAL GROWTH FACTOR; PGF
*600618 ETS VARIANT GENE 6; ETV6
*155960 MEMBRANE COMPONENT, CHROMOSOME 6, POLYPEPTIDE 2; M6P2
*147780 INTERLEUKIN-4; IL4
*164940 GARDNER-RASHEED FELINE SARCOMA VIRAL (V-FGR) ONCOGENE; FGR
*600483 FIBROBLAST GROWTH FACTOR-8; FGF8
*601272 SORTING NEXIN-1; SNX1

TABLE 1-continued

Examples of Useful Kinases--Tyrosine Protein Kinases

*142410 TRANSCRIPTION FACTOR 1, HEPATIC; TCF1
*142409 HEPATOCYTE GROWTH FACTOR; HGF
*147880 INTERLEUKIN-6 RECEPTOR; IL6R
*164880 V-YES-I YAMAGUCHI SARCOMA VIRAL ONCOGENE; YES1
*131195 ENDOGLIN; ENG
*187601 THANATOPHORIC DYSPLASIA WITH KLEEBLATTSCHAEDEL
*601306 HEMATOPOIETIC CELL-SPECIFIC LYN SUBSTRATE 1; HCLS1
*189972 GENERAL TRANSCRIPTION FACTOR IIH, POLYPEPTIDE 1; GTF2H1
*190040 V-SIS PLATELET-DERIVED GROWTH FACTOR BETA POLYPEPTIDE; PDGFB
*125850 DIABETES MELLITUS, AUTOSOMAL DOMINANT
*600244 PROGRAMMED CELL DEATH 1; PDCD1
*190181 TRANSFORMING GROWTH FACTOR-BETA RECEPTOR, TYPE I; TGFBR1
*600206 EPIDERMAL GROWTH FACTOR RECEPTOR PATHWAY SUBSTRATE-8; EPS8
*192240 VASCULAR ENDOTHELIAL GROWTH FACTOR; VEGF
*116935 CELL ADHESION REGULATOR; CAR
*205900 ANEMIA, CONGENITAL HYPOPLASTIC, OF BLACKFAN AND DIAMOND
*230800 GAUCHER DISEASE, TYPE I; GD I
*248600 MAPLE SYRUP URINE DISEASE; MSUD
*311030 MCF.2 CELL LINE DERIVED TRANSFORMING SEQUENCE; MCF2
*306400 GRANULOMATOUS DISEASE, CHRONIC; CGD
*601922 ANGIOPOIETIN 2; ANGPT2
*307200 HYPOGAMMAGLOBULINEMIA AND ISOLATED GROWTH HORMONE DEFICIENCY, X-LINKED
*601956 GLIAL CELL LINE-DERIVED NEUROTROPHIC FACTOR RECEPTOR-BETA
*601985 H4 GENE

TABLE 2

Examples of Useful Kinases--Ser/Thr Protein Kinases

*601955 CYCLIN-DEPENDENT KINASE 7; CDK7
*160900 DYSTROPHIA MYOTONICA; DM
*600855 MINIBRAIN (DROSOPHILA) HOMOLOG; MNBH
*179090 RAC SERINE/THREONINE PROTEIN KINASE
*601032 SERINE-THREONINE PROTEIN KINASE N; PKN
*601959 SERINE/THREONINE PROTEIN KINASE 2; STK2
*600899 PROTEIN KINASE, DNA-ACTIVATED, CATALYTIC SUBUNIT; PRKDC
*600447 ZIPPER PROTEIN KINASE; ZPK
*601951 PROTEIN-TYROSINE KINASE STY
*300300 BRUTON AGAMMAGLOBULINEMIA TYROSINE KINASE; BTK
*600765 MKN28 KINASE
*300083 PROTEIN KINASE, X-LINKED; PRKX
*176946 ELK-RELATED TYROSINE KINASE; ERK
*300075 RIBOSOMAL PROTEIN S6 KINASE, 90 KD, POLYPEPTIDE 3; RPS6KA3
*306000 GLYCOGEN STORAGE DISEASE VIII
*600831 DEATH-ASSOCIATED PROTEIN KINASE 1; DAPK1
*311550 PCTAIRE PROTEIN KINASE 1; PCTK1
*176871 PROTEIN KINASE, INTERFERON-INDUCIBLE DOUBLE-STRANDED RNA; PRKR
*601284 ACTIVIN A RECEPTOR, TYPE II-LIKE KINASE 1; ACVRLK1
*601639 PROTEIN KINASE, cAMP-DEPENDENT, CATALYTIC, ALPHA; PRKACA
*400008 PROTEIN KINASE, Y-LINKED; PRKY
*137026 G PROTEIN-COUPLED RECEPTOR KINASE 2 (DROSOPHILA)-LIKE; GPRK2L
*600448 PROTEIN KINASE C, THETA FORM; PRKCQ
*601329 LIM DOMAIN KINASE 1; LIMK1
*311800 PHOSPHOGLYCERATE KINASE 1; PGK1
*601988 LIM DOMAIN KINASE 2; LIMK2
*601158 C-JUN KINASE

TABLE 2-continued

Examples of Useful Kinases--Ser/Thr Protein Kinases

*601298 ACTIVIN A RECEPTOR, TYPE II-LIKE KINASE 2; ACVRLK2
*147795 JANUS KINASE 1; JAK1
*600526 ELKL MOTIF KINASE; EMK1
*154235 MALE GERM CELL-ASSOCIATED KINASE; MAK
*115442 CASEIN KINASE 2, ALPHA-PRIME SUBUNIT; CSNK2A2
*115441 CASEIN KINASE 2, BETA POLYPEPTIDE; CSNK2B
*115440 CASEIN KINASE 2, ALPHA 1 POLYPEPTIDE; CSNK2A1
*151410 LEUKEMIA, CHRONIC MYELOID; CML
*164761 RET PROTO-ONCOGENE; RET
*601983 HEMATOPOIETIC PROGENITOR KINASE 1
*600664 CONSERVED HELIX-LOOP-HELIX UBIQUITOUS KINASE; CHUK
*600864 CASEIN KINASE 1, DELTA; CSNK1D
*600863 CASEIN KINASE 1, EPSILON; CSNK1E
*600954 DEATH-ASSOCIATED PROTEIN; DAP
*164730 V-AKT MURINE THYMOMA VIRAL ONCOGENE HOMOLOG 1; AKT1
*191170 TUMOR PROTEIN p53; TP53
*601792 PROTEIN PHOSPHATASE 1, REGULATORY (INHIBITOR) SUBUNIT 2; PPP1R2
*202500 SEVERE COMBINED IMMUNODEFICIENCY DISEASE-1; SCID1
*238600 HYPERLIPOPROTEINEMIA, TYPE I
*120150 COLLAGEN, TYPE I, ALPHA-1 CHAIN; COL1A1
*601530 UBIQUITIN-BINDING PROTEIN P62
*272800 TAY-SACHS DISEASE; TSD
*219700 CYSTIC FIBROSIS; CF
*601702 p160-ROCK
*601497 BCL2-ASSOCIATED ATHANOGENE 1; BAG1
*308000 HYPOXANTHINE GUANINE PHOSPHORIBOSYL TRANSFERASE 1; HPRT1
*164960 ONCOGENE PIM-1; PIM1; PIM
*601146 CARTILAGE-DERIVED MORPHOGENETIC PROTEIN 1
*230400 GALACTOSEMIA
*233700 GRANULOMATOUS DISEASE, CHRONIC, AUTOSOMAL CYTOCHROME-b-POSITIVE FORM I
*190182 TRANSFORMING GROWTH FACTOR-BETA RECEPTOR, TYPE II; TGFBR2
*180380 RHODOPSIN; RHO
*601366 MOTHERS AGAINST DECAPENTAPLEGIC (*DROSOPHILA*) HOMOLOG 2; MADH2
*601893 TRIPLE FUNCTIONAL DOMAIN; TRIO
*190181 TRANSFORMING GROWTH FACTOR-BETA RECEPTOR, TYPE I; TGFBR1
*189972 GENERAL TRANSCRIPTION FACTOR IIH, POLYPEPTIDE 1; GTF2H1
*600956 ANTI-MULLERIAN HORMONE TYPE II RECEPTOR; AMHR2
*164757 V-RAF MURINE SARCOMA VIRAL ONCOGENE HOMOLOG B1; BRAF
*600799 BONE MORPHOGENETIC RECEPTOR TYPE II; BMPR2
*232600 GLYCOGEN STORAGE DISEASE V
*516050 COMPLEX IV, CYTOCHROME c OXIDASE SUBUNIT III
*311010 V-RAF MURINE SARCOMA 3611 VIRAL ONCOGENE HOMOLOG 1; ARAF1
*230800 GAUCHER DISEASE, TYPE I; GD I
*164710 V-RAF MURINE SARCOMA 3611 VIRAL ONCOGENE HOMOLOG 2; ARAF2
*123835 CYCLIN A; CCNA
*301300 ANEMIA, HYPOCHROMIC; ANH1
*306400 GRANULOMATOUS DISEASE, CHRONIC; CGD
*102576 ACTIVIN A RECEPTOR, TYPE I; ACVR1

TABLE 3

Examples of Useful Kinases--Serine Protein Kinases

*601955 CYCLIN-DEPENDENT KINASE 7; CDK7
*160900 DYSTROPHIA MYOTONICA; DM
*600855 MINIBRAIN (*DROSOPHILA*) HOMOLOG; MNBH
*179090 RAC SERINE/THREONINE PROTEIN KINASE
*601032 SERINE-THREONINE PROTEIN KINASE N; PKN
*601939 PROTEIN KINASE, SERINE/ARGININE-SPECIFIC

TABLE 3-continued

Examples of Useful Kinases--Serine Protein Kinases

*177015 PROTEIN SERINE KINASE H1; PSKH1
*601959 SERINE/THREONINE PROTEIN KINASE 2; STK2
*600899 PROTEIN KINASE, DNA-ACTIVATED, CATALYTIC SUBUNIT; PRKDC
*600447 ZIPPER PROTEIN KINASE; ZPK
*601951 PROTEIN-TYROSINE KINASE STY
*176947 SYK-RELATED TYROSINE KINASE; SRK
*300300 BRUTON AGAMMAGLOBULINEMIA TYROSINE KINASE; BTK
*600765 MKN28 KINASE
*156490 NON-METASTATIC CELLS 1, PROTEIN EXPRESSED IN; NME1
*176946 ELK-RELATED TYROSINE KINASE; ERK
*300083 PROTEIN KINASE, X-LINKED; PRKX
*176943 FIBROBLAST GROWTH FACTOR RECEPTOR-2; FGFR2
*300075 RIBOSOMAL PROTEIN S6 KINASE, 90 KD, POLYPEPTIDE 3; RPS6KA3
*311550 PCTAIRE PROTEIN KINASE 1; PCTK1
*600831 DEATH-ASSOCIATED PROTEIN KINASE 1; DAPK1
*601284 ACTIVIN A RECEPTOR, TYPE II-LIKE KINASE 1; ACVRLK1
*306000 GLYCOGEN STORAGE DISEASE VIII
*176871 PROTEIN KINASE, INTERFERON-INDUCIBLE DOUBLE-STRANDED RNA; PRKR
*400008 PROTEIN KINASE, Y-LINKED; PRKY
*137026 G PROTEIN-COUPLED RECEPTOR KINASE 2 (*DROSOPHILA*)-LIKE; GPRK2L
*601329 LIM DOMAIN KINASE 1; LIMK1
*601639 PROTEIN KINASE, cAMP-DEPENDENT, CATALYTIC, ALPHA; PRKACA
*600448 PROTEIN KINASE C, THETA FORM; PRKCQ
*601158 C-JUN KINASE
*311800 PHOSPHOGLYCERATE KINASE 1; PGK1
*601988 LIM DOMAIN KINASE 2; LIMK2
*601298 ACTIVIN A RECEPTOR, TYPE II-LIKE KINASE 2; ACVRLK2
*147795 JANUS KINASE 1; JAK1
*147670 INSULIN RECEPTOR; INSR
*115440 CASEIN KINASE 2, ALPHA 1 POLYPEPTIDE; CSNK2A1
*115441 CASEIN KINASE 2, BETA POLYPEPTIDE; CSNK2B
*115442 CASEIN KINASE 2, ALPHA-PRIME SUBUNIT; CSNK2A2
*208900 ATAXIA-TELANGIECTASIA; AT
*154235 MALE GERM CELL-ASSOCIATED KINASE; MAK
*600526 ELKL MOTIF KINASE; EMK1
*151410 LEUKEMIA, CHRONIC MYELOID; CML
*601983 HEMATOPOIETIC PROGENITOR KINASE 1
*164761 RET PROTO-ONCOGENE; RET
*600864 CASEIN KINASE 1, DELTA; CSNK1D
*600863 CASEIN KINASE 1, EPSILON; CSNK1E
*600664 CONSERVED HELIX-LOOP-HELIX UBIQUITOUS KINASE; CHUK
*143890 HYPERCHOLESTEROLEMIA, FAMILIAL; FHC
*191170 TUMOR PROTEIN p53; TP53
*272800 TAY-SACHS DISEASE; TSD
*600954 DEATH-ASSOCIATED PROTEIN; DAP
*164730 V-AKT MURINE THYMOMA VIRAL ONCOGENE HOMOLOG 1; AKT1
*120150 COLLAGEN, TYPE I, ALPHA-1 CHAIN; COL1A1
*202500 SEVERE COMBINED IMMUNODEFICIENCY DISEASE-1; SCID1
*175100 ADENOMATOUS POLYPOSIS OF THE COLON; APC
*601792 PROTEIN PHOSPHATASE 1, REGULATORY (INHIBITOR) SUBUNIT 2; PPP1R2
*601530 UBIQUITIN-BINDING PROTEIN P62
*310300 MUSCULAR DYSTROPHY, TARDIVE, DREIFUSS-EMERY TYPE, WITH CONTRACTURES
*601047 CAVEOLIN, CAVEOLAE PROTEIN, 22-KD; CAV
*134934 FIBROBLAST GROWTH FACTOR RECEPTOR-3; FGFR3
*219700 CYSTIC FIBROSIS; CF
*308000 HYPOXANTHINE GUANINE PHOSPHORIBOSYLTRANSFERASE 1; HPRT1
*601523 GROWTH FACTOR RECEPTOR-BOUND PROTEIN-10; GRB10
*238600 HYPERLIPOPROTEINEMIA, TYPE I
*600140 CREB-BINDING PROTEIN; CREBBP
*152690 THYROID AUTOANTIGEN 70 KD; G22P1
*164960 ONCOGENE PIM-1; PIM1; PIM

TABLE 3-continued

Examples of Useful Kinases--Serine Protein Kinases

*102582 SIGNAL TRANSDUCER AND ACTIVATOR OF TRANSCRIPTION 3; STAT3
*123810 CYCLIC-AMP-RESPONSE-ELEMENT-BINDING PROTEIN-1; CREB 1
*601497 BCL2-ASSOCIATED ATHANOGENE 1; BAG1
*601269 P32 SPLICING FACTOR SF2 ASSOCIATED PROTEIN
*601146 CARTILAGE-DERIVED MORPHOGENETIC PROTEIN 1
*601702 p160-ROCK
*601524 GROWTH FACTOR RECEPTOR-BOUND PROTEIN-14; GRB14
*273800 THROMBASTHENIA OF GLANZMANN AND NAEGELI
*147545 INSULIN RECEPTOR SUBSTRATE 1; IRS1
*233700 GRANULOMATOUS DISEASE, CHRONIC, AUTOSOMAL CYTOCHROME-b-POSITIVE FORM I
*600179 GUANYLATE CYCLASE 2D, MEMBRANE; GUC2D
*230400 GALACTOSEMIA
*180380 RHODOPSIN; RHO
*190182 TRANSFORMING GROWTH FACTOR-BETA RECEPTOR, TYPE II; TGFBR2
*308100 ICHTHYOSIS, X-LINKED
*601893 TRIPLE FUNCTIONAL DOMAIN; TRIO
*601366 MOTHERS AGAINST DECAPENTAPLEGIC (*DROSOPHILA*) HOMOLOG 2; MADH2
*311030 MCF.2 CELL LINE DERIVED TRANSFORMING SEQUENCE; MCF2
*133430 ESTROGEN RECEPTOR; ESR
*311010 V-RAF MURINE SARCOMA 3611 VIRAL ONCOGENE HOMOLOG 1; ARAF1
*164710 V-RAF MURINE SARCOMA 3611 VIRAL ONCOGENE HOMOLOG 2; ARAF2
*600799 BONE MORPHOGENETIC RECEPTOR TYPE II; BMPR2
*230800 GAUCHER DISEASE, TYPE I; GD I
*190181 TRANSFORMING GROWTH FACTOR-BETA RECEPTOR, TYPE I; TGFBR1
*189972 GENERAL TRANSCRIPTION FACTOR IIH, POLYPEPTIDE 1; GTF2H1
*118888 CHYMOTRYPSIN-LIKE PROTEASE; CTRL
*232600 GLYCOGEN STORAGE DISEASE V
*123835 CYCLIN A; CCNA
*600966 LETHAL GIANT LARVAE (*DROSOPHILA*) HOMOLOG 1; LLGL1
*306400 GRANULOMATOUS DISEASE, CHRONIC; CGD
*115460 CASEIN, BETA; CSN2
*600980 DENTIN MATRIX ACIDIC PHOSPHOPROTEIN 1; DMP1
*154500 TREACHER COLLINS-FRANCESCHETTI SYNDROME 1; TCOF1
*516050 COMPLEX IV, CYTOCHROME c OXIDASE SUBUNIT III
*125850 DIABETES MELLITUS, AUTOSOMAL DOMINANT
*164757 V-RAF MURINE SARCOMA VIRAL ONCOGENE HOMOLOG B1; BRAF
*301300 ANEMIA, HYPOCHROMIC; ANH1
*600956 ANTI-MULLERIAN HORMONE TYPE II RECEPTOR; AMHR2
*173390 PLASMINOGEN ACTIVATOR INHIBITOR, TYPE 2; PAI2
*102576 ACTIVIN A RECEPTOR, TYPE I; ACVR1

TABLE 4

Examples of Useful Kinases--Threonine Protein Kinases

*601955 CYCLIN-DEPENDENT KINASE 7; CDK7
*160900 DYSTROPHIA MYOTONICA; DM
*600855 MINIBRAIN (*DROSOPHILA*) HOMOLOG; MNBH
*179090 RAC SERINE/THREONINE PROTEIN KINASE
*601032 SERINE-THREONINE PROTEIN KINASE N; PKN
*601959 SERINE/THREONINE PROTEIN KINASE 2; STK2
*600899 PROTEIN KINASE, DNA-ACTIVATED, CATALYTIC SUBUNIT; PRKDC
*600447 ZIPPER PROTEIN KINASE; ZPK
*601951 PROTEIN-TYROSINE KINASE STY
*176872 PROTEIN KINASE, MITOGEN-ACTIVATED, KINASE 1; PRKMK1
*300300 BRUTON AGAMMAGLOBULINEMIA TYROSINE KINASE; BTK

TABLE 4-continued

Examples of Useful Kinases--Threonine Protein Kinases

*600765 MKN28 KINASE
*300083 PROTEIN KINASE, X-LINKED; PRKX
*176946 ELK-RELATED TYROSINE KINASE; ERK
*306000 GLYCOGEN STORAGE DISEASE VIII
*266200 PYRUVATE KINASE DEFICIENCY OF ERYTHROCYTE
*300075 RIBOSOMAL PROTEIN S6 KINASE, 90 KD, POLYPEPTIDE 3; RPS6KA3
*600831 DEATH-ASSOCIATED PROTEIN KINASE 1; DAPK1
*311550 PCTAIRE PROTEIN KINASE 1; PCTK1
*176871 PROTEIN KINASE, INTERFERON-INDUCIBLE DOUBLE-STRANDED RNA; PRKR
*601284 ACTIVIN A RECEPTOR, TYPE II-LIKE KINASE 1; ACVRLK1
*400008 PROTEIN KINASE, Y-LINKED; PRKY
*137026 G PROTEIN-COUPLED RECEPTOR KINASE 2 (*DROSOPHILA*)-LIKE; GPRK2L
*601639 PROTEIN KINASE, cAMP-DEPENDENT, CATALYTIC, ALPHA; PRKACA
*600448 PROTEIN KINASE C, THETA FORM; PRKCQ
*310200 MUSCULAR DYSTROPHY, PSEUDOHYPERTROPHIC PROGRESSIVE, DUCHENNE AND BECKER TYPES; DMD
*601329 LIM DOMAIN KINASE 1; LIMK1
*311800 PHOSPHOGLYCERATE KINASE 1; PGK1
*601988 LIM DOMAIN KINASE 2; LIMK2
*601158 C-JUN KINASE
*601298 ACTIVIN A RECEPTOR, TYPE II-LIKE KINASE 2; ACVRLK2
*147795 JANUS KINASE 1; JAK1
*115440 CASEIN KINASE 2, ALPHA 1 POLYPEPTIDE; CSNK2A1
*115441 CASEIN KINASE 2, BETA POLYPEPTIDE; CSNK2B
*154235 MALE GERM CELL-ASSOCIATED KINASE; MAK
*251170 MEVALONICACIDURIA
*600526 ELKL MOTIF KINASE; EMK1
*115442 CASEIN KINASE 2, ALPHA-PRIME SUBUNIT; CSNK2A2
*601254 MAP KINASE KINASE 6
*600863 CASEIN KINASE 1, EPSILON; CSNK1E
*600864 CASEIN KINASE 1, DELTA; CSNK1D
*151410 LEUKEMIA, CHRONIC MYELOID; CML
*600664 CONSERVED HELIX-LOOP-HELIX UBIQUITOUS KINASE; CHUK
*601983 HEMATOPOIETIC PROGENITOR KINASE 1
*164761 RET PROTO-ONCOGENE; RET
*601792 PROTEIN PHOSPHATASE 1, REGULATORY (INHIBITOR) SUBUNIT 2; PPP1R2
*600714 DUAL SPECIFICITY PHOSPHATASE 1; DUSP1
*164730 V-AKT MURINE THYMOMA VIRAL ONCOGENE HOMOLOG 1; AKT1
*600954 DEATH-ASSOCIATED PROTEIN; DAP
*191170 TUMOR PROTEIN p53; TP53
*232300 GLYCOGEN STORAGE DISEASE II
*202500 SEVERE COMBINED IMMUNODEFICIENCY DISEASE-1; SCID1
*601530 UBIQUITIN-BINDING PROTEIN P62
*238600 HYPERLIPOPROTEINEMIA, TYPE I
*601497 BCL2-ASSOCIATED ATHANOGENE 1; BAG1
*164960 ONCOGENE PIM-1; PIM1; PIM
*308000 HYPOXANTHINE GUANINE PHOSPHORIBOSYLTRANSFERASE 1; HPRT1
*601702 p160-ROCK
*601146 CARTILAGE-DERIVED MORPHOGENETIC PROTEIN 1
*219700 CYSTIC FIBROSIS; CF
*272800 TAY-SACHS DISEASE; TSD
*120150 COLLAGEN, TYPE I, ALPHA-1 CHAIN; COL1A1
*233700 GRANULOMATOUS DISEASE, CHRONIC, AUTOSOMAL CYTOCHROME-b-POSITIVE FORM I
*162300 NEUROMATA, MUCOSAL, WITH ENDOCRINE TUMORS
*190182 TRANSFORMING GROWTH FACTOR-BETA RECEPTOR, TYPE II; TGFBR2
*230400 GALACTOSEMIA
*601366 MOTHERS AGAINST DECAPENTAPLEGIC (*DROSOPHILA*) HOMOLOG 2; MADH2
*601893 TRIPLE FUNCTIONAL DOMAIN; TRIO
*600956 ANTI-MULLERIAN HORMONE TYPE II RECEPTOR; AMHR2
*600799 BONE MORPHOGENETIC RECEPTOR TYPE II; BMPR2
*164757 V-RAF MURINE SARCOMA VIRAL ONCOGENE HOMOLOG B1; BRAF

TABLE 4-continued

Examples of Useful Kinases--Threonine Protein Kinases

*123835 CYCLIN A; CCNA
*516050 COMPLEX IV, CYTOCHROME c OXIDASE SUBUNIT III
*180380 RHODOPSIN; RHO
*311010 V-RAF MURINE SARCOMA 3611 VIRAL ONCOGENE HOMOLOG 1; ARAF1
*306400 GRANULOMATOUS DISEASE, CHRONIC; CGD
*190181 TRANSFORMING GROWTH FACTOR-BETA RECEPTOR, TYPE I; TGFBR1
*301300 ANEMIA, HYPOCHROMIC; ANH1
*189972 GENERAL TRANSCRIPTION FACTOR IIH, POLYPEPTIDE 1; GTF2H1
*232600 GLYCOGEN STORAGE DISEASE V
*230800 GAUCHER DISEASE, TYPE I; GD I
*102600 ADENINE PHOSPHORIBOSYLTRANSFERASE; APRT
*164710 V-RAF MURINE SARCOMA 3611 VIRAL ONCOGENE HOMOLOG 2; ARAF2
*102576 ACTIVIN A RECEPTOR, TYPE I; ACVR1

In one embodiment, the protein kinase of the invention is a receptor tyrosine kinase (RTK). RTKs recognize peptide growth factor ligands (e.g., hormones). The binding of a ligand leads to autophosphorylation of RTKs and stimulates the receptor's tyrosine kinase activity, which subsequently stimulates a signal transduction cascade. The RTK pathways are involved in regulation of cell proliferation and differentiation, and many other functions by transmitting a hormone signal to Ras, a monomeric G protein that passes the signal on to downstream components. Receptor tyrosine kinases (RTKs) have been shown to be involved in cancer (see, e.g., Rowinsky (2003) The Oncologist, 8:5-17; Bucher, et al., (2004), Swiss Med. Wkly., 134:145-153; Gotlib et al., 2004, Blood, 103: 2879-91), and cardiovascular diseases (e.g., see Force et al. (2004) Circulation, 109:1196-1205), as well as other diseases.

In one embodiment, the RTK is selected from the group consisting of: Ax1 (P30530), ErbB3 (NP_001973), PDGF R .α(NP_006197), Dtk (P55144), ErbB4 (Q15303), PDGF R .beta. (NP_002600), PDGF R .beta. (P02452), FGF R1 (NP_056934), c-Ret (P07949), EphA1 (NP_005223), FGF R2 α(NP_002010), ROR1 (Q01973), EphA2 (NP_004422), FGF R3 (NM-022965), ROR2 (Q01974), EphA3 (NP_872585), FGF R4 (NM_022965), SCF R (NP_954637), EphA4 (P54764), Flt-3 (NP_000750), Tie-1 (P35590), EphA6 (P54758), HGF R (Q04756), Tie-2 (Q02763), EphA7 (NP_004431), IGF-1 R(NP_000609), TrkA (P04629), EphB1 (NP_004432), Insulin R(NP_034700), TrkB (Q16620), EphB2 (NP_004433), M-CSF R (P07333), TrkC (CAA12029), EphB4 (NP_004435), Mer (Q12866), VEGF R1 (NP_003367), EphB6 (NP_004436), MSP R (Q04912), VEGF R2 (AAR26285), ErbB2 (NP_004439), MuSK (NP_005583), and VEGF R3 (P35916). The numbers in the parentheses represent NCBI protein accession numbers for the RTKs.

In another embodiment, the protein kinase is a Mitogen-activated protein kinase (MAPK). Activated Ras induces a kinase signal cascade that culminates in activation of MAPK. MAPKs are serine/threonine kinases that can translocate into the nucleus of the cell, and phosphorylate transcription factors that regulate gene expression. Multiple MAPK pathways are found in eukaryotic cells, and lead to different specific actions depending on the stimulus. MAPKs may, amongst other things, promote expression of cyclins, proteins involved in cell division (cell cycle).

In another embodiment of the invention, the kinase is an MAPK-activated protein (MAPKAP) kinase which is also a serine/threonine kinase. Several MAPKAP kinases are activated by MAPK family members termed extracellular signal-regulated kinases (ERK1/ERK2) and stress activated protein kinase 2 (SAPK2, also called p38). The MAPKAP kinases can be subdivided into two groups; those comprising two kinase domains in a single polypeptide, and those with a single kinase domain. For example, the MAPKAP kinases comprising a single kinase domain are MAPKAP-K2, MAP-KAP-K3, MAPKAP-K5 (also called p38-regulated activated kinase or PRAK) and MAPK-integrating kinase (MNK). MAPKAP-K2 and MAPKAP-K3 are activated by SAPK2 in vivo and one of their physiological substrates is heat shock protein (HSP) 27. MAPKAP-K5 is also activated in vivo by SAPK2. MAPKAP-K2 is involved in controlling production of the proinflammatory cytokines, tumomecrosis factor, interleukin 6 and interferon γ, at a post-transcriptional level. The cellular response to DNA damage is mediated by evolutionarily conserved Ser/Thr kinases, phosphorylation of Cdc25 protein phosphatases, binding to 14-3-3 proteins, and exit from the cell cycle. MAPKAP kinase-2 is directly responsible for Cdc25B/C phosphorylation and 14-3-3 binding in vitro and in response to UV-induced DNA damage within mammalian cells. Downregulation of MAPKAP kinase-2 eliminates DNA damage-induced G2/M, G1, and intra S phase checkpoints. MAPKs and MAPKAP kinases have been indicated in cancer (e.g., see Platanias (2003) Blood, 101: 4667-4679), inflammatory diseases (e.g., Hommes, et al. (2003) Gut 52:144-151), and diabetes (e.g., Shanley (2004) Invest Opthalmol Vis Sci. 45:1088-94), as well as other diseases.

In one embodiment, the MAPKAP kinase contains a sequence represented by NCBI protein accession number AAD09136, AA960234, AAH24559, or AAH63064.

In another embodiment, the protein kinase is a phosphoinositide 3 (PI3) kinase. PI3 kinases are activated by growth factors, insulin and G-protein coupled receptors and convert phosphatidylinositol 4,5-bisphosphate into phosphatidylinositol 3,4,5-triphosphate (PIP3), a ubiquitous second messager. PIP3 binds to a variety of effector molecules including protein serine/threonine kinases (protein kinase B, PDK1), Tec family protein tyrosine kinases, and regulators of monomeric G-proteins (such as GRP 1) that control cell growth, proliferation and shape, prevent apoptosis, stimulate directed cell movement and mediate the metabolic actions of insulin. PI3 has been indicated in diabetes (e.g., Shanley (2004) Invest Opthalmol V is Sci. 45:1088-94; Storz (1999) Eur J. Biochem. 266:17-25), and other diseases. In one embodiment, the PI3 kinase is p110β or p85α.

Isolated Kinase Peptides

The present invention provides novel isolated kinase peptides, as well as a mixture containing two or more kinase peptides.

As used herein, the term "peptide" refers to a natural or synthetic molecule comprising two or more amino acids linked by the carboxyl group of one amino acid and the amino group of another. A peptide of the present invention is not limited by length, thus the term encompasses "polypeptide" and "protein." A "kinase peptide" of the present invention is a peptide fragment derived from a kinase protein and is preferably between about 2 to about 100 amino acids in length, more preferably between about 5 to about 50 amino acids in length, more preferably between about 10 to about 30 amino acids in length, even more preferably between about 10 to about 20 amino acids in length. The terms "polypeptide" and "protein" sometimes are used interchangeably. A "kinase polypeptide" or "kinase protein" may refer to an entire kinase protein, or to fragment or variant thereof.

Preferably, the kinase peptide of the present invention contains an epitope for the production of an antibody specifically immunoreactive to the kinase peptide.

In a preferred embodiment, the peptide of the present invention comprises a peptide containing an epitope, either an immunogenic epitope or an antigenic epitope. An "immunogenic epitope" as used herein, refers to a portion of a peptide that elicits an antibody response in an animal, as determined by any method known in the art, for example, by the methods for generating antibodies described herein. (See, for example, Geysen et al., 1983, Proc. Natl. Acad. Sci. USA, 81:3998-4002). The term "antigenic epitope" as used herein refers to a portion of a protein to which an antibody can immunospecifically bind to its antigen as determined by any method well known in the art, for example, by the immunoassays described herein. Antigenic epitopes need not necessarily be immunogenic. Peptides that function as epitopes may be produced by any conventional means. (See, e.g., Houghten, 1985, Proc. Natl. Acad. Sci. USA, 82:5131-5135; and as described in U.S. Pat. No. 4,631,211).

As used herein, the term "isolated," with respect to peptides, nucleic acids, or antibodies, refers to that the material is removed from its original environment (e.g., the natural environment if it is naturally occurring). For example, a naturally-occurring nucleic acid or peptide or antibody present in a living animal is not isolated, but the same nucleic acid or peptide or antibody, which is separated from some or all of the coexisting materials in the natural system, is isolated. Such isolated nucleic acid could be part of a vector and such isolated nucleic acid or peptide or antibody could be part of a composition, and still be isolated in that the vector or composition is not part of its natural environment. An "isolated" peptide, nucleic acid or antibody, also includes material synthesized, or produced by recombinant DNA technology, as well as preparations such as serum containing an antibody of the invention.

In one embodiment, the kinase peptide of the invention is synthesized by methods known in the art and as described below. In another preferred embodiment, the kinase peptide is produced by expressing a nucleic acid encoding the peptide.

Kinase peptides can be synthesized by different methods well known in the art. For example, including ribosomally-directed fermentation methods, as well as non-ribosomal strategies and chemical synthesis methods. Kinase peptides containing the 20 natural amino acids can be prepared via recombinant expression systems that utilize the ribosomally directed peptide synthesis machinery of a host organism, e.g., E. coli. Alternatively, kinase peptides, including those containing unnatural or non-proteninogenic amino acids or modified amino acid side chains can be prepared through a solution-phase chemical synthesis of peptides (e.g., using N-Boc protection and the activated ester route). Protocols for sequence solution-phase chemical synthesis of peptides have been described in Andersson et al., Biopolymers 55:227-250 (2000). One method used for generating peptides is solution-phase chemical synthesis, which employs a N-tert-butoxy (N-Boc) protected amino acid and a C-protected amino acid (Andersson et al., Biopolymers 55: 227-250 (2000)). An alternative solution-phase method for chemically-catalyzed peptide synthesis employs pre-activated esters as the carboxyl component for coupling (Andersson et al., Biopolymers 55: 227-250 (2000)). In addition, enzyme-mediated solid-phase peptide synthesis has also been employed. Solid-phase peptide synthesis (SPPS) uses insoluble resin supports, and has simplified and accelerated peptide synthesis and facilitated purification (Merrifield, R. B., J. Am. Chem. Soc. 85: 2149-2154 (1963)). Since the growing peptide is anchored on an insoluble resin, unreacted soluble reagents can be removed by simple filtration or washing without manipulative losses. Solid phase peptide synthesis can be performed using automation. Those skilled in the art will recognize that various peptides are within the spirit and scope of the present invention.

The kinase peptides according to the present invention can be modified, for example, by the addition of an acetyl or amine group or amino acids at the amino- and/or carboxy-terminus of the peptide. Amino acid addition modifications may also be performed, for example, to alter the conformation of the epitope bearing peptide such that the epitope will have a conformation more closely related to the structure of the epitope in the native protein. An example of a modified epitope-bearing peptide of the invention is a peptide in which one or more cysteine residues have been added to the peptide to allow for the formation of a disulfide bond between two cysteines, thus resulting in a stable loop structure of the epitope-bearing peptide under non-reducing conditions. Disulfide bonds can form between a cysteine residue added to the peptide and a cysteine residue of the naturally-occurring epitope, or between two cysteines which have both been added to the naturally-occurring epitope-bearing peptide.

In addition, it is possible to modify one or more amino acid residues of the peptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing peptides contemplated by this invention include biotinylation.

In one embodiment, the kinase peptide of the invention is modified by adding an acetyl group at the amino terminus and/or an amide group at the carboxyl terminus.

The kinase peptide of the invention may be provided as a chimeric peptide, such as in the form of a fusion peptide. For instance, the kinase peptide can be provided as a recombinant fusion peptide which includes a second peptide portion having an amino acid sequence unrelated (heterologous) to the kinase peptide. For example, the second peptide portion may be glutathione-S-transferase, or a peptide with an enzymatic activity such as alkaline phosphatase, or an epitope tag.

In one embodiment, the kinase peptide of the present invention has a biological activity including the ability to bind to a ligand, phosphorylate a tyrosine, serine or threonine residue of a protein or peptide substrate. For example, the kinase peptide may compete with a kinase protein in binding to the ligand, thus specifically modulates the activities of the kinase protein.

In one embodiment, the kinase peptide contains an amino acid sequence that is identical with or homologous to a sequence represented by anyone of SEQ ID NOs. 1-23. A homologous sequence is at least 70%, 75%, 80%, 85%, 90%, or 95% identical to the peptide represented by anyone of SEQ ID NOs. 1-23.

```
RTK Peptides:
SEQ ID NO. 1         YVHHRDLAAARNIL

SEQ ID NO. 2         CIHRRDLAARNNVL

SEQ ID NO. 3         FVHRDLAAARNNCM
```

-continued

| | |
|---|---|
| SEQ ID NO. 4 | LVHRDDLLAARNVL |
| SEQ ID NO. 5 | FIHHRDIAAARNCL |
| SEQ ID NO. 6 | FVHRDDLATRNCCL |
| MAPKAP Peptides: | |
| SEQ ID NO. 7 | KKLNRTLSVA |
| SEQ ID NO. 8 | CEQIKIKKIEDASNP |
| SEQ ID NO. 9 | KQAGSSSASQGCNNQG |
| SEQ ID NO. 10 | CSHNSLTpTP |
| SEQ ID NO. 11 | CNSSKPTPQLKPIES |
| PI3 Peptides: | |
| SEQ ID NO. 12 | CTEDRIQHALERR |
| SEQ ID NO. 13 | CYKPEKSDLLSSPP |
| SEQ ID NO. 14 | KGLHEFDSLK |
| SEQ ID NO. 15 | NEPLEFDINI |
| SEQ ID NO. 16 | LNSLIKLNAV |
| SEQ ID NO. 17 | EVVSTSETIA |
| SEQ ID NO. 18 | KQKFDEALRE |
| SEQ ID NO. 19 | KKGLECSTLY |
| SEQ ID NO. 20 | AEWYWGDISR |
| SEQ ID NO. 21 | DVKLLYPVSK |
| SEQ ID NO. 22 | IQRIMHNYDK |
| SEQ ID NO. 23 | EDDEDLPHHD |

In a preferred embodiment, the kinase peptide is encoded by a nucleic acid containing any combination of nucleotide degeneracy.

The invention also provides a mixture of two or more kinase peptides, each containing an amino acid sequence that is identical with or homologous to a sequence represented in SEQ ID NOs. 1-23. In one embodiment, the mixture contains two or more peptides, each containing an amino acid sequence that is identical with or homologous to a sequence represented in SEQ ID NOs. 1-6. In another embodiment, the mixture contains two or more peptides, each containing an amino acid sequence that is identical with or homologous to a sequence represented in SEQ ID NOs. 7-11. In another embodiment, the mixture contains two or more peptides, each containing an amino acid sequence that is identical with or homologous to a sequence represented in SEQ ID NOs. 12-23.

The peptides may be derivatized e.g., by conjugation with bovine serum albumin (BSA), or keyhole limpet hemocyanin (KLH), and/or with a functional group such as hydroxy (—OH), acetyl (—$CH_2COOH$) or amide (—$NH_2$).

Antibodies Against Kinase Peptides

The present invention also provides kinase antibodies that are specifically immunoreactive to peptides, e.g., the kinase peptides and kinase proteins as described above. The antibodies may be polyclonal or monoclonal or recombinant, produced by methods known in the art or as described below.

As use herein, the term "specifically immunoreactive" refers to a measurable and reproducible specific immunoreaction such as binding between a peptide and an antibody, that is determinative of the presence of the peptide in the presence of a heterogeneous population of peptides and other biologics. The term "specifically immunoreactive" may include specific recognition of structural shapes and surface features. Thus, under designated conditions, an antibody specifically immunoreactive to a particular peptide does not bind in a significant amount to other peptides present in the sample. An antibody specifically immunoreactive to a peptide has an association constant of at least $10^3 M^{-1}$ or $10^4 M^{-1}$, sometimes about $10^5 M^{-1}$ or $10^6 M^{-1}$, in other instances $10^6 M^{-1}$ or $10^7 M^{-1}$, preferably about $10^8 M^{-1}$ to $10^9 M^{-1}$, and more preferably, about $10^{10} M^{-1}$ to $10^{11} M^{-1}$ or higher. A variety of immunoassay formats can be used to determine antibodies specifically immunoreactive to a particular peptide. For example, solid-phase ELISA immunoassays are routinely used to select monoclonal antibodies specifically immunoreactive with a peptide. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the term "antibody" refers to an immunoglobulin specifically immunoreactive to a given antigen (e.g., a kinase peptide of the invention). The term "antibody" as used herein is intended to include whole antibodies of any isotype (IgG, IgA, IgM, IgE, etc), and fragments thereof. An "antibody" of the invention also includes an antibody preparation, e.g., a serum (antiserum). Antibodies can be fragmented using conventional techniques and the fragments screened for utility in the same manner as whole antibodies. Thus, the term includes segments of proteolytically-cleaved or recombinantly-prepared portions of an antibody molecule that selectively reacts with a certain protein or peptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies may be labeled with detectable labels by one of skill in the art. The label can be a radioisotope, fluorescent compound, chemiluminescent compound, enzyme, or enzyme co-factor, or any other labels known in the art. In some aspects, the antibody that binds to an entity one wishes to measure (the primary antibody) is not labeled, but is instead detected by binding of a labeled secondary antibody that specifically binds to the primary antibody.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the invention can be from any animal origin including birds and mammals. Preferably, the antibodies are of human, murine (e.g., mouse and rat), donkey, sheep, rabbit, goat, guinea pig, camel, horse, or chicken origin.

As used herein, a "monoclonal antibody" refers to an antibody that recognizes only one type of antigen. This type of antibodies is produced by the daughter cells of a single antibody-producing hybridoma. A monoclonal antibody typically displays a single binding affinity for any epitope with which it immunoreacts. A monoclonal antibody may contain an antibody molecule having a plurality of antibody combining sites, each immunospecific for a different epitope, e.g., a bispecific monoclonal antibody. Monoclonal antibodies may be obtained by methods known to those skilled in the art. (Kohler and Milstein (1975), Nature, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), ANTIBODIES: A Laboratory Manual, Cold Spring Harbor Laboratory; Colligan et al. (1992, 1993), eds., Current Protocols in Immunology, Greene Publishing Assoc. and Wiley Interscience, N.Y.).

The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. (See, e.g., WO 93/17715; WO 92/08802; WO 91/00360; WO 92/05793; Tutt et al., 1991, J. Immunol., 147:60-69; U.S. Pat. Nos. 4,474,893; 4,714,681; 4,925,648; 5,573,920; 5,601,819; and Kostelny et al., 1992, J. Immunol., 148:1547-1553). For example, the antibodies may be produced against a peptide containing repeated units of a kinase peptide sequence of the invention, or they may be produced against a peptide containing two or more kinase peptide sequences of the invention, or the combination thereof.

Moreover, antibodies can also be prepared from any region of the peptides and kinase peptides of the invention. In addition, if a polypeptide is a receptor protein, e.g., a receptor kinase, antibodies can be developed against an entire receptor or portions of the receptor, for example, an intracellular domain, an extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example.

In the present invention, the kinase peptides for generating antibodies preferably contain a sequence of at least 4, at least 5, at least 6, at least 7, more preferably at least 8, at least 9, at least 10, at least 11, at least 12, at least 13, at least 14, at least 15, and, preferably, between about 5 to about 50 amino acids in length, more preferably between about 10 to about 30 amino acids in length, even more preferably between about 10 to about 20 amino acids in length. The preferred kinase peptides are those derived from the RTK proteins listed in Table 1 above; that is, preferred kinase peptides have an amino acid sequence the same as or homologous to a portion of the sequence of the proteins listed in Table 1.

The monoclonal antibodies of the present invention can be prepared using well-established methods. In one embodiment, the monoclonal antibodies are prepared using hybridoma technology, such as those described by Kohler and Milstein (1975), Nature, 256:495. In a hybridoma method, a mouse, hamster, or other appropriate host animal, is typically immunized with an immunizing agent (e.g., a kinase peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-1031. Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol. (1984), 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding specificity of the monoclonal antibody can, for example, be determined by the Scatchard analysis of Munson and Pollard (1980), Anal. Biochem., 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Polyclonal antibodies of the invention can also be produced by various procedures well known in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100 µg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Antibodies encompassed by the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv, or disulfide stabilized antibody domains recombinantly fused to either the phage polynucleotide III or polynucleotide VIII protein. Examples of phage display methods that can be used to make the antibodies of the present invention include those disclosed in Brinkman et al. (1995) J. Immunol. Methods, 182:41-50; Ames et al. (1995) J. Immunol. Methods, 184:177-186; Kettleborough et al. (1994) Eur. J. Immunol., 24:952-958; Persic et al. (1997) Gene, 187:9-18; Burton et al. (1994) Advances in Immunology, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce antibody fragments such as single-chain Fvs and antibodies include those described in U.S. Pat. Nos. 4,946,778 and 5,258,498; Huston et al. (1991) Methods in Enzymology, 203:46-88; Shu et al. (1993) Proc. Natl. Acad. Sci. USA, 90:7995-7999; and Skerra et al. (1988) Science, 240:1038-1040, each of which is incorporated herein by reference in its entirety.

For some uses, including the in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (See, e.g., Morrison (1985), Science, 229:1202; Oi et al. (1986), BioTechniques, 4:214; Gillies et al. (1989), J. Immunol. Methods, 125:191-202; and U.S. Pat. Nos. 5,807,715; 4,816,567; and 4,816,397, which are incorporated herein by reference in their entirety).

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (See, e.g., Queen et al., U.S. Pat. Nos. 5,693,762 and 5,585,089; and Riechmann et al. (1988) Nature, 332:323, which are incorporated herein by reference in their entireties). Antibodies can be humanized using a variety of techniques known in the art, including, for example, CDR-grafting (EP 239, 400; PCT publication WO 91/09967; U.S. Pat. Nos. 5,225,539; 5,530,101; and 5,585,089); veneering or resurfacing (EP 592,106; EP 519,596; Padlan (1991), Molecular Immunology, 28(4/5):489-498; Studnicka et al. (1994) Protein Engineering, 7(6):805-814; Roguska et al. (1994) Proc. Natl. Acad. Sci. USA, 91:969-973; and chain shuffling (U.S. Pat. No. 5,565,332).

Completely human antibodies are particularly desirable for therapeutic treatment of human patients, so as to avoid or alleviate immune reaction to foreign protein. Human antibodies can be made by a variety of methods known in the art, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the J.sub.H region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (1995) Intl. Rev. Immunol., 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In one embodiment, the present invention provides antibodies that specifically immuoreact to a tyrosine kinase protein, or fragment or variant thereof.

In one embodiment, the invention provides a novel monoclonal antibody that specifically recognizes a sequence selected from the group consisting of SEQ ID NOs. 1-6. The monoclonal antibodies are hereinafter referred to as anti-receptor-tyrosine kinase monoclonal antibodies ("RTK-MAb").

The present invention also provides antibodies that specifically immuoreact to a MAPKAP kinase protein, or fragment or variant thereof.

In one embodiment, the invention provides a novel monoclonal antibody that specifically recognizes a sequence selected from the group consisting of SEQ ID NOs. 7-11. The monoclonal antibodies are hereinafter referred to as anti-receptor-MAPKAP kinase monoclonal antibodies ("MAPKAP-K-MAb").

The present invention also provides antibodies that specifically immuoreact to a PI3 kinase protein, or fragment or variant thereof.

In one embodiment, the invention provides a novel monoclonal antibody that specifically recognizes a sequence selected from the group consisting of SEQ ID NOs. 12-23. The monoclonal antibodies are hereinafter referred to as anti-receptor-phosphoinositide 3 kinase monoclonal antibodies ("PI3 kinase-MAb").

The invention further provides a mixture containing two or more monoclonal antibodies produced as described above. In a preferred embodiment, the mixture contains two or more monoclonal antibodies raised against different kinase peptides derived from the same kinase protein. In another preferred embodiment, the mixture contains two or more monoclonal antibodies raised against different kinase peptides, at least two of which are derived from different kinase proteins.

In one embodiment, the antibody mixture contains two or more antibodies raised against peptides containing the amino acid sequence selected from the group consisting of: SEQ ID NOs. 1-6.

In another embodiment, the antibody mixture contains two or more antibodies raised against peptides containing the amino acid sequence selected from the group consisting of: SEQ ID NOs. 7-11.

In yet another embodiment, the mixture contains two or more antibodies raised against peptides containing the amino acid sequence selected from the group consisting of: SEQ ID NOs. 12-23.

Pan-Antibodies Against Kinase Peptides

In a preferred aspect, the present invention comprises polyclonal antibodies raised against a mixture of two or more peptides derived from a kinase polypeptide or protein. The inventive polyclonal antibodies immunoreact with at least two, up to an entire class of, kinase polypeptides or proteins, and thus are referred to as "pan" antibodies.

In one embodiment, the present invention provides polyclonal antibodies that specifically immuoreact with at least about two to ten, preferably at least about two to twenty, more preferably at least about twenty to fifty, up to entire class of tyrosine kinase proteins, or fragments or variants thereof.

In one embodiment, the invention provides novel polyclonal antibodies that specifically recognize and immunoreact with at least two sequences selected from the group consisting of SEQ ID NOs. 1-6. The polyclonal antibodies are hereinafter referred to as anti-receptor-pan-tyrosine kinase polyclonal antibodies ("pan-RTK" antibodies).

The present invention also provides polyclonal antibodies that specifically immuoreact with at least about two to ten, preferably at least about two to twenty, more preferably at least about twenty to fifty, up to entire class of MAPKAP kinase proteins, or fragments or variants thereof.

In one embodiment, the invention provides antibodies that specifically recognize and immunoreact with at least two sequences selected from the group consisting of SEQ ID NOs. 7-11. The polyclonal antibodies are hereinafter referred to as anti-receptor-pan-MAPKAP kinase polyclonal antibodies ("pan-MAPKAP-K" antibodies).

The present invention also provides polyclonal antibodies that specifically immuoreact with at least about two to ten, preferably at least about two to twenty, more preferably at least about twenty to fifty, up to entire class of PI3 kinase proteins, or fragments or variants thereof.

In one embodiment, the invention provides antibodies that specifically recognize and immunoreact with at least two sequences selected from the group consisting of SEQ ID NOs. 12-23. The polyclonal antibodies are hereinafter referred to as anti-receptor-pan-phosphoinositide 3 kinase polyclonal antibodies ("pan-PI3 kinase" antibodies).

The invention further provides a mixture containing two or more polyclonal antibodies produced as described above. In a preferred embodiment, the mixture contains two or more polyclonal antibodies raised against different kinase peptides derived from the same kinase protein. In another preferred embodiment, the mixture contains two or more polyclonal antibodies raised against different kinase peptides, at least two of which are derived from different kinase proteins.

In one embodiment, the antibody mixture contains two or more pan antibodies raised against peptides containing the amino acid sequence selected from the group consisting of SEQ ID NOs. 1-6.

In another embodiment, the antibody mixture contains two or more antibodies raised against peptides containing the amino acid sequence selected from the group consisting of SEQ ID NOs. 7-11.

In yet another embodiment, the mixture contains two or more antibodies raised against peptides containing the amino acid sequence selected from the group consisting of SEQ ID NOs. 12-23.

In one embodiment, two or more kinase peptides, derived from the same or different kinase proteins, are mixed prior to antibody production, e.g., injection into an animal. The antibodies produced thus are specifically immunoreactive to the two or more kinase peptides in the mixture.

In one embodiment, two or more peptides containing the amino acid sequence selected from the group consisting of SEQ ID NOs. 1-6 are mixed before antibody production.

In another embodiment, two or more peptides containing the amino acid sequence selected from the group consisting of: SEQ ID NOs. 7-11 are mixed before antibody production.

In yet another embodiment, two or more peptides containing the amino acid sequence selected from the group consisting of SEQ ID NOs. 12-23 are mixed before antibody production.

In a preferred embodiment, the antibodies contained in a mixture, or the antibodies raised against a peptide mixture, specifically immunoreact with two or more, and up to the entire class of RTK proteins, thus referred as "pan-RTK" antibodies. Preferably, the pan-RTK antibodies react with most or all human and murine RTKs (e.g., Eph receptors and VEGF receptors). The pan-RTK antibodies may also react with a subset of nonreceptor tyrosine kinase proteins that contain the same epitopes (e.g., JAK family members, SRC family members, FAK/PTK2, ABL, and ARG kinases).

In another embodiment, the antibodies contained in a mixture, or the antibodies raised against a peptide mixture, specifically immunoreact with two or more, and up to the entire class of MAPKAP kinase proteins, thus referred as "pan-MAPKAP kinase" antibodies. Preferably, the pan-MAPKAP kinase antibodies react with most or all human and murine MAPKAP kinases (e.g., MAPKAP kinases 1, 2, 3, 4 and 5). The pan-MAPKAP kinase antibodies may also react with a subset of nonreceptor serine/threonine kinases.

In another embodiment, the antibodies contained in a mixture, or the antibodies raised against a peptide mixture, specifically immunoreact with two or more, and up to the entire class of PI3 kinase proteins, thus referred as "pan-PI3 kinase" antibodies. Preferably, the pan-PI3 kinase antibodies react with most or all human and murine PI3 kinases. The pan-p13 kinase antibodies may also react with nonreceptor serine/threonine kinases.

Preferred specifically immunoreactive antibodies include those with a dissociation constant or Kd of less than about $5\times10^{-2}$, $1\times10^{-2}$, $5.\text{times}\times10^{-3}$, $1\times10^{-3}$, $5\times10^{-4}$, or $1\times10^{-4}$. More preferred specifically immunoreactive antibodies include those with a dissociation constant or Kd less than about $5\times10^{-5}$, $1\times10^{-5}$, $5\times10^{-6}$, $1\times10^{-6}$, $5\times10^{-7}$, $1\times10^{-7}$, $5\times10^{-8}$, or $1\times10^{-8}$. Even more preferred specifically immunoreactive antibodies include those with a dissociation constant or Kd of less than about $5\times10^{-9}$, $1\times10^{-9}$, $5\times10^{-10}$, $1\times10^{-10}$, $5\times10^{-11}$, $10\times10^{-11}$, $5\times10^{-12}$, $1\times10^{-12}$, $5\times10^{-13}$, $1\times10^{-13}$, $5\times10^{-14}$, $1\times10^{-14}$, $5\times10^{-15}$, or $1\times10^{-15}$.

Nucleic Acids

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. The term "nucleic acid" is not limited by length, thus encompasses "polynucleotide" and "oligonucleotide." A "nucleic acid encoding a kinase peptide," as used herein, is preferably between about 6 to about 300 nucleotides in length, more preferably between about 15 to about 150 nucleotides in length, and more preferably, between about 30 to about 90 nucleotides in length, and more preferably, between about 30 to about 60 nucleotides in length.

In one embodiment, the invention provides a nucleic acid encoding a peptide of the invention, or a complementary sequence thereof.

In another embodiment, the invention provides a mixture containing two or more nucleic acids as described above.

As used herein, the term "stringent conditions" refers to conditions where only nucleic acid sequences which are very similar to each other will hybridize. The precise conditions determining the stringency of a particular hybridization include not only the ionic strength, temperature, and the concentration of destabilizing agents such as formamide, but also on factors such as the length of the nucleic acid sequences, their base composition, the percent of mismatched base pairs between the two sequences, and the frequency of occurrence of subsets of the sequences (e.g., small stretches of repeats) within other non-identical sequences. The conditions generally refer to hybridization at either (1) 1×SSC (10×SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 65° C.; (2) 1×SSC, 50% formamide, 1% SDS, 0.1-2 mg/ml denatured salmon sperm DNA at 42° C.; (3) 1% bovine serum albumen (fraction V), 1 mM Na$_2$.EDTA, 0.5 M NaHPO$_4$ (pH 7.2) (1 M NaHPO$_4$=134 g Na$_2$HPO$_4$7H$_2$O, 4 ml 85% H.sub.3PO$_4$ per liter), 7% SDS, 0.1-2 mg/ml denatured salmon sperm DNA at 65° C.; (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C.; (5) 5×SSC, 5×Denhardt's solution, 1% SDS, 100 μg/ml denatured salmon sperm DNA at 65° C.; or (6) 5×SSC, 5×Denhardt's solution, 50% formamide, 1% SDS, 100 μg/ml denatured salmon sperm DNA at 42° C., with high stringency washes of either (1) 0.3-0.1×SSC, 0.1% SDS at 65° C.; or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated T$_m$ of the hybrid, where T$_m$ in ° C.=(2× the number of A and T bases)+(4× the number of G and C bases). For hybrids believed to be about 18 to about 49 base pairs in length, the T$_m$ in ° C.=(81.5° C.+16.6(log$_{10}$M)+0.41(% G+C)−0.61 (% formamide)-500/L), where "M" is the molarity of monovalent cations (e.g., Na$^+$), and "L" is the length of the hybrid in base pairs.

The invention also provides a probe/primer comprising an isolated oligonucleotide, wherein the oligonucleotide comprises a region of nucleotide sequence which hybridizes under stringent conditions to at least 12 consecutive nucleotides of a nucleic acid coding a kinase peptide of the invention, or their complementary sequences thereof, or naturally occurring mutants thereof.

In one embodiment, the invention provides a mixture containing two or more probes/primers as described above.

As used herein, the term "a probe/primer" refers to a nucleic acid which binds to a target nucleic acid of complementary sequence through one or more types of chemical bonds, usually through complementary base pairing, e.g., hydrogen bond formation. As used herein, a probe/primer may include natural (i.e., A, G, C, or T) or modified on bases (7-deazaguanosine, inosine, etc.) or on sugar moiety. In addition, the bases in a probe/primer may be joined by a linkage other than a phosphodiester bond, so long as it does not interfere with hybridization. Thus, for example, probes/primers may be peptide nucleic acids in which the constituent bases are joined by peptide bonds rather than phosphodiester linkages. It will be understood by one of skill in the art that probes/primers may bind target sequences lacking complete complementarity with the probe sequence depending upon the stringency of the hybridization conditions. The probes/primers may be directly or indirectly labeled with a detectable label by methods known in the art. The primer is capable of initiating strand elongation. By assaying for the presence, absence, or the level of the probe binding or primer elongation product, one can detect the presence, absence, or the level of the target nucleic acid. Preferably, the probe/primer of the present invention is between about 8 to 100 nucleotides in length, more preferably between about 12 to 50 nucleotides, more preferably between about 12 to 35 nucleotides in length.

As used herein, the term "detectable label" refers to a composition detectable by spectroscopic, photochemical, biochemical, immunochemical, or chemical means. The detectable label can be selected, e.g., from a group consisting of radioisotopes, fluorescent compounds, enzymes, and enzyme co-factors.

The present invention also provides nucleic acids encoding an antibody of the invention (including molecules comprising, or alternatively consisting of, antibody fragments or variants thereof). In a specific embodiment, a nucleic acid of the invention encodes an antibody (including molecules comprising, or alternatively consisting of, antibody fragments or variants thereof), comprising, or alternatively consisting of, a $V_H$ domain having an amino acid sequence of any one of the $V_H$ domains of a heavy chain expressed by an anti-kinase protein antibody-expressing cell line of the invention (e.g., a hybridoma) and a $V_L$ domain having an amino acid sequence of a light chain expressed by an anti-kinase protein antibody-expressing cell line of the invention. In another embodiment, a nucleic acid molecule of the invention encodes an antibody (including molecules comprising, or alternatively consisting of, antibody fragments or variants thereof), comprising, or alternatively consisting of, a $V_H$ domain having an amino acid sequence of any one of the $V_H$ domains of a heavy chain expressed by an anti-kinase protein antibody-expressing cell line of the invention, or a $V_L$ domain having an amino acid sequence of a light chain expressed by an anti-kinase protein antibody-expressing cell line of the invention.

Two or more nucleic acids encoding an antibody of the invention may be provided in a mixture. Standard techniques known to those of skill in the art can be used to introduce mutations in the nucleotide sequence encoding a molecule of the invention, including, for example, site-directed mutapolynucleotidesis and PCR-mediated mutapolynucleotidesis which result in amino acid substitutions. This can be used to prepare desired antibodies, e.g., humanized antibodies as described herein. Also preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, relative to the reference $V_H$ domain, $V_H$ CDR1, $V_H$ CDR2, $V_H$ CDR3, $V_L$ domain, $V_L$ CDR1, $V_L$ CDR2, or $V_L$ CDR3.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutapolynucleotidesis. The resultant mutants can be screened for biological activity to identify mutants that retain activity.

Nucleic acids encoding epitopes can also be recombined with a second nucleic acid as an epitope tag (e.g., the hemagglutinin ("HA") tag or flag tag) to aid in detection and purification of the expressed polypeptide. For example, a system for the ready purification of non-denatured fusion proteins expressed in human cell lines has been described by Janknecht et al., (1991, Proc. Natl. Acad. Sci. USA, 88:8972-897). In this system, the second nucleic acid is subcloned into a vaccinia recombination plasmid such that the open reading frame of the polynucleotide is translationally fused to an amino-terminal tag having six histidine residues. The tag serves as a matrix binding domain for the fusion protein. Extracts from cells infected with the recombinant vaccinia virus are loaded onto an Ni.sup.2+ nitriloacetic acid-agarose column and histidine-tagged proteins are selectively eluted with imidazole-containing buffers.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library, or a cDNA library generated from, (or a nucleic acid, preferably poly A+ RNA, isolated from), any tissue or cells expressing the antibody, such as hybridoma cells selected to express an antibody of the invention by PCR amplification using synthetic primers hybridizable to the 3' and 5' ends of the sequence. Alternatively, cloning using an oligonucleotide probe specific for the particular nucleic acid sequence to be identified, e.g., a cDNA clone from a cDNA library that encodes the desired antibody can be employed. Amplified nucleic acids generated by PCR can then be cloned into replicable cloning vectors using any method well known in the art.

Applications

The kinase peptides, nucleic acids encoding the kinase peptides, antibodies specifically immunoreactive with the kinase peptides, as well as nucleic acids of the present invention are useful for research and for disease detection, diagnosis, prognosis and treatment.

As nonlimiting examples, antibodies of the present invention can be used to purify, detect, and target the protein tyrosine kinase polypeptides of the present invention, including both in vitro and in vivo diagnostic, detection, screening, and/or therapeutic methods. For example, the probes/primers and antibodies can be used in immunoassays for qualitatively and quantitatively measuring levels of kinase biomarkers in biological samples. (See, e.g., Harlow et al., Antibodies: A Laboratory Manual, Cold Spring Harbor Laboratory Press, 2nd Ed. 1988, which is incorporated by reference herein in its entirety).

Probes/primers and antibodies of the invention can be used as a part of a diagnostic test kit for identifying dysfunctions associated with mis-expression of a kinase protein containing the sequence of the kinase peptide of the invention, such as for detecting in a sample of cells isolated from a patient, a level of a kinase protein, a level of a nucleic acid encoding a kinase protein; e.g. measuring a kinase mRNA level in a cell, or determining whether a genomic kinase gene has been mutated or deleted. These probes/primers of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject kinase proteins so as to inhibit expression of that protein, e.g. by inhibiting transcription and/or translation. The antibodies of the invention can also be used for therapies as described below.

Diagnosis The kinases of the present invention may serve as biomarkers for (1) diagnosis of diseases (e.g., cancer, autoimmune disease (diabetes), inflammatory disease, cardiovascular diseases, and neurological disorders), (2) prognosis of diseases (e.g., monitoring disease progression or regression from one biological state to another), (3) determination of susceptibility (risk) of a subject to diseases, or (4) evaluation of the efficacy of a treatment for a disease.

As used herein, a "biomarker" is a molecule, the level of whose nucleic acid or protein product has a quantitatively differential concentration or level with respect to an aspect of a biological state in a subject. The level of the biomarker can be measured on both the nucleic acid level and the polypeptide level. At the nucleic acid level, a nucleic acid gene or a transcript which is transcribed from any part of the subject's chromosomal and extrachromosomal genome including for example the mitochondrial genome may be measured. Preferably an RNA transcript, more preferably an RNA transcript includes a primary transcript, a spliced transcript, an alternatively spliced transcript, or an mRNA of the biomarker is measured. At the polypeptide level, a prepropeptide, a propeptide, a mature peptide or a secreted peptide of the biomarker may be measured. A biomarker can be used either solely or in conjunction with one or more other identified biomarkers, so as to allow correlation to the biological state of interest as defined herein.

Specific biomarkers of the present invention include target kinases described above, e.g., in Tables 1-4. Preferably, the biomarkers are receptor kinases, e.g., RTKs, MAPKAP kinases, and PI3 kinases.

The term "biological state" is used herein to mean the result of the occurrence of a series of biological processes. As the biological processes change relative to each other, the biological state also undergoes changes. One measurement of a biological state, is the level of activity of biologic variables such as biomarkers, parameters, and/or processes at a specified time and under specified experimental or environmental conditions. A biological state can include, for example, the state of an individual cell, an organ, a tissue, and/or a multicellular organism. A biological state can be measured in samples taken from a normal subject or a disease subject. Therefore, measuring the biological state at different time intervals may indicate the state of disease progression in a subject. The term "biological state" thus include a state that is indicative of a disease (e.g., diagnosis) a state that is indicative of the progression or regression of a disease (prognosis), a state that is indicative of the susceptibility (risk) of a subject to a disease; and a state that is indicative of the efficacy of a treatment for a disease.

The term "biological state" is also used herein to refer to clinical signs and diagnostic criteria associated with a disease state. The biological state of a disease state can be quantified with measurements of biological variables. For example, for the disease state of diabetes, the biological variables can include fasting plasma glucose, casual plasma glucose, or oral glucose tolerance test (OGTT) value.

In one embodiment the biological state can be mathematically defined by the values of x and p at a given time, as known in the art. Once a biological state of the model is mathematically specified, numerical integration of the above equation using a computer determines, for example, the time evolution of the biological variables $x(t)$ and hence the evolution of the biological state over time.

The term "reference pattern of the disease state" is used herein to mean a set of biological variables that are measured in a diseased biological system under specified experimental conditions. For example, the measurements may be performed on blood samples at some specified time following a particular glucose or insulin stimulus.

Alternatively, measurements may be performed on biopsy samples, or cell cultures derived from a diseased human or animal. Examples of diseased biological systems include cellular or animal models of the disease or a patient.

The term "baseline level," or a "control level" of biomarker expression or activity refers to the level against which biomarker expression in the test sample can be compared. In some embodiments, the baseline level can be a "normal level" (i.e., level in a sample from a normal subject). Therefore, it can be determined, based on the control or baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression typically refers to a baseline level established in a sample from the subject or from a population of individuals which is believed to be normal (i.e., non-tumorous, not undergoing neoplastic transformation, not exhibiting inappropriate cell growth). In another embodiment, a baseline can be indicative of a positive diagnosis of disease. Such a baseline level, also referred to herein as a "positive control" baseline, refers to a level of biomarker expression or biological activity established in a sample from the subject, another subject, or a population of individuals, wherein the sample was believed, based on data for that cell sample, to have the disease (i.e., tumorous, exhibiting inappropriate cell growth, cancerous). In yet another embodiment, the baseline level can be established from a previous sample from the subject being tested, so that the disease progression or regression of a subject can be monitored over time and/or so that the efficacy of a given therapeutic protocol can be evaluated over time.

Preferably, the method for establishing a baseline level of biomarker expression is selected based on the sample type, the tissue or organ from which the sample is obtained, the status of the subject to be evaluated, and, as discussed above, the focus or goal of the assay (e.g., diagnosis, staging, monitoring). Preferably, the method is the same method that will be used to evaluate the sample in the subject. In a most preferred embodiment, the baseline level is established using the same cell type as the cell to be evaluated.

In one embodiment, the baseline level of biomarker expression or biological activity is established in an autologous control sample obtained from the subject. The autologous control sample can be a sample of isolated cells, a tissue sample or a bodily fluid sample, and is preferably a cell sample or tissue sample. According to the present invention, and as used in the art, the term "autologous" means that the sample is obtained from the same subject from which the sample to be evaluated is obtained. The control sample should be of or from the same cell type and preferably, the control sample is obtained from the same organ, tissue or bodily fluid as the sample to be evaluated, such that the control sample serves as the best possible baseline for the sample to be evaluated. In one embodiment, when the goal of the assay is diagnosis of abnormal cell growth, it is desirable to take the control sample from a population of cells, a tissue or a bodily fluid which is believed to represent a "normal" cell, tissue, or bodily fluid, or at a minimum, a cell or tissue which is least likely to be undergoing or potentially be predisposed to develop tumor cell growth. For example, if the sample to be evaluated is an area of apparently abnormal cell growth, such as a tumorous mass, the control sample is preferably obtained from a section of apparently normal tissue (i.e., an area other than and preferably a reasonable distance from the tumorous mass) in the tissue or organ where the tumorous mass is growing. In one aspect, if a tumor to be evaluated is in the colon, the test sample would be obtained from the suspected tumor mass and the control sample would be obtained from a different section of the colon, which is separate from the area where the mass is located and which does not show signs of uncontrolled cellular proliferation.

A difference in kinase expression level between a test sample and a baseline, either measured at the nucleic acid or the peptide level, is considered positive for the particular purpose of the test if the difference is at least 20%, 30%, 40%, 50%, preferably at least 70%, more preferably 80%, 90%, or even more preferably 2-fold, 3-fold, 4-fold, 5-fold, 10-fold or more.

As used herein, the terms "cancer," "tumor," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

As used herein, an "autoimmune disease" refers to a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

As used herein, an "inflammatory disease or condition" refers to any disease or condition that causes increased inflammation in an individual, e.g., immune system disorders, infectious diseases, or cancer. In some embodiments the inflammatory disease or condition is a "chronic inflammatory disease or condition." A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. An inflammatory disease or condition includes the following: autoimmune system diseases, including systemic lupus erythematosus (lupus or SLE), rheumatoid arthritis, vasculitis (and its specific forms such as Wegener's granulomatosis), scleroderma, myositis, serum sickness, transplant rejection, graft versus host disease, sickle cell anemia, gout, complications of pregnancy such as pre-eclampsia, multiple sclerosis, cardiovascular disease, infectious diseases such as hepatitis virus infection, including hepatitis A, B, C, and D, HIV infection, West Nile virus, Lyme disease, etc. Each of these diseases or conditions can also be described as chronic inflammatory diseases or conditions.

The term "neurological disorder" refers to a group of disorders in which one or more regions of a subject's brain operate at frequencies which are different from the predetermined frequency for that region of the brain or from the predetermined frequencies of the other regions of the subject's brain. Examples of neurological disorders include, but are not limited to, traumatic brain injury, post traumatic stress disorder, post stroke paralysis, post traumatic brain injury paralysis, cerebral palsy, headache, depression, post chemotherapy cognitive, mood and fatigue disorder, fibromyalgia, memory loss, coma, attention deficit disorder, etc.

As used herein, the term "efficacy" refers to either inhibition to some extent, of cell growth causing or contributing to a cell proliferative disorder, or the inhibition, to some extent, of the production of factors (e.g., growth factors) causing or contributing to a cell proliferative disorder. A "therapeutic efficacy" refers to relief of one or more of the symptoms of a cell proliferative disorder. In reference to the treatment of a cancer, a therapeutic efficacy refers to one or more of the following: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; and/or 5) relieving to some extent one or more of the symptoms associated with the disorder. In reference to the treatment of a cell proliferative disorder other than a cancer, a therapeutic efficacy refers to 1) either inhibition to some extent, of the growth of cells causing the disorder; 2) the inhibition, to some extent, of the production of factors (e.g., growth factors) causing the disorder; and/or 3) relieving to some extent one or more of the symptoms associated with the disorder.

As used herein, the term "a sample" or "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A sample" or "a biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "a sample" or "a biological sample" can also refer to cells or tissue analyzed in vivo, i.e., without removal from animal. Typically, "a sample" or "a biological sample" will contain cells from the animal, but the term can also refer to non-cellular biological material, such as non-cellular fractions of blood, saliva, or urine, that can be used to measure the cancer-associated polynucleotide or polypeptides levels. "A sample" or "a biological sample" further refers to a medium, such as a nutrient broth or gel in which an organism has been propagated, which contains cellular components, such as proteins or nucleic acid molecules.

The target kinase biomarkers may originate from different parts of the cell and preferably be cell surface receptor kinases, although they can also be intracellular kinases. The kinases may be over expressed or under expressed in a sample. The level of the target kinase gene or protein can be determined by conventional methods such as expression assays to determine the level of expression of the gene, by biochemical assays to determine the level of the gene product, or by immunoassays using antibodies reactive to the kinase. Examples of detection methods include those known to those of skill in the art or taught in numerous texts and laboratory manuals (see for example, Ausubel et al. (1995) Short Protocols in Molecular Biology, 3rd Ed. John Wiley & Sons, Inc.). If appropriate, the target kinase can be identified as a cell surface molecule in tissue or in a bodily fluid, such as serum.

For example, methods of detecting nucleic acid of a kinase biomarker include but are not limited to, RNA fingerprinting, Northern blotting, polymerase chain reaction, ligase chain reaction, Qbeta replicase, isothermal amplification method, strand displacement amplification, transcription based amplification systems, nuclease protection (SI nuclease or RNAse protection assays) as well as methods disclosed in WO88/10315, WO89/06700, PCT/US87/00880, PCT/US89/01025.

For example, detecting the expression level of a nucleic acid of a kinase biomarker may include (i) providing a probe/primer of the invention; (ii) contacting the probe/primer with a sample; and (iii) detecting, by hybridization of the probe/primer to nucleic acids in the sample, the presence and absence or the level of a kinase biomarker nucleic acid. The method may also include amplifying the nucleic acid of the kinase biomarker before detecting. For instance, the probe/primer can be employed in a polymerase chain reaction (PCR) or in a ligation chain reaction (LCR). A difference in the level of expression between a test sample (e.g., from a patient subject) and a control sample (e.g., from a normal subject) is indicative of the biological state of interest. The probe/primer used may also be a mixture of two or more probes/primers as described above.

The nucleic acid detection method also includes detecting, in a sample of the subject, the presence or absence of a genetic lesion spanning a region represented by a nucleic acid encoding a kinase peptide of the invention. Detecting the genetic lesion includes ascertaining the existence of at least one of (i) deletion of one or more nucleotides from a kinase gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of a kinase protein.

In alternate embodiments, the level of a kinase protein is detected in an immunoassay using an antibody of the present invention, which is specifically immunoreactive with the kinase protein. Preferably, the method of detection comprises contacting the sample with an antibody of the present invention (including an antibody mixture) and determining the presence and absence or the level of a kinase biomarker protein. A difference in the level of expression between a test sample (e.g., from a patient subject) and a control sample (e.g., from a normal subject) is indicative of the biological state of interest. The antibody used may also be a mixture of two or more antibodies, or antibodies raised against a mixture of kinase peptides as described above.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). Zola, Monoclonal Antibodies: A Manual of Techniques, pp. 147-158 (CRC Press, Inc. 1987). A detectable label can be attached to the subject antibodies and is selected so as to meet the needs of various uses of the method which are often dictated by the availability of assay equipment and compatible immunoassay procedures. Appropriate labels include, without limitation, radionuclides (e.g., .sup.125I, .sup.131I, .sup.35S, .sup.3H, or .sup.32P), enzymes (e.g., alkaline phosphatase, horseradish peroxidase, luciferase, or .beta.-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

In another embodiment of the invention, an antibody of the invention (i.e., the primary antibody) needs not be labeled, and the presence thereof can be detected using a labeled second antibody which binds to the primary antibody.

Antibodies can be arrayed on a substrate and detection of biomarkers may be performed by antibody array method, for example, as described in an application by the same inventor entitled "Antibody Protein Analysis Chip," hereby incorporated by reference in its entirety.

The antibodies can also be used for in vivo diagnostic assays, such as in vivo imaging. Generally, the antibody is labeled with a radionuclide (such as .sup.111In, sup.99Tc, sup.14C, .sup.131I, .sup.125I, or .sup.3H) so that the cells or tissue of interest can be localized using immunoscintiography. The antibody may also be used as staining reagent in pathology, following techniques well known in the art.

One embodiment of the present invention is a method for the diagnosis of a cancer that includes determining the level of a biomarker selected from any of the genes or products encoded thereby listed in Tables 1-4 in a test sample. In this method, the level of the biomarker is indicative of the presence of cancer cells. The presence of the biomarker at an increased level as compared to a normal baseline control is an indication of the presence of a cancer, a possible predisposition to such cancer or a susceptibility to an anti-cancer therapeutic treatment. The level of the biomarker can be determined by conventional methods such as expression assays to determine the level of expression of the gene (using the probes/primers, or mixtures thereof provided by the invention), by biochemical assays to determine the level of the gene product, or by immunoassays. In one embodiment of this method, the level of the biomarker can be determined by identifying the biomarker as a cell surface molecule in tissue or by detecting the biomarker in soluble form in a bodily fluid, such as serum, that can be immobilized. The biomarker level can be determined by contacting a patient test sample with an antibody, or a fragment thereof, that binds specifically to the biomarker and determining whether the anti-biomarker antibody or fragment has bound to the biomarker. The biomarker level can be determined by using a first monoclonal antibody that binds specifically to the biomarker and a second antibody that binds to the first antibody. This method can be used to determine the prognosis for cancer in the patient or to determine the susceptibility of the patient to a therapeutic treatment.

A further embodiment of the present invention is a method for the diagnosis of a tumor or the monitoring of a tumor growth or regression or a tumor therapy in a patient. The methods include determining the level of a biomarker in a patient sample, wherein the biomarker is selected from any of the genes or products encoded thereby listed in Tables 1-4.

The present invention further provides kits for disease diagnosis, prognosis, risk assessment, and/or treatment efficacy determination. Such kits are useful in a clinical setting for use in diagnosing a patent for a disease, monitoring the disease progression, testing patient's samples (e.g., biopsied), for example, to determine or predict if the patient's disease (e.g., cancer) will be resistant or sensitive to a given treatment or therapy with a drug, compound, chemotherapy agent, or biological treatment agent. Provided in the kit are the predictor set comprising a nucleic acid or a nucleic acid mixture of the invention or an antibody or an antibody mixture of the invention. The kits may encompass desired reagents for the specific detection method to be used, e.g., nucleic acid assays and immunoassays as described above, and known in the art.

The kit preferably contains any means of detecting the expression or activity of a biomarker of the present invention in a test sample, and preferably includes a probe, PCR primers, or a mixture of nucleic acids of the invention, or an antibody, a mixture of antibodies of the invention, antigen binding peptide, or fragment thereof, that binds to a biomarker. The kit can include any reagent needed to perform a diagnostic method envisioned herein. The antibody, or fragment thereof, can be conjugated to another unit, for example a marker or immobilized to a solid carrier (substrate). The kit can also contain a second antibody for the detection of biomarker: antibody complexes. In one embodiment, the kit can contain a means for detecting a control marker characteristic of a cell type in the test sample. The antibody, or fragment thereof, may be present in free form or immobilized to a substrate such as a plastic dish, a test tube, a test rod and so on. The kit can also include suitable reagents for the detection of and/or for the labeling of positive or negative controls, wash solutions, dilution buffers and the like, as well as instructions.

More specifically, according to the present invention, a means for detecting biomarker expression or biological activity can be any suitable reagent that can be used in a method for detection of biomarker expression or biological activity as described previously herein. Such reagents include, but are not limited to: a probe or primer, or a mixture of nucleic acids of the invention, that hybridizes under stringent hybridization conditions to a kinase biomarker or a fragment thereof (including to a biomarker-specific regulatory region in the biomarker-encoding gene); RT-PCR primers for amplification of mRNA encoding the biomarker or a fragment thereof; and/or an antibody or a mixture of antibodies of the invention, antigen-binding fragment thereof or other antigen-binding peptide that selectively binds to the biomarker.

The means for detecting a biomarker and/or a control marker of the assay kit of the present invention can be conjugated to a detectable tag or detectable label. Such a tag can be any suitable tag which allows for detection of the reagents used to detect the biomarker or control marker and includes, but is not limited to, any composition or label detectable by spectroscopic, photochemical, biochemical, immunochemical, electrical, optical or chemical means, as described herein and known in the art.

In addition, the means for detecting of the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly effecting the activity and/or ability of the detection means to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex), agarose, collagen and chitin. Exemplary inorganic supports include glass beads (porous and nonporous), stainless steel, metal oxides (e.g., porous ceramics such as ZrO.sub.2, TiO.sub.2, Al.sub.2O.sub.3, and NiO) and sand.

Other Applications

The invention provides a method for modulating one or more of growth, differentiation, or survival of a cell by modulating kinase expression or activity, e.g., by potentiating or disrupting certain protein-protein interactions. In general, whether carried out in vivo, in vitro, or in situ, the method comprises treating the cell with an effective amount of a kinase peptide, a nucleic acid, or an antibody of the invention, at least one of (i) rate of growth, (ii) differentiation, or (iii) survival of the cell. The modulatory effect as described are useful for researches on signal transduction pathways, as well as disease treatment.

The invention provides an antisense nucleic acid that specifically hybridizes to a nucleic acid encoding a kinase of the present invention, wherein the antisense nucleic acid inhibits the expression of the kinase. The invention further provides a method of inhibiting the expression of a kinase of the present invention by contacting a sample in vitro, or in vivo, with an antisense nucleic acid of the present invention so that expression of the kinase is inhibited.

In another aspect, an antibody of the present invention may bind to and competitively inhibit polypeptide multimerization and/or binding of a kinase of the invention to a ligand, thus modulate the activity of the kinase in signal transduction.

In one embodiment, an RTK-Mab, MAPKAP-K-Mab, or PI3 kinase-MAb, upon binding to the corresponding kinase located on a cell membrane, induces apoptosis in the cell expressing the corresponding kinase on its membrane. The MAb may also reduce the number of cells, or inhibits cell growth of cells that express corresponding kinase (kinase-expressing cells). Preferably, the reduction in cell number or inhibition of cell growth is by at least about 10%, about 20%, about 30%, about 40%, about 50%, about 65%, about 75%, or greater. Preferably, the kinase-expressing cells are disease cells, e.g., cancer or tumor cells. More preferably, the cancers include but are not limited to, colorectal cancer, pancreatic cancer, lung cancer, gastric cancer, hepatocellular carcinoma, breast cancer and thyroid cancer.

The MAb may also inhibit the proliferation of kinase-expressing cells, preferably by at least about 10%, about 20%, about 30%, about 40%, about 50%, about 65%, about 75%, or greater. In another embodiment, the MAb inhibits the cell growth of the kinase-expressing cells, preferably by at least about 10%, about 20%, about 30%, about 40%, about 50%, about 65%, about 75%, or greater. Preferably, the kinase-expressing cells are disease cells, e.g., cancer or tumor cells. More preferably, the cancers include but are not limited to, colorectal cancer, pancreatic cancer, lung cancer, gastric cancer, hepatocellular carcinoma, breast cancer and thyroid cancer.

Therefore, antibodies of the present invention can act as agonists or antagonists of the protein tyrosine kinase biomarker polypeptides of the present invention. For example, the present invention includes antibodies which disrupt receptor/ligand interactions with polypeptides of the invention either partially or fully. The invention also includes receptor-specific antibodies which do not prevent ligand binding, but do prevent receptor activation. Receptor activation (i.e., signaling) can be determined by techniques described herein or as otherwise known in the art. For example, receptor activation can be determined by detecting the phosphorylation (e.g., on tyrosine or serine/threonine) of the receptor or its substrate by immunoprecipitation followed by Western Blot analysis.

Accordingly, the method can be carried out with kinase therapeutics such as a monoclonal antibody, an antisense nucleic acid, or a kinase peptide of the invention which agonizes or antagonizes the effects of signaling from a kinase protein or ligand binding of a kinase protein. The antisense nucleic acid of the invention inhibits the expression of a target kinase gene, while the peptide or the antibody may competitively inhibit ligand interactions with the wild-type kinase protein.

The kinase peptides of the present invention can be introduced together with a carrier protein, such as an albumin, to an animal system (such as rabbit or mouse). Alternatively, if the peptide is of sufficient length (e.g., at least about 15-25 amino acids), the polypeptide can be presented without a carrier.

In one embodiment, the composition for therapy is formulated for administration by intraperitoneal, intravenous, subcutaneous, and intramuscular injections, and other forms of administration such as oral, mucosal, via inhalation, sublingually, etc.

The nucleic acids and antibodies of the present invention may be delivered with a carrier. As used herein, the term "carrier" refers to a diluent, adjuvant, excipient, or vehicle with which an active ingredient, e.g., a nucleic acid, peptide or antibody of the invention is administered. Such carriers can be sterile liquids, such as water and oils. Water or aqueous solution, saline solutions and aqueous dextrose and glycerol solutions are preferably employed as carriers, particularly for injectable solutions. As used herein, a "pharmaceutically acceptable carrier" refers to a non-toxic material that does not interfere with the effectiveness of the biological activity of the active ingredient(s). A pharmaceutically acceptable carrier also refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The characteristics of the carrier will depend on the route of administration. Suitable pharmaceutical carriers are described in "Remington's Pharmaceutical Sciences" by E. W. Martin, 20th Edition.

A nucleic acid encoding any of the antibodies of the present invention can also be used for delivery and expression of any of the antibodies of the present invention in a desired cell. It is apparent that an expression vector can be used to direct expression of an antibody. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

The therapeutic polynucleotides and polypeptides of the present invention can be delivered using gene delivery vehicles. The gene delivery vehicle can be of viral or non-viral origin (see generally, Jolly (1994), Cancer Gene Therapy 1:51; Kimura (1994), Human Gene Therapy 5:845; Connelly (1985) Human Gene Therapy 1:185; and Kaplitt (1994), Nature Genetics 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242; alphavirus-based vectors, e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors, e.g., PCT Publication Nos. WO 94/12649, WO 93/03769; WO 93/19191; WO 94/28938; WO 95/11984 and WO 95/00655. Administration of DNA linked to killed adenovirus as described in Curiel (1992), Hum. Gene Ther. 3:147 can also be employed.

Non-viral delivery vehicles and methods can also be employed, including, but are not limited to, polycationic condensed DNA linked or unlinked to killed adenovirus alone (see, e.g., Curiel (1992), Hum. Gene Ther. 3:147); ligand-linked DNA (see, e.g., Wu (1989), J. Biol. Chem. 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes.

Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0 524 968. Additional approaches are described in Philip (1994), Mol. Cell. Biol. 14:2411 and in Woffendin (1994), Proc. Natl. Acad. Sci. 91:1581.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

In another embodiment, the present invention also contemplates administration of a composition comprising nucleic acids or antibodies of the present invention conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, or chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387; the disclosures of which are incorporated herein by reference in their entireties.

The dosage required for the treatment depends on the choice of the route of administration, the nature of the formulation, the nature of the subject's illness, the subject's size, weight, surface area, age and sex; other drugs being administered, and the judgment of the attending physician. Suitable dosages are in the range of 0.01-1000.0 mg/kg.

The practice of the present invention will employ, unless otherwise indicated, conventional techniques of cell biology, cell culture, molecular biology, microbiology, recombinant DNA, and immunology, which are within the skill of the art.

Such techniques are explained fully in the literature and herein above. See, for example, Molecular Cloning A Laboratory Manual, 2nd Ed., ed. by Sambrook, Fritsch and Maniatis (Cold Spring Harbor Laboratory Press: 1989); DNA Cloning, Volumes 1 and 11 (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. 1. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The invention will be better understood by reference to the following example which serve to illustrate but not to limit the present invention.

Example 1

Production and Characterization of pan-RTK Antibodies

SPF rabbits (Maine Biotechnology Services, Inc.) were used to generate polyclonal antisera. Forty (40) rabbits were used. Each rabbit was injected with a mixture of three pan-RTK epitopes, either combination #1 (YVHHRDLAAARNIL (SEQ ID NO. 1), CIHRRDLAARNNVL (SEQ ID NO. 2) and FVHRDLAAARNNCM (SEQ ID NO. 3) combination #1 is referred to as ("pan-TK1")) or combination #2 (LVHRDDLLAARNVL (SEQ ID NO. 4) FIHHRDIAAARNCL (SEQ ID NO. 5), and FVHRDDLATRNCCL (SEQ ID No. 6) combination #2 is referred to as ("pan-TK2")). The rabbits were bled, and the panRTK antisera were then affinity purified using the same combinations of epitopes against which they had been raised.

The purified pan-TK1 and pan-TK2 antisera were screened against the peptides used to raise the antibodies using ELISA and Western Blot assays.

The results of the ELISA assays for the pan-TK1 antisera are described below. ELISA assays were performed using the following BSA-conjugated peptides (one assay per peptide):

```
Sequence 2 peptide:
Ac-YVHHRDLAAARNIL-OH        (SEQ ID NO. 1)

Sequence 3 peptide:
H₂N-CIHRRDLAARNNVL-amide    (SEQ ID NO. 2)

Sequence 4 peptide:
Ac-FVHRDLAAARNNCM-OH        (SEQ ID NO. 3)
```

ELISA Results for Sequence 2

Assay Parameters:

| Step | Reagent | Serial dilution | Dilution buffer | Concentration | Volume/vile | Incubation |
|---|---|---|---|---|---|---|
| Ag coating | Pan-TK1 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.18 | 0.01 | 0.105 | 0.019 | 0.06 | 0.02 | 0.064 | 0.013 | 0.053 | 0.02 | 0.047 | 0.02 |
| Pre-bleed Rb2 | B | 0.2 | 0.01 | 0.112 | 0.019 | 0.07 | 0.02 | 0.058 | 0.019 | 0.052 | 0.02 | 0.045 | 0.1 |
| Rb 1 Tb 7/23 | C | 0.71 | 0.03 | 1.262 | 0.035 | 1.11 | 0.03 | 0.95 | 0.021 | 0.361 | 0.03 | 0.148 | 0.03 |
| Rb 2 Tb 7/23 | D | 0.76 | 0.02 | 1.111 | 0.029 | 0.93 | 0.03 | 0.711 | 0.024 | 0.33 | 0.03 | 0.021 | 0.03 |

The results are shown graphically in FIG. 1. The first two bars represent sera taken from test rabbits after administration of the peptides but prior to incubation (designated in FIG. 1 as pre-bleed Rb1 and Rb2). The second two bars represent antisera taken from the same test rabbits after incubation (designated in FIG. 1 as Rb1 Th 7/23 and Rb2 Th 7/23). As demonstrated in FIG. 1, the reactivity of the antisera to peptide sequence 2 (SEQ ID NO. 1) after incubation is several times greater than the reactivity of the control sera.

ELISA Results for Sequence 3

Assay Parameters:

| Step | Reagent | Serial dilution | Dilution buffer | Concentration | Volume/vile | Incubation |
|---|---|---|---|---|---|---|
| Ag coating | Pan-TK1 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.1 | 0.02 | 0.015 | 0.021 | 0.02 | 0.02 | 0.019 | 0.017 | 0.022 | 0.02 | 0.018 | 0.02 |
| Pre-bleed Rb2 | B | 0.4 | 0.03 | 0.022 | 0.026 | 0.02 | 0.02 | 0.023 | 0.021 | 0.023 | 0.02 | 0.025 | 0.03 |
| Rb 1 Tb 7/23 | C | 0.71 | 0.05 | 1.619 | 0.046 | 1.55 | 0.03 | 1.165 | 0.02 | 0.654 | 0.03 | 0.211 | 0.03 |
| Rb 2 Tb 7/23 | D | 0.9 | 0.04 | 1.576 | 0.044 | 1.55 | 0.03 | 1.129 | 0.028 | 0.68 | 0.03 | 0.231 | 0.03 |

Figure 2:
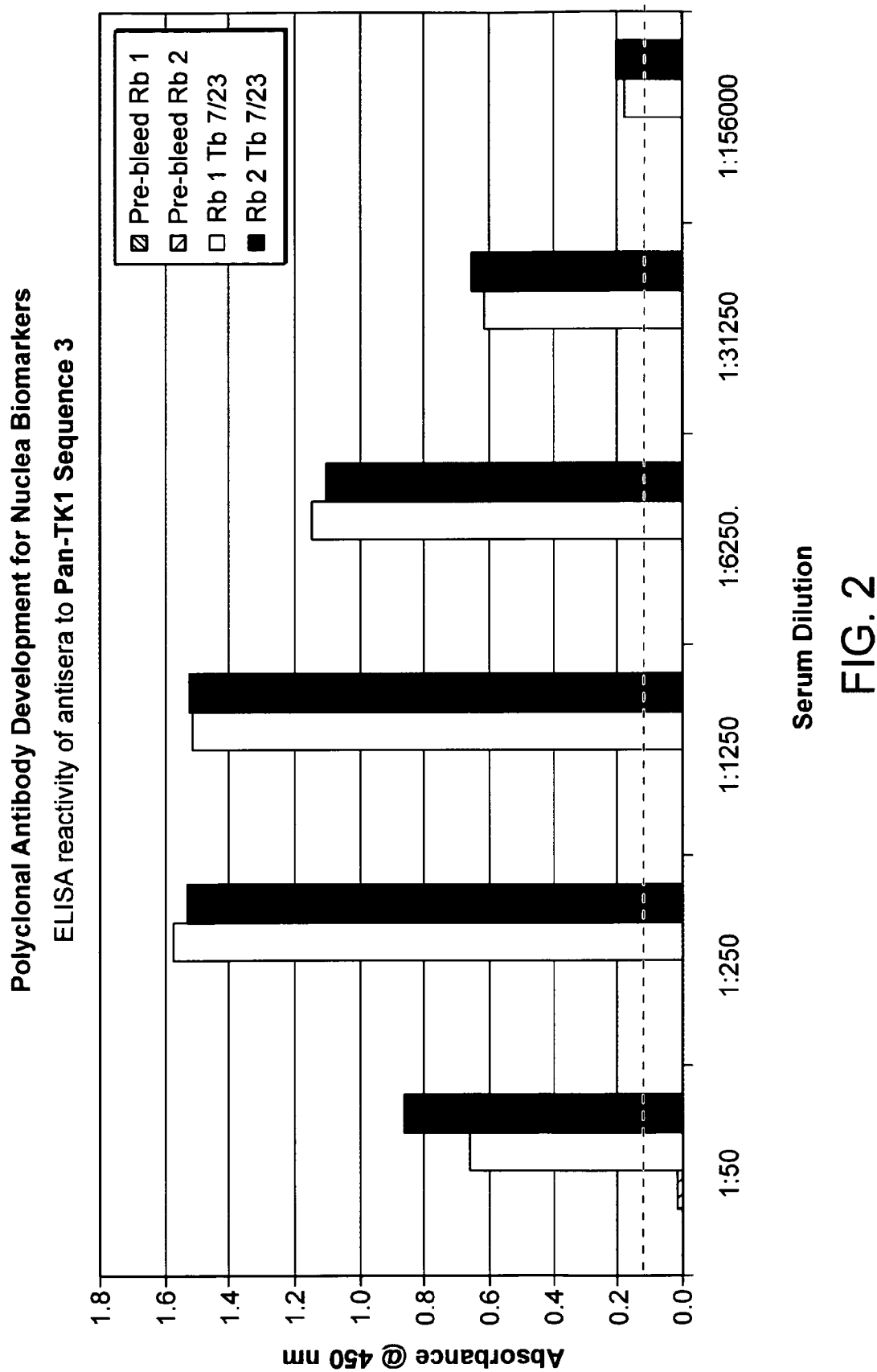
FIG. 2 is a graph showing the ELISA reactivity of polyclonal antisera pan-TK1 to kinase peptide sequence 3 (SEQ ID NO. 2) before and after incubation.

The results are shown graphically in FIG. 2. The first two bars represent sera taken from test rabbits after administration of the peptides but prior to incubation (designated in FIG. 2 as pre-bleed Rb1 and Rb2). The second two bars represent antisera taken from the same test rabbits after incubation (designated in FIG. 2 as Rb1 Tb 7/23 and Rb2 Tb 7/23). As demonstrated in FIG. 2, the reactivity of the antisera to peptide sequence 3 (SEQ ID NO. 2) afar incubation is several times greater than the reactivity of the control sera.

ELISA Results for Sequence 4

Assay Parameters:

| Step | Reagent | Serial dilution | Dilution buffer | Concentration | Volume/vile | Incubation |
|---|---|---|---|---|---|---|
| Ag coating | Pan-TK1 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.24 | 0.03 | 0.195 | 0.033 | 0.12 | 0.03 | 0.132 | 0.108 | 0.05 | 0.03 | 0.045 | 0.01 |
| Pre-bleed Rb2 | B | 0.24 | 0.04 | 0.179 | 0.036 | 0.12 | 0.19 | 0.063 | 0.03 | 0.05 | 0.03 | −0.12 | 0.04 |
| Rb 1 Tb 7/23 | C | 0.79 | 0.32 | 1.711 | 0.516 | 1.86 | 0.04 | 1.358 | 0.042 | 0.698 | 0.04 | 0.232 | −0 |
| Rb 2 Tb 7/23 | D | 0.88 | 0.04 | 1.529 | 0.54 | 1.48 | 0.03 | 1.181 | 0.036 | 0.38 | 0.04 | 0.158 | 0.04 |

Figure 3:
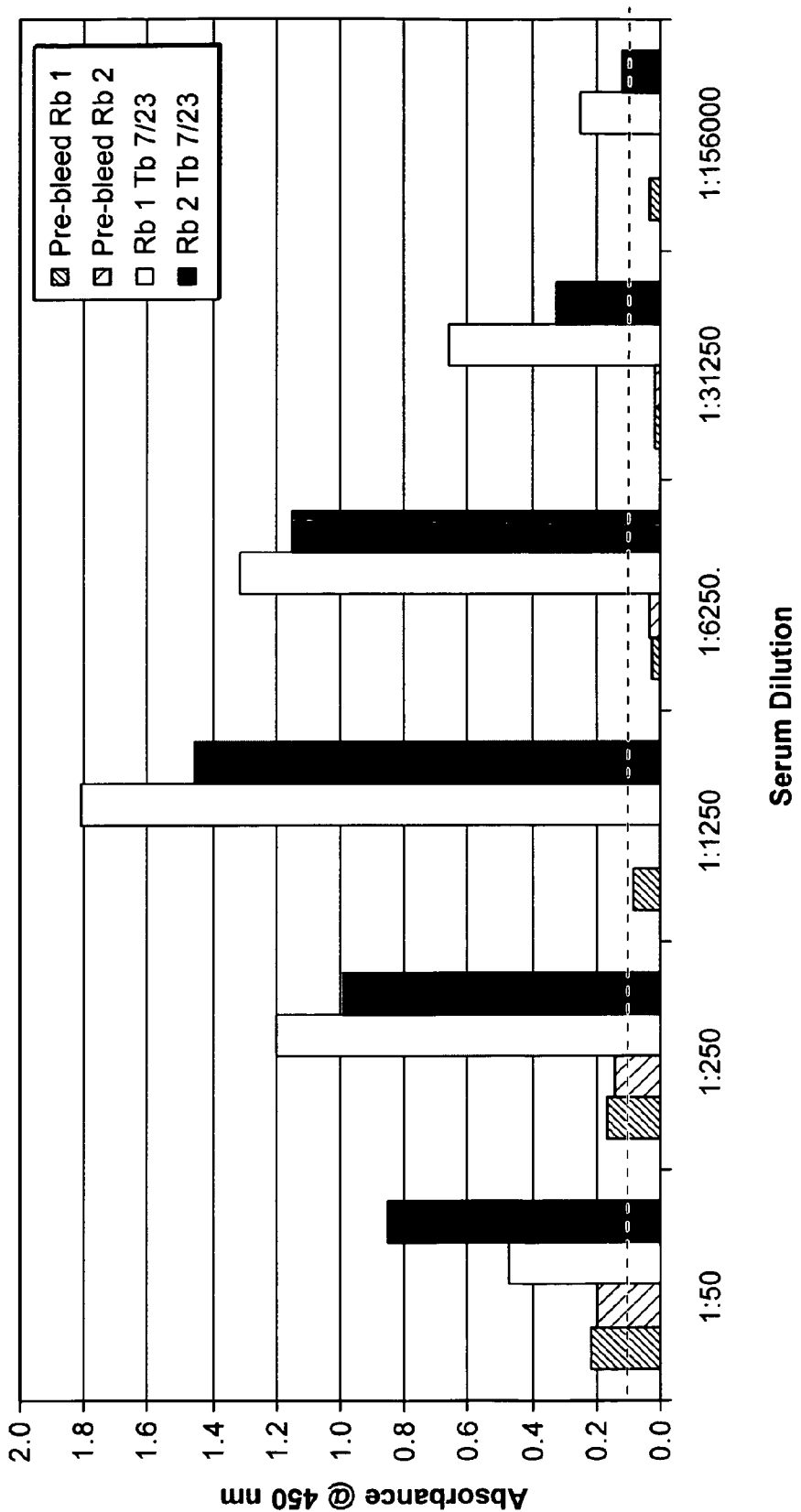
FIG. 3 is a graph showing the ELISA reactivity of polyclonal antisera pan-TK1 to kinase peptide sequence 4 (SEQ ID NO. 3) before and after incubation.

The results are shown graphically in FIG. 3. The first two bars represent sera taken from test rabbits after administration of the peptides but prior to incubation (designated in FIG. 3 as pre-bleed Rb1 and Rb2). The second two bars represent antisera taken from the same test rabbits after incubation (designated in FIG. 3 as Rb1 Tb 7/23 and Rb2 Tb 7/23). As demonstrated in FIG. 3, the reactivity of the antisera to peptide sequence 4 (SEQ ID NO. 3) after incubation is several times greater than the reactivity of the control sera.

Western Blot assays were run on rabbit antisera after inoculation with the pan-TK1 combination of peptides in order to confirm the antigenicity of the pan-TK1 peptides. The results of the Western Blot assays are described below.

Western Blot Report
Antibody: Rabbit serum test bleed Jul. 23, 2005
Antigen Sequence 2, Sequence 3 & Sequence 4

SDSPage Setup:

Percent Cross-linking of Polyacrylamide Gel: 4-20%
Antigen quantity per well: 2 µg
Molecular Weight Type: Precision Plus Kaleidoscope
Voltage Applied to the gel: 120 mA Transfer Setup (Gel to Membrane):

Membrane Type: PVDF
Voltage applied for the transfer: 100 V for 90 minutes

Blot Setup:

Blocking Buffer: 1% BSA
Concentration of primary antibody: 1:1000 dilution
Incubation time of detecting antibody: 30 minutes -continued Western Blot Report
Antibody: Rabbit serum test bleed Jul. 23, 2005
Antigen Sequence 2, Sequence 3 & Sequence 4

Figure 4A:
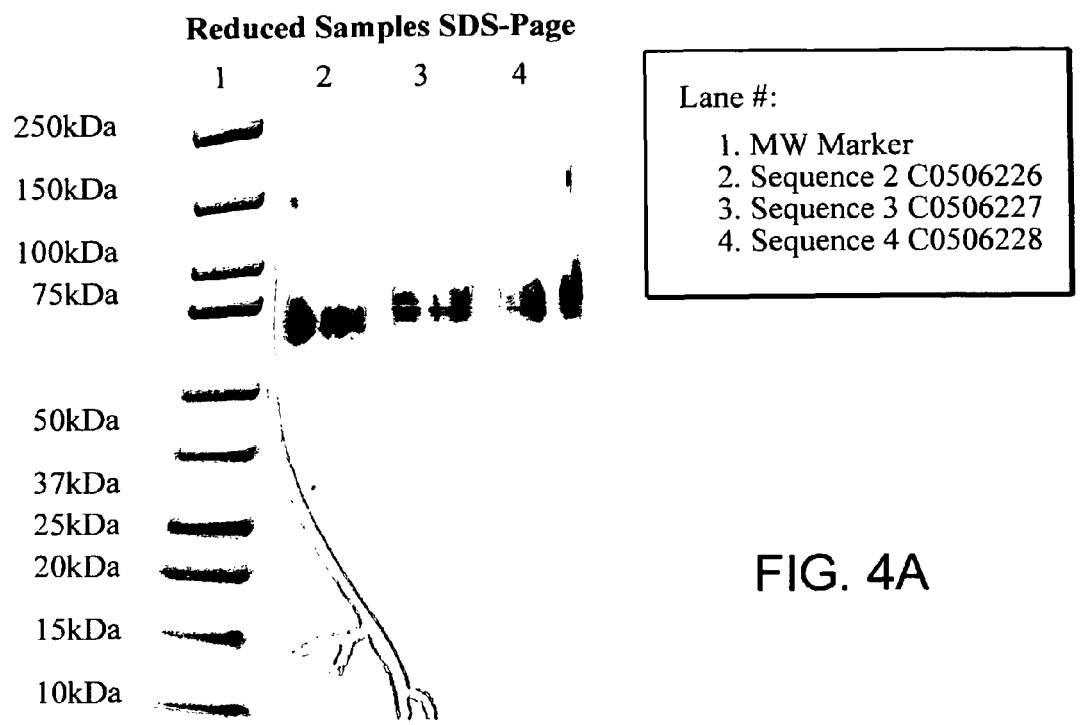
FIGS. 4a-d show the results of Western Blot assays confirming the antigenicity of kinase peptides 2, 3 and 4 in rabbit antisera, using the pan-TK1 antigen mixture as detection agent.
Figure 4B:
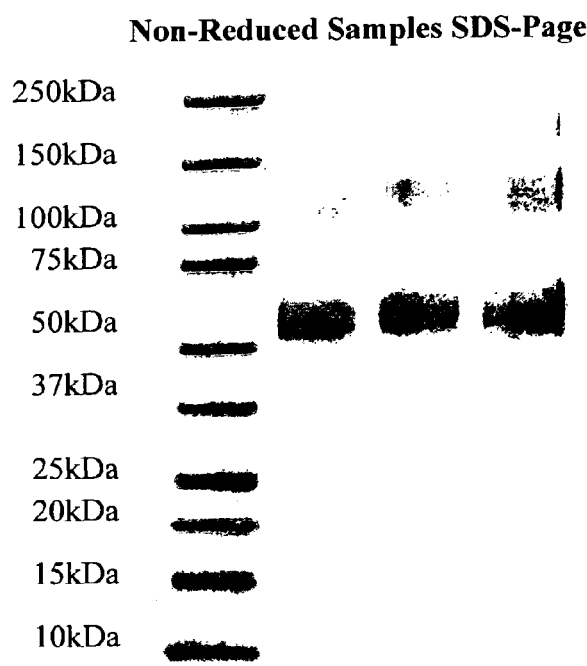
Figure 4C:
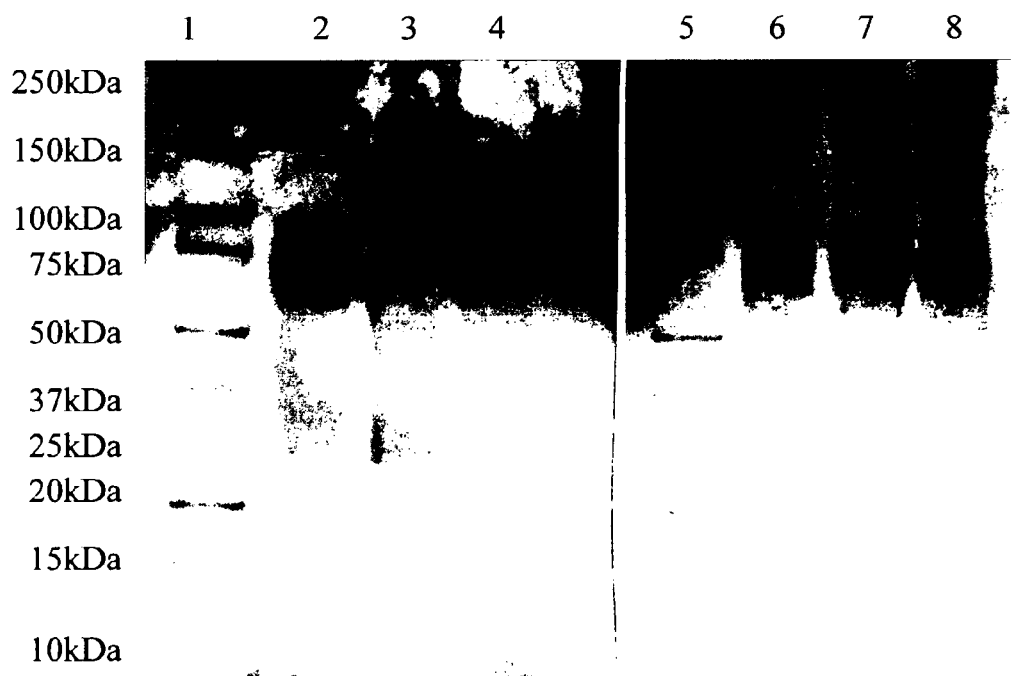
Figure 4D:
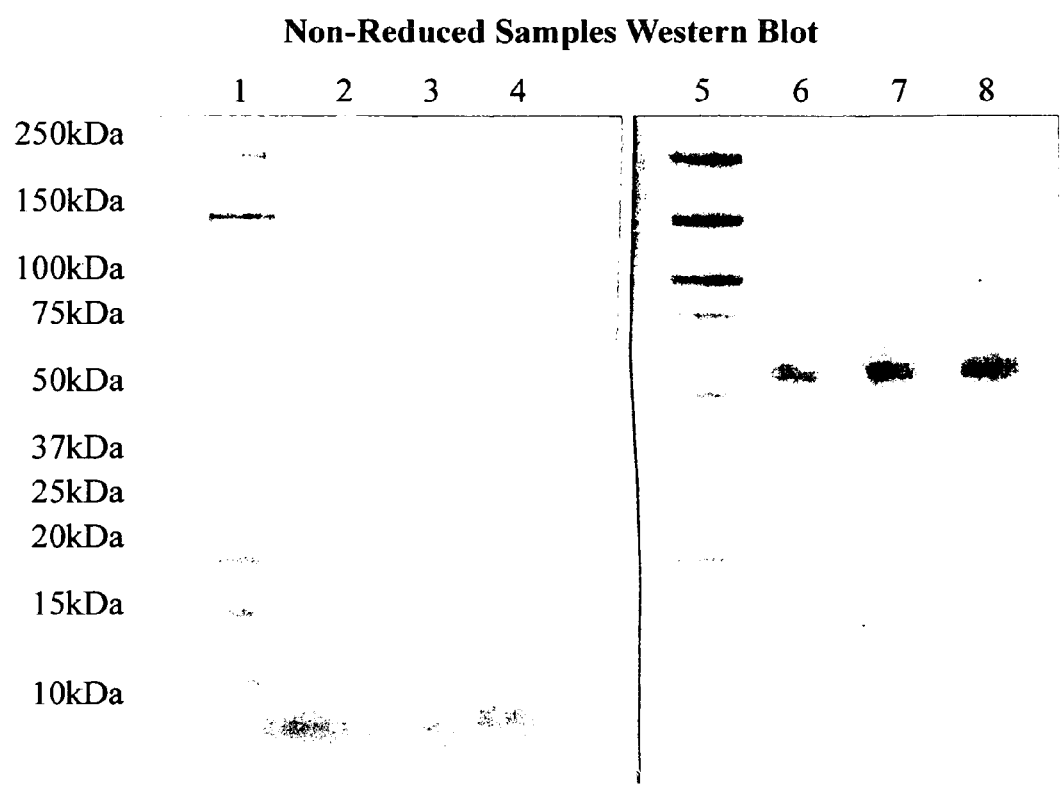

Tracer Type: Goat anti Rabbit (H&L) HRP
Incubation time of tracer: 30 minutes
Substrate Type: TMB Membrane
Development Time: 1 minute Rabbits were inoculated with the pan-TK1 mixture of peptides, and the rabbit antisera were assayed, using the pan-TK1 peptides as detection agents, at two time points: after inoculation but prior to incubation and two weeks after inoculation. The Western Blot results are shown in FIGS. 4a-d. FIGS. 4a and 4b show the initial results: FIG. 4a shows the results for reduced samples and FIG. 4b shows the results for non-reduced samples. For both FIGS. 4a and 4b, Lane 1 is a molecular weight marker, Lane 2 shows the antibody immunoreactive with sequence 2, Lane 3 shows the antibody immunoreactive with sequence 3, and Lane 4 shows the antibody immunoreactive with sequence 4. FIG. 4(c) shows the results after a two week incubation period for reduced samples, and FIG. 4(d) shows the results after two week incubation period for non-reduced samples of the rabbit antisera. For both FIGS. 4c and 4d, Lanes 1 and 5 are molecular weight markers, Lanes 2 and 6 show the antibody immunoreactive with sequence 2, Lanes 3 and 7 shows the antibody immunoreactive with sequence 3, and Lane 4 and 8 show the antibody immunoreactive with sequence 4.

The results of the ELISA assays for the pan-TK2 antisera are described. ELISA assays were performed using the following BSA-conjugated peptides (one assay per peptide): TABLE-US-00012 Sequence 5 peptide: Ac-LVHRDDL-LAARNVL-OH (SEQ ID NO. 4) Sequence 6 peptide: Ac-FIHHRDIAAARNCL-OH (SEQ ID NO. 5) Sequence 7 peptide: Ac-FVHRDDLATRNCCL-OH (SEQ ID NO. 6)

ELISA Results for Sequence 5

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.03 | 0.34 | 0.016 | 0.019 | 0.01 | 0.02 | 0.01 | 0.014 | 0.01 | 0.01 | 0.012 | 0.01 |
| Pre-bleed Rb2 | B | 0.15 | 0.09 | 0.045 | 0.045 | 0.02 | 0.03 | 0.016 | 0.019 | 0.013 | 0.02 | 0.01 | 0.02 |
| Rb 1 Tb 7/23 | C | 1.11 | 0.12 | 1.53 | 0.075 | 1.44 | 0.04 | 1.158 | 0.019 | 0.567 | 0.02 | 0.184 | 0.02 |
| Rb 2 Tb 7/23 | D | 0.54 | 0.02 | 0.627 | 0.07 | 0.46 | 0.02 | 0.175 | −0.079 | 0.22 | 0.02 | 0.145 | 0 |

Figure 5A:
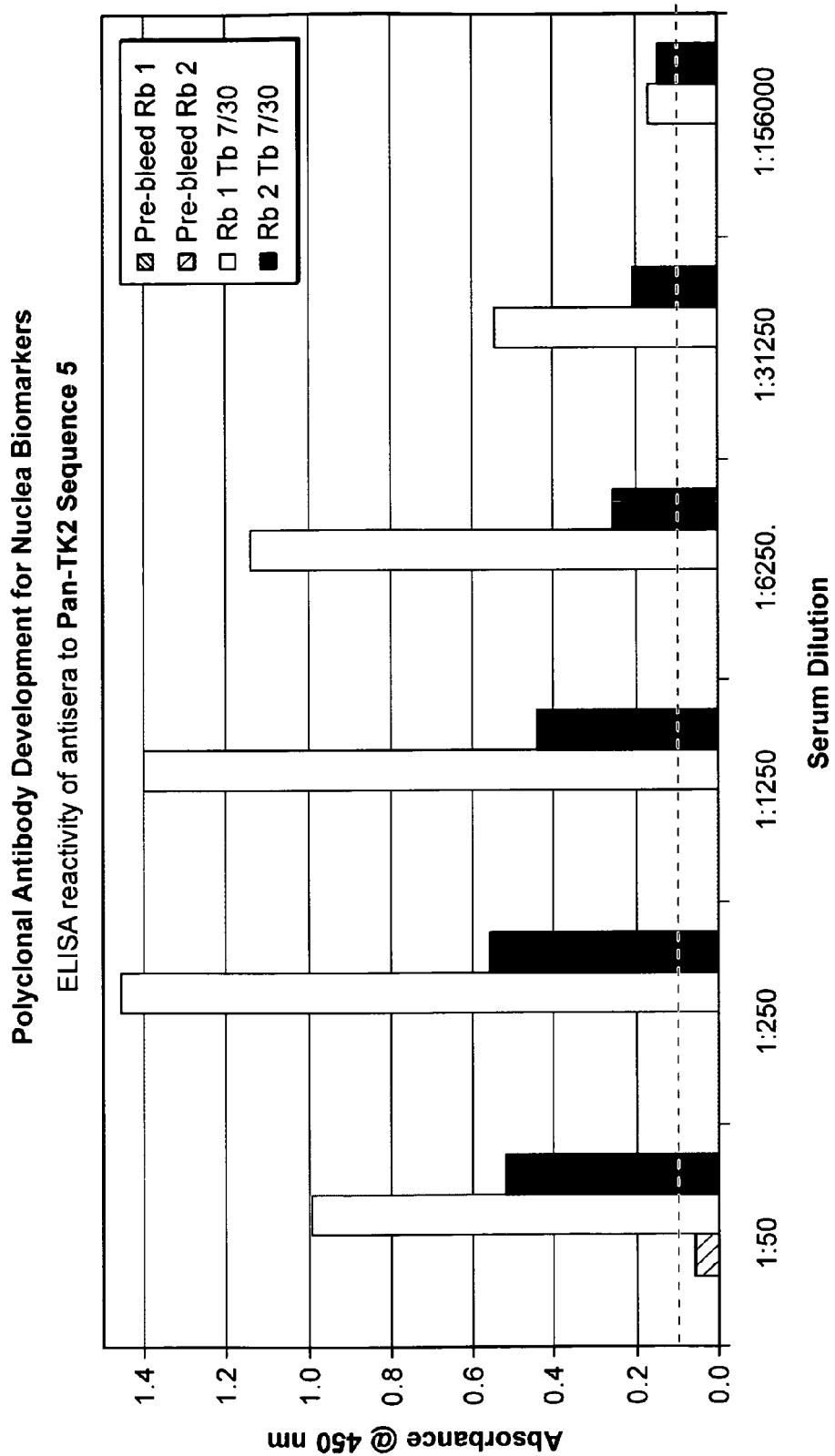
FIGS. 5a and 5b are graphs showing the ELISA reactivity of polyclonal antisera pan-TK2 to kinase peptide sequence 5 (SEQ ID NO. 4) before and after incubation.

The results are shown graphically in FIG. 5a. The first two bars represent sera taken from test rabbits after administration of the peptides but prior to incubation (designated in FIG. 5a as pre-bleed Rb1 and Rb2). The second two bars represent antisera taken from the same test rabbits after incubation (designated in FIG. 5a as Rb1 Th 7/30 and Rb2 Th 7/30). As demonstrated by the results shown in FIG. 5a, the reactivity of the antisera to peptide sequence 5 (SEQ ID NO. 4) after incubation is several times greater than the reactivity of the control sera.

ELISA Results for Sequence 5

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.02 | 0.02 | 0.017 | 0.02 | 0.02 | 0.02 | 0.034 | 0.018 | 0.02 | 0.02 | 0.02 | 0.02 |
| Pre-bleed Rb2 | B | 0.05 | 0.03 | 0.025 | 0.03 | 0.03 | 0.02 | 0.025 | 0.019 | 0.02 | 0.02 | 0.02 | 0.03 |
| Rb 1 Tb 7/23 | C | 0.67 | 0.05 | 0.768 | 0.06 | 0.8 | 0.04 | 0.648 | 0.024 | 0.32 | 0.02 | 0.12 | −0.1 |
| Rb 2 Tb 7/23 | D | 0.29 | 0.02 | 0.204 | 0.03 | 0.16 | 0.02 | 0.105 | 0.024 | 0.12 | 0.02 | 0.03 | 0.02 |
| Rb 1 Tb 8/20 | E | 0.55 | 0.03 | 0.891 | 0.04 | 0.96 | 0.03 | 0.881 | 0.027 | 0.54 | 0.03 | 0.2 | 0.02 |
| Rb 2 Tb 8/20 | F | 0.43 | 0.02 | 0.559 | 0.03 | 0.55 | 0.03 | 0.491 | 0.025 | 0.31 | 0.02 | 0.13 | 0.13 |

Figure 5B:
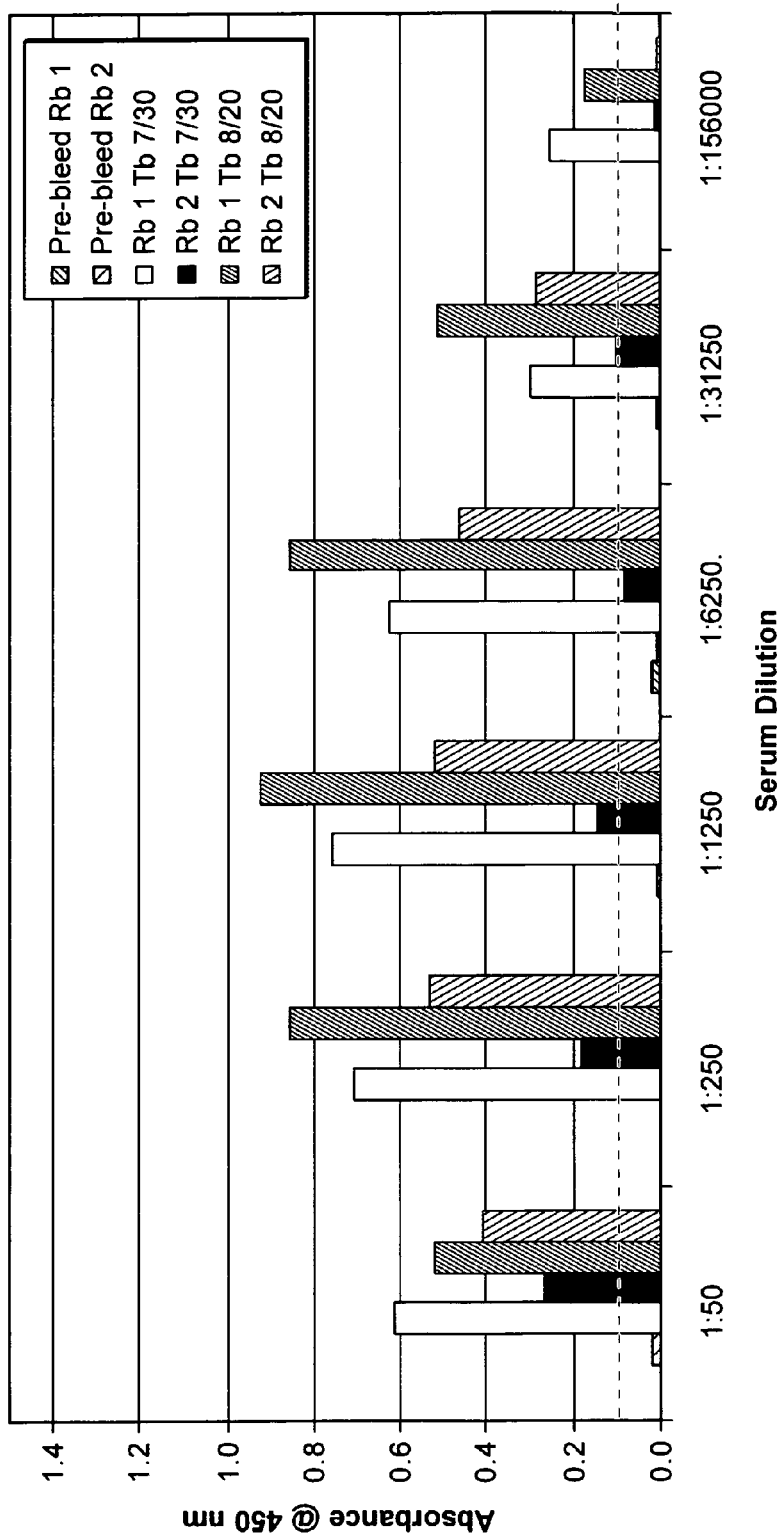

The results are shown graphically in FIG. 5b. The first two bars represent sera taken from test rabbits after administration of the peptides but prior to incubation (designated in FIG. 5b as pre-bleed Rb1 and Rb2). The second two bars represent antisera taken from the same test rabbits after incubation (designated in FIG. 5b as Rb1 Th 7/30 and Rb2 Th 7/30), and the final two bars represent antisera taken from the same rabbits at a later date (designated in FIG. 5b as Rb1 Th 8/20 and Rb2 Th 8/20). As demonstrated by the results shown in FIG. 5b, the reactivity of the antisera to peptide sequence 5 (SEQ ID No. 4) after incubation is several times greater than the reactivity of the control sera.

ELISA Results for Sequence 6

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | | |
|---|---|---|---|---|---|---|---|---|---|---|---|---|---|
| | | 1:50 | | 1:250 | | 1:1250 | | 1:6250 | | 1:31250 | | 1:156000 | |
| | | 1 | 2 | 3 | 4 | 5 | 6 | 7 | 8 | 9 | 10 | 11 | 12 |
| Pre-bleed Rb1 | A | 0.06 | 0.02 | 0.031 | 0.092 | 0.06 | 0.02 | 0.025 | 0.01 | 0.012 | 0.01 | 0.012 | 0.01 |
| Pre-bleed Rb2 | B | 0.07 | 0.03 | 0.021 | 0.009 | 0.05 | 0.02 | 0.045 | 0.016 | 0.013 | 0.02 | 0.01 | −0 |
| Rb 1 Tb 7/23 | C | 0.72 | 0.08 | 1.391 | 0.058 | 1.24 | 0.05 | 1.405 | 0.276 | 0.965 | 0.03 | 0.419 | 0.03 |
| Rb 2 Tb 7/23 | D | 0.52 | 0.3 | 0.808 | 0.019 | 0.61 | 0.02 | 0.336 | 0.017 | 0.142 | 0.02 | 0.054 | 0.08 |

Figure 6A:
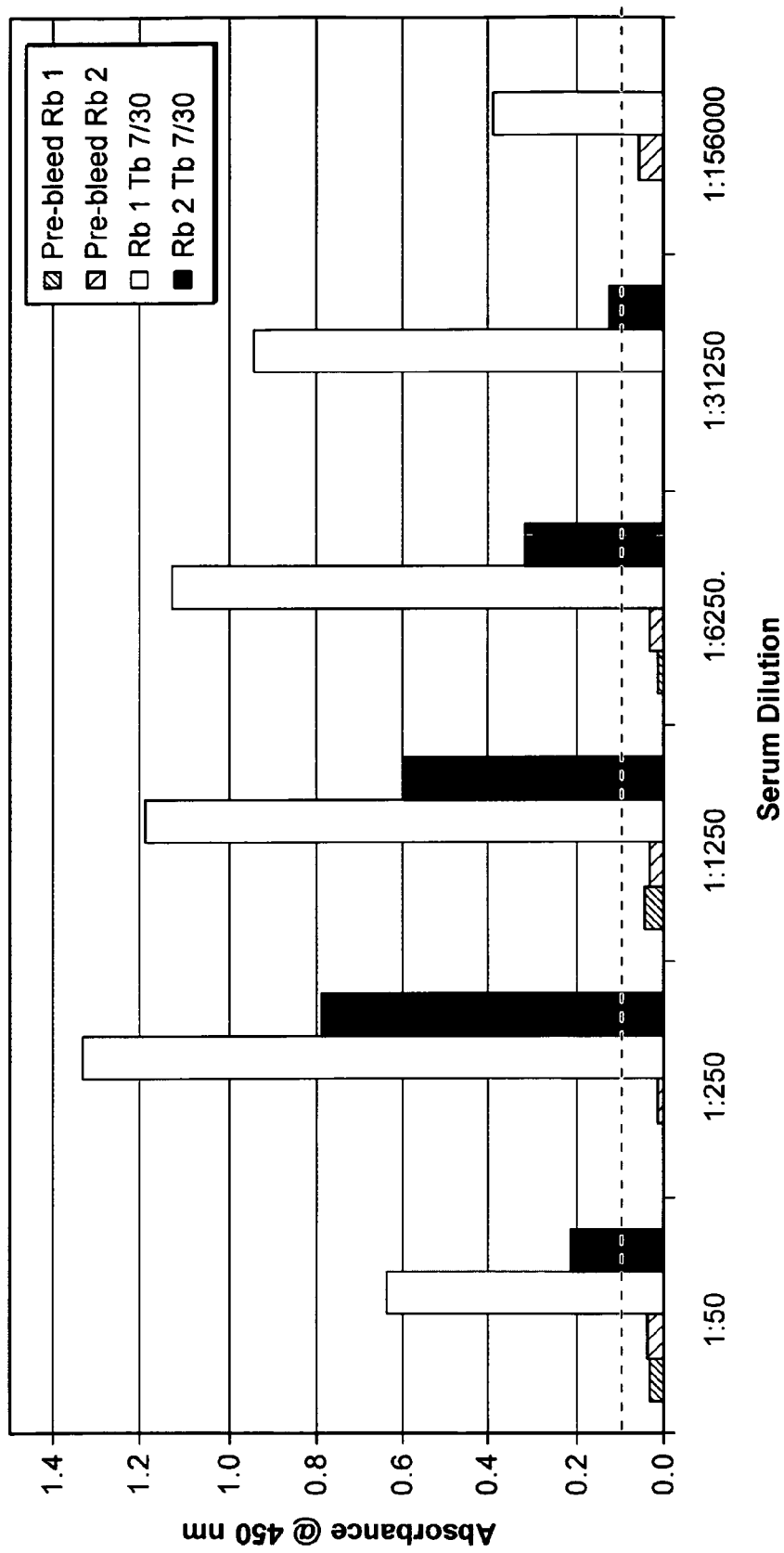
FIGS. 6a and 6b are graphs showing the ELISA reactivity of polyclonal antisera pan-TK2 to kinase peptide sequence 6 (SEQ ID NO. 5) before and after incubation.

The results are shown graphically in FIG. 6a. The first two bars represent sera taken from test rabbits after administration of the peptides but prior to incubation (designated in FIG. 6a as pre-bleed Rb1 and Rb2). The second two bars represent antisera taken from the same test rabbits after incubation (designated in FIG. 6a as Rb1 Th 7/30 and Rb2 Th 7/30). As demonstrated by the results shown in FIG. 6a, the reactivity of the antisera to peptide sequence 6 (SEQ ID NO. 5) after incubation is several times greater than the reactivity of the control sera.

ELISA Results for Sequence 6

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | | |
|---|---|---|---|---|---|---|---|---|---|---|---|---|---|
| | | 1:50 | | 1:250 | | 1:1250 | | 1:6250 | | 1:31250 | | 1:156000 | |
| | | 1 | 2 | 3 | 4 | 5 | 6 | 7 | 8 | 9 | 10 | 11 | 12 |
| Pre-bleed Rb1 | A | 0.05 | 0.02 | 0.01 | 0.02 | 0.04 | 0.02 | 0.02 | 0.01 | 0.05 | 0.02 | 0.03 | −0 |
| Pre-bleed Rb2 | B | 0.04 | 0.02 | 0.03 | 0.03 | 0.02 | 0.02 | 0.04 | 0.01 | 0.04 | 0.02 | 0.04 | 0.02 |

-continued

|  |  | Sample Dilution | | | | | | | | | | |
|---|---|---|---|---|---|---|---|---|---|---|---|---|
|  |  | 1:50 | | 1:250 | | 1:1250 | | 1:6250 | | 1:31250 | | 1:156000 |
|  |  | 1 | 2 | 3 | 4 | 5 | 6 | 7 | 8 | 9 | 10 | 11 | 12 |
| Rb 1 Tb 7/23 | C | 0.62 | 0.03 | 0.907 | 0.04 | 0.93 | 0.03 | 0.775 | 0.01 | 0.55 | 0.02 | 0.39 | 0.02 |
| Rb 2 Tb 7/23 | D | 0.32 | 0 | 0.241 | 0.03 | 0.24 | 0.02 | 0.296 | 0.01 | 0.32 | 0.03 | 0.3 | 0.02 |
| Rb 1 Tb 8/20 | E | 0.6 | 0.03 | 0.877 | 0.04 | 1.01 | 0.03 | 0.908 | 0.01 | 0.67 | 0.02 | 0.47 | 0.02 |
| Rb 2 Tb 8/20 | F | 0.49 | 0.04 | 0.658 | 0.03 | 0.66 | 0.02 | 0.512 | 0.01 | 0.4 | 0.02 | 0.33 | 0.02 |

Figure 6B:
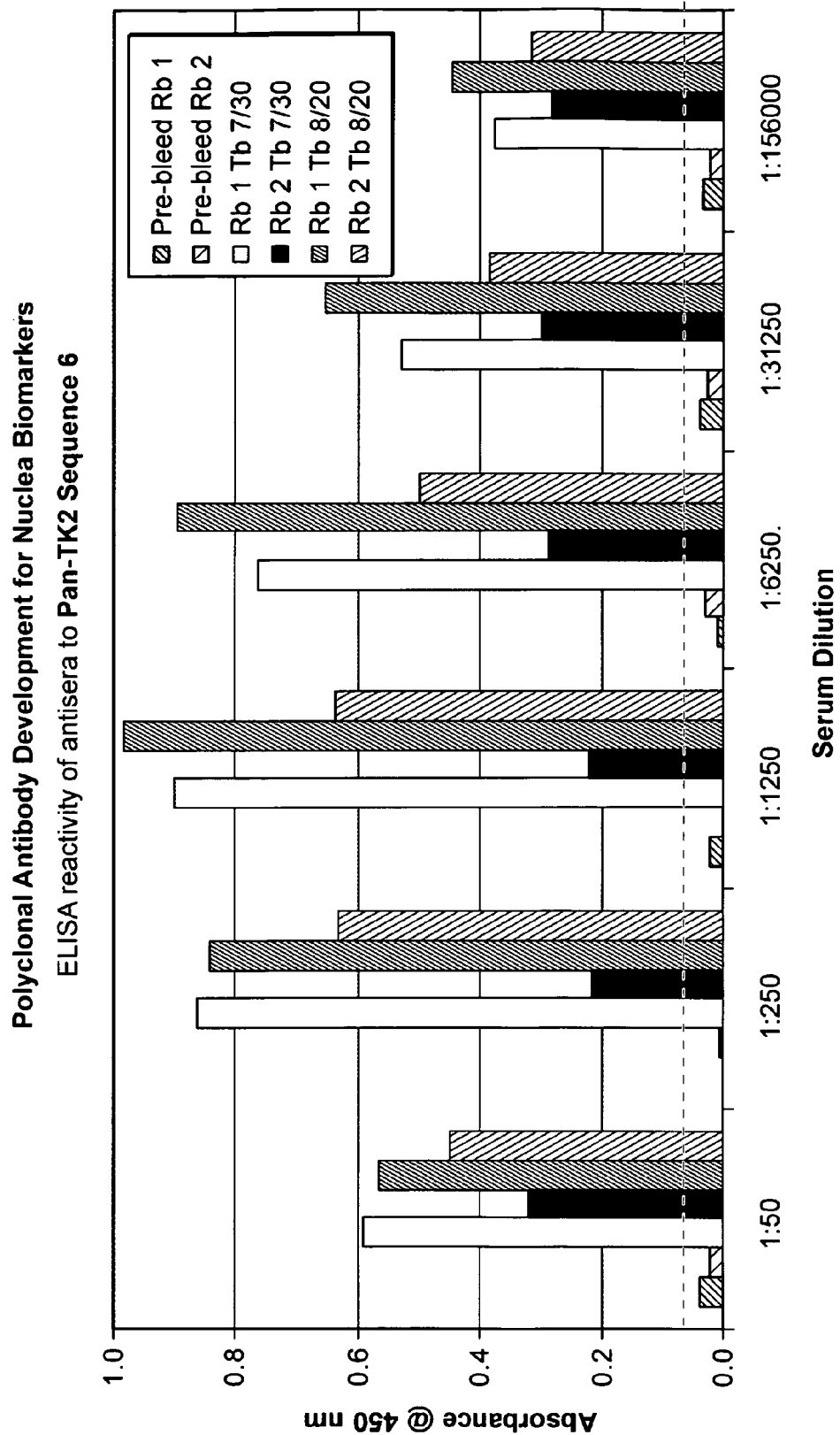

The results are shown graphically in FIG. 6b. The first two bars represent sera taken from test rabbits after administration of the peptides but prior to incubation (designated in FIG. 6b as pre-bleed Rb1 and Rb2). The second two bars represent antisera taken from the same test rabbits after incubation (designated in FIG. 6b as Rb1 Th 7/30 and Rb2 Th 7/30), and the final two bars represent antisera taken from the same rabbits at a later date (designated in FIG. 6b as Rb1 Th 8/20 and Rb2 Th 8/20). As demonstrated by the results shown in FIG. 6b, the reactivity of the antisera to peptide sequence 6 (SEQ ID No. 5) after incubation is several times greater than the reactivity of the control sera.

ELISA Results for Sequence 7

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

|  |  | Sample Dilution | | | | | | | | | | |
|---|---|---|---|---|---|---|---|---|---|---|---|---|
|  |  | 1:50 | | 1:250 | | 1:1250 | | 1:6250 | | 1:31250 | | 1:156000 |
|  |  | 1 | 2 | 3 | 4 | 5 | 6 | 7 | 8 | 9 | 10 | 11 | 12 |
| Pre-bleed Rb1 | A | 0.02 | 0 | 0.02 | 0.014 | 0.03 | 0.02 | 0.01 | 0.013 | 0.022 | 0.01 | 0.015 | 0.02 |
| Pre-bleed Rb2 | B | 0 | 0.02 | 0.03 | 0.024 | 0.05 | 0.02 | 0.02 | 0 | 0.013 | 0.01 | 0.03 | 0.09 |
| Rb 1 Tb 7/23 | C | 0.59 | 0.06 | 1.434 | 0.078 | 1.15 | 0.04 | 1.484 | −0.147 | 1.067 | 0.03 | 0.269 | 0.01 |
| Rb 2 Tb 7/23 | D | 0.46 | 0.3 | 0.441 | 0.014 | 0.41 | 0 | 1.234 | 0.018 | 0.085 | 0.02 | 0.088 | 0.08 |

Figure 7A:
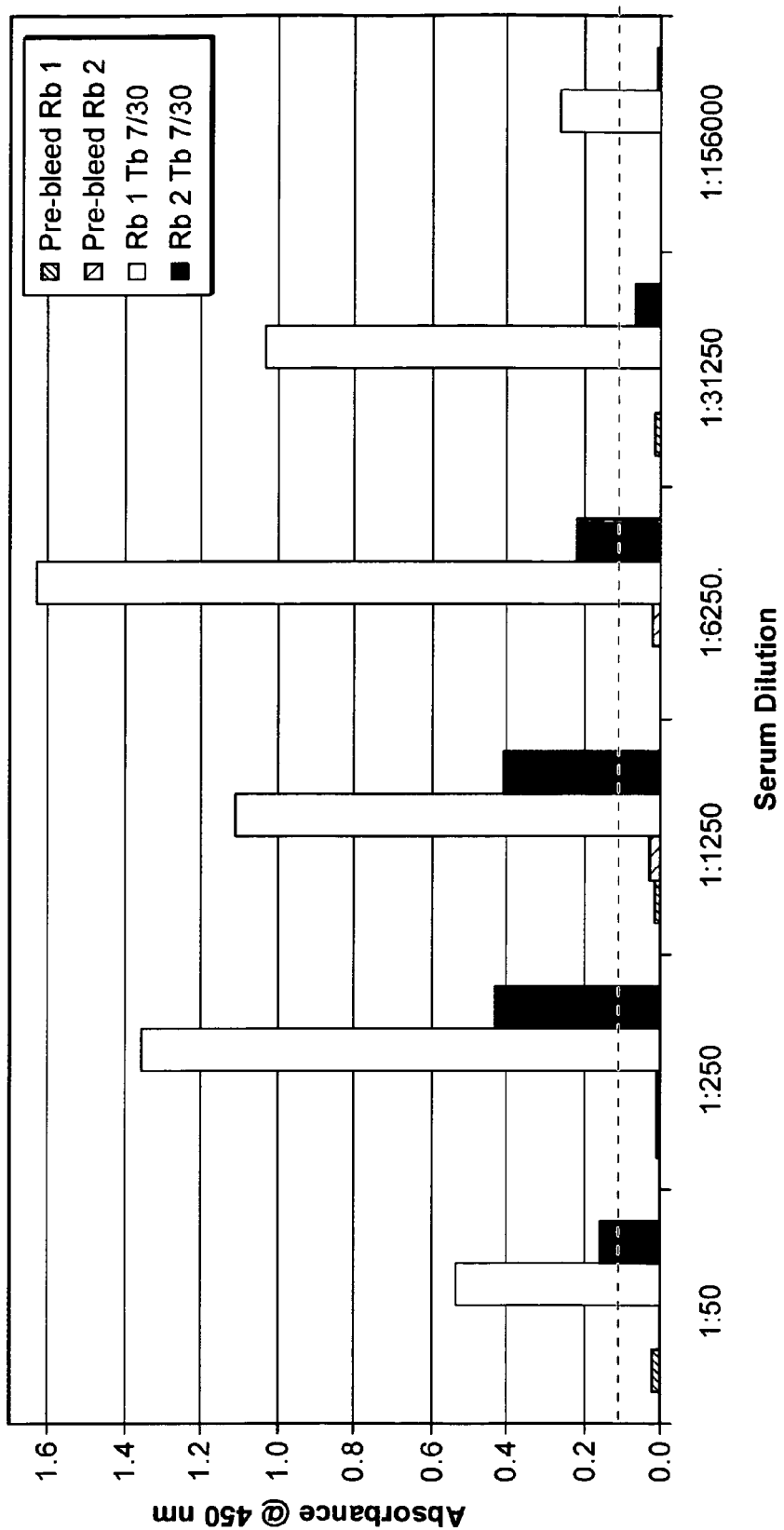
FIGS. 7a and 7b are graphs showing the ELISA reactivity of polyclonal antisera pan-TK2 to kinase peptide sequence 7 (SEQ ID NO. 6) before and after incubation.

The results are shown graphically in FIG. 7a. The first two bars represent sera taken from test rabbits after administration of the peptides but before incubation (designated in FIG. 7a as pre-bleed Rb1 and Rb2). The second two bars represent antisera taken from the same test rabbits after incubation (designated in FIG. 7a as Rb1 Tb 7/30 and Rb2 Tb 7/30). As demonstrated by the results shown in FIG. 7a, the reactivity of the antisera to peptide sequence 7 (SEQ ID NO. 6) after incubation is several times greater than the reactivity of the control sera.

ELISA Results for Sequence 7

Assay Parameters:

| Step | Reagent | Serial dilution | Dilution buffer | Concentration | Volume/vile | Incubation |
|---|---|---|---|---|---|---|
| Ag coating | Pan-TK2 | — | 0.15M PBS | 2. µg/mL | 50 µL | 1 hr @ 37 C. |
| Blocking | SeaBlock | — | — | NEAT | 300 µL | 30 min. @ 37 C. |
| Sample Dilution | see below | 5X | 0.15M PBS | starting @ 1:50 | 80 µL | 30 min. @ R.T. |
| Secondary Ab | anti-Rb HRP | — | 15M PBS w 0.05% Tween20 | 1:10000 | 50 µL | 30 min. @ R.T. |

Plate Design:

| | | Sample Dilution | | | | | | | | | | |
|---|---|---|---|---|---|---|---|---|---|---|---|---|
| | | 1:50 | | 1:250 | | 1:1250 | | 1:6250 | | 1:31250 | | 1:156000 |
| | | 1 | 2 | 3 | 4 | 5 | 6 | 7 | 8 | 9 | 10 | 11 | 12 |
| Pre-bleed Rb1 | A | 0.04 | 0.03 | 0.032 | 0.02 | 0.03 | 0.02 | 0.034 | 0.01 | 0.03 | 0.01 | 0.03 | 0.01 |
| Pre-bleed Rb2 | B | −0.2 | 0.07 | 0.057 | 0.04 | 0.04 | 0.37 | 0.03 | 0.014 | 0.04 | 0.02 | 0.03 | 0.02 |
| Rb 1 Tb 7/23 | C | 0.52 | −0 | 0.813 | 0 | 1.17 | −0.1 | 0.86 | 0.021 | 0.43 | 0.02 | 0.15 | 0.02 |
| Rb 2 Tb 7/23 | D | 0.3 | −0.3 | 0.298 | 0.02 | 0.23 | 0.02 | 0.131 | 0.014 | 0.06 | 0.02 | 0.04 | 0.01 |
| Rb 1 Tb 8/20 | E | 0.53 | 0.04 | 0.954 | 0.03 | 1.09 | 0.02 | 0.993 | 0.021 | 0.7 | 0.02 | 0.3 | 0.02 |
| Rb 2 Tb 8/20 | F | 0.48 | 0.02 | 0.789 | 0.02 | 0.74 | 0.02 | 0.507 | 0.015 | 0.21 | 0.02 | 0.13 | 0.02 |

Figure 7B:
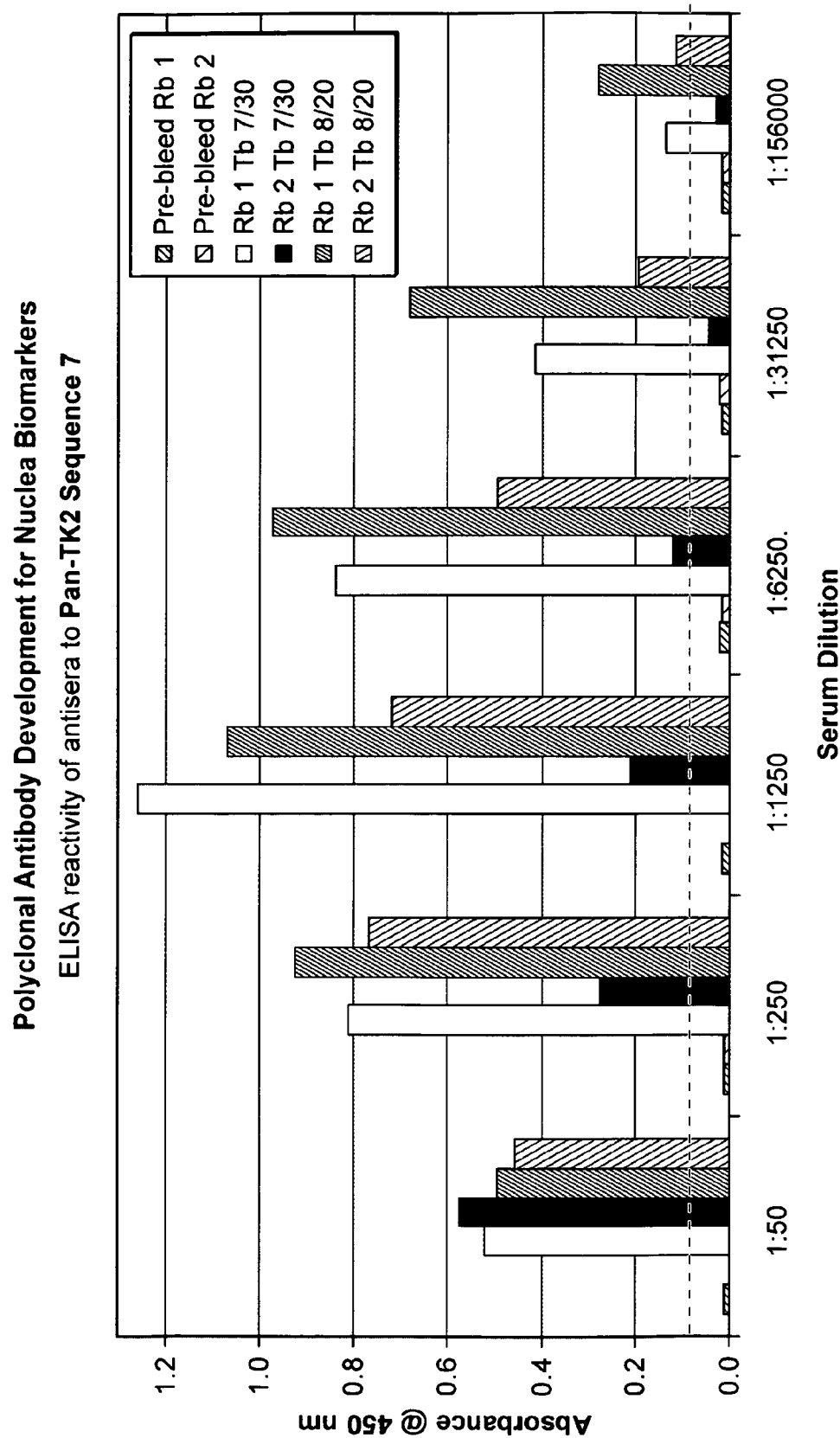

The results are shown graphically in FIG. 7b. The first two bars represent sera taken from test rabbits after administration of the peptides but prior to incubation (designated in FIG. 7b as pre-bleed Rb1 and Rb2). The second two bars represent antisera taken from the same test rabbits after incubation (designated in FIG. 7b as Rb1 Th 7/30 and Rb2 Th 7/30), and the final two bars represent antisera taken from the same rabbits at a later date (designated in FIG. 7b as Rb1 Th 8/20 and Rb2 Th 8/20). As demonstrated by the results shown in FIG. 7b, the reactivity of the antisera to peptide sequence 7 (SEQ ID No. 6) after incubation is several times greater than the reactivity of the control sera.

Western Blot assays were run on rabbit antisera after inoculation with the pan-TK2 combination of peptides in order to confirm the antigenicity of the pan-TK2 peptides. The results of the Western Blot assays are described below.

Western Blot Report
Antibody: Rabbit serum test bleed Aug. 20, 2005
Antigen Sequence 5, Sequence 6 & Sequence 7

Figure 8A:
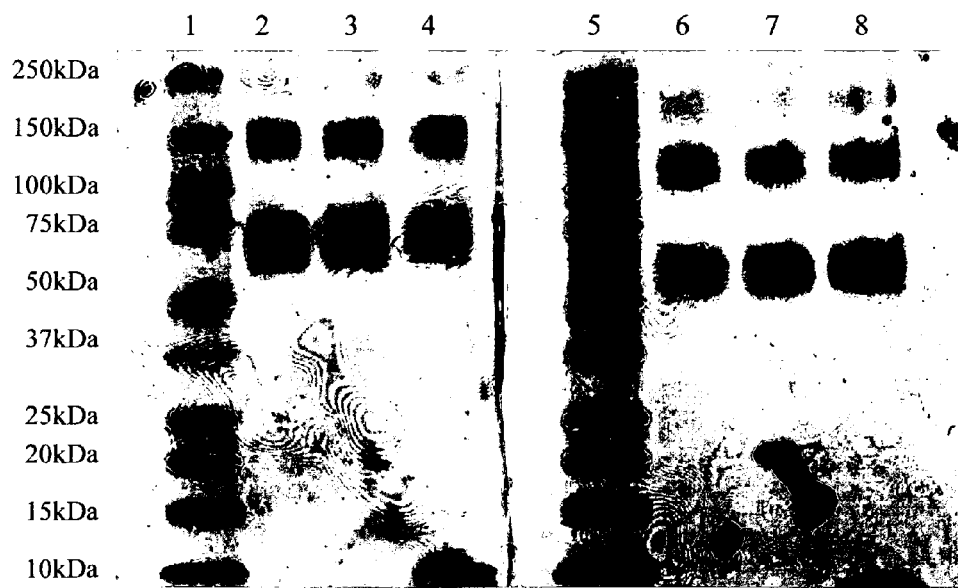
FIGS. 8a-c show the results of Western Blot assays confirming the antigenicity of kinase peptides 5, 6 and 7 in rabbit antisera, using the pan-TK2 antigen mixture as detection agent. Lanes 1-4 of FIG. 8a show the initial results after inoculation using reduced samples, and Lanes 5-8 of FIG. 8a show the initial results after inoculation using non-reduced samples.
Figure 8B:
Figure 8C:
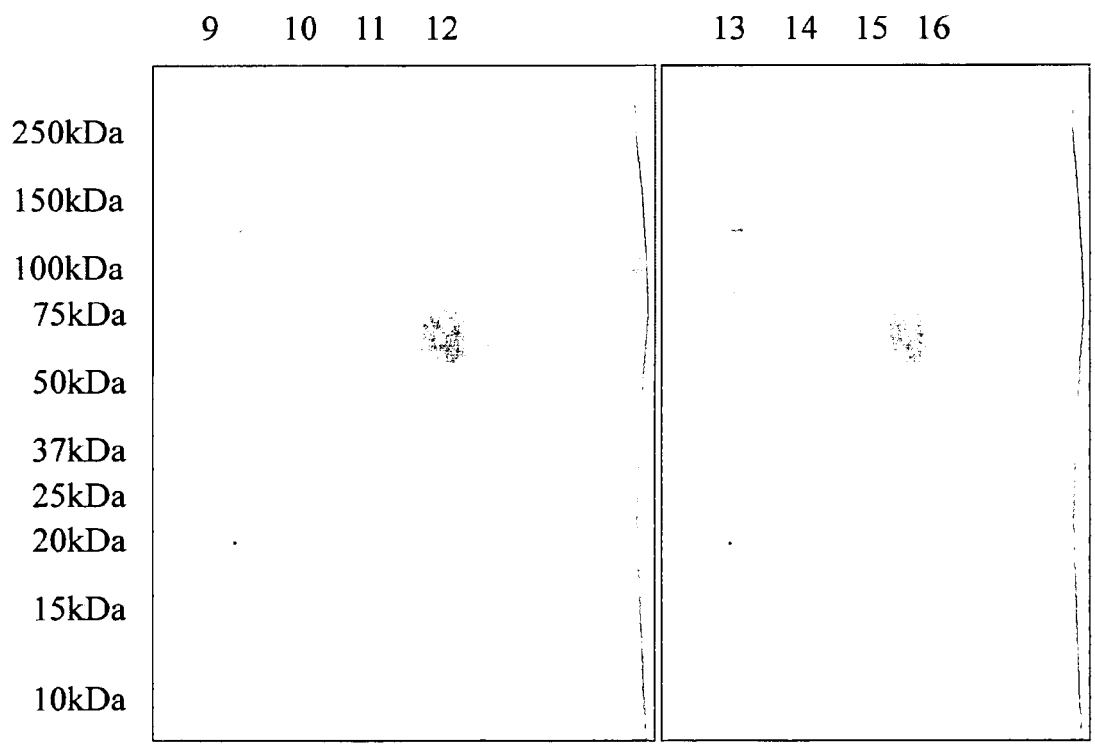

SDSPage Setup:

Percent Cross-linking of Polyacrylamide Gel: 4-20%
Antigen quantity per well: 2 μg
Molecular Weight Type: Precision Plus Kaleidoscope
Voltage Applied to the gel: 120 Ma
Transfer Setup (Gel to Membrane):

Membrane Type: PVDF
Voltage applied for the transfer: 100 V for 60 minutes
Blot Setup:

Blocking Buffer: 1% BSA
Concentration of primary antibody: 1:1000 dilution
Incubation time of detecting antibody: 30 minutes
Tracer Type: Goat anti Rabbit (H&L) HRP
Incubation time of tracer: 30 minutes
Substrate Type: TMB Membrane
Development Time: 1 minute Rabbits were inoculated with the pan-TK2 mixture of peptides, and the rabbit antisera were assayed, using the pan-TK2 antigens as detection agents, at two time points: after inoculation but prior to incubation, and two weeks after inoculation. The Western Blot results are shown in FIGS. 8a-c. FIG. 8a shows the initial results: Lanes 1-4 of FIG. 8a show the results for reduced samples and Lanes 5-8 of FIG. 8a show the results for non-reduced samples. For FIG. 8a, Lanes 1 and 5 are molecular weight markers, Lanes 2 and 6 show the antibody immunoreactive with sequence 5, Lanes 3 and 7 show the antibody immunoreactive with sequence 6, and Lanes 4 and 8 show the antibody immunoreactive with sequence 7.

FIG. 8b shows the results after a two week incubation period for reduced samples, and FIG. 8c shows the results after two week incubation period for non-reduced samples of the rabbit antisera. For both FIGS. 8b and 8c, Lanes 1 and 5 are molecular weight markers, Lanes 2 and 6 show the antibody immunoreactive with sequence 5, Lanes 3 and 7 shows the antibody immunoreactive with sequence 6, and Lane 4 and 8 show the antibody immunoreactive with sequence 7.

Example 2

Reactivity of the Pan-TK1 Antisera with Human Serum

Pan-TK1 antisera produced according to Example 1 was used to screen a human serum sample. The panTK antibodies in the antisera were able to simultaneously detect the relative phosphorylation of forty-two different RTK proteins in the serum sample. Table 5 below shows the proteins immunoreactive with the Pan-TK1 antisera.

TABLE 5

| Receptor | NCBI* |
|---|---|
| Axl | P30530 |
| Dtk | P55144 |
| PDGF R β | P02452 |
| EphA1 | NP 005223 |
| EphA2 | NP_004422 |
| EphA3 | NP_872585 |
| EphA4 | P54764 |
| EphA6 | P54758 |
| EphA7 | NP_004431 |
| EphB1 | NP 004432 |
| EphB2 | NP 004433 |
| EphB4 | NP 004435 |
| EphB6 | NP 004436 |
| ErbB2 | NP 004439 |
| ErbB3 | NP 001973 |
| ErbB4 | Q15303 |
| FGF R1 | NP 056934 |
| FGF R2 • | NP 002010 |
| FGF R3 | NM 022965 |
| FGF R4 | NM 022965 |
| Flt-3 | N 000750 |
| HGF R | Q04756 |
| IGF-1 R | NP 000609 |
| Insulin R | NP 034700 |
| M0CSF R | P07333 |
| Mer | Q12866 |
| MSP R | Q04912 |
| MuSK | NP 005583 |
| PDGF • | NP 006197 |
| PDFG R β | NP 002600 |
| c-Ret | P07949 |

TABLE 5-continued

| Receptor | NCBI* |
| --- | --- |
| ROR1 | Q01973 |
| ROR2 | Q01974 |
| SCF R | NP 954637 |
| Tie-1 | P35590 |
| Tie-2 | Q02763 |
| TrkA | P04629 |
| TrkB | Q16620 |
| TrkC | CAA12029 |
| VEGF R1 | NP 003367 |
| VEGF R2 | AAR26285 |
| VEGF R3 | P35916 |

*The numbers listed in the colums headed NCBI represent the NCBI protein accession numbers.

As shown by the results in Table 5, panRTK antibodies according to the invention are immunoreactive with most human and murine RTKs, and with a subset of nonreceptor tyrosine kinase proteins (e.g. JAK family members, SRC family members, FAK/PTK2, ABL, and ARG) that contain the conserved epitope. The panRTK antisera immunoprecipitate individual RTK proteins with lower efficiency than specific kinase antibodies, in as much as they react with the entire class of RTK proteins, rather than targeting a specific kinase protein. Typically, 10-20 μg of panRTK antisera are required per immunoprecipitation, in order to purify the same amount of each RTK protein that would typically be immunoprecipitated with 2-4 μg of an optimized, specific antibody.

Example 3

Production and Characterization of Anti-MAPKAP Antibodies

Polyclonal antisera containing antibodies against the five MAPKAP peptides shown as SEQ ID NOs. 7-11 were produced in rabbits according to the procedure set forth in Example 1. Each rabbit was injected with one of the peptides of SEQ ID NOs. 7-11. The rabbits were bled, and the antisera were then affinity purified using the same epitopes against which they had been raised.

Figure 9:
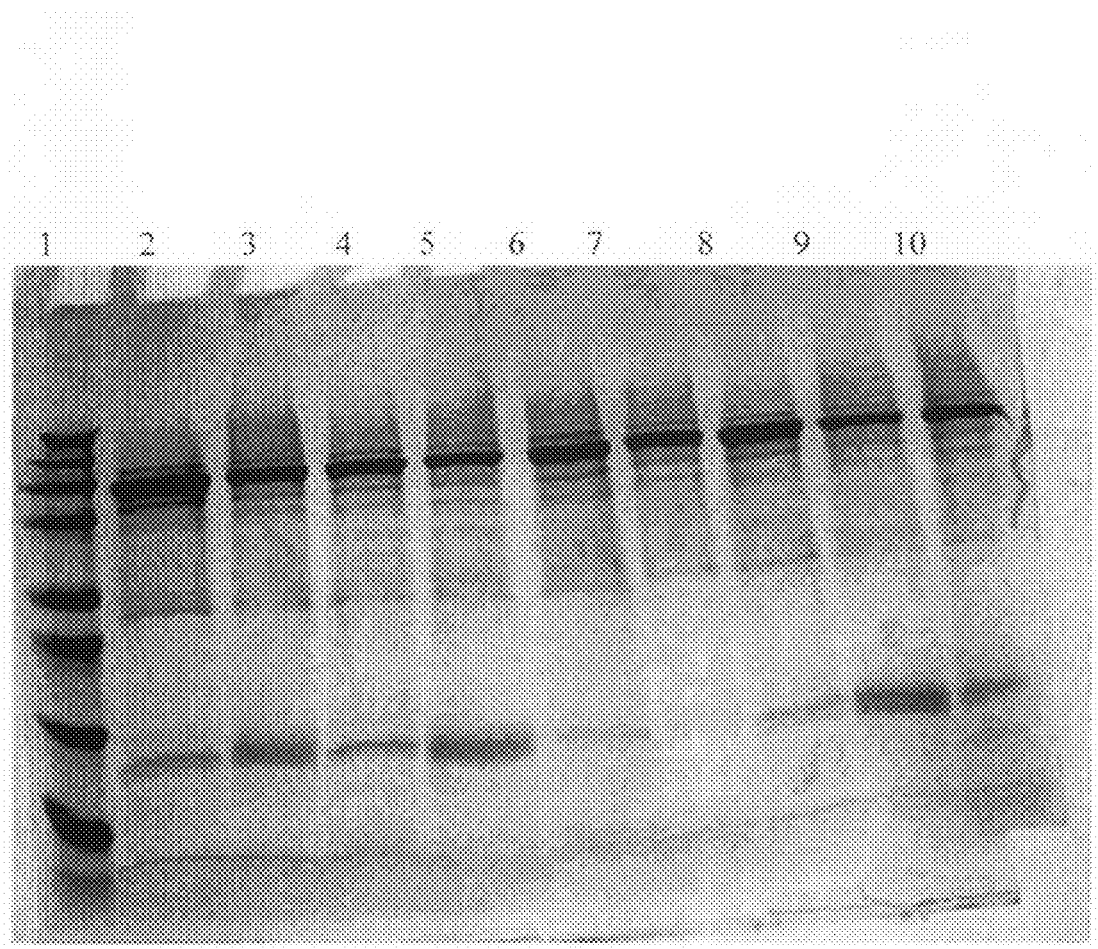
FIG. 9 shows the results of Western Blot assays confirming the antigenicity of antibodies raised against MAPKAP peptides SEQ ID NOs 7-11 in rabbit antisera, using the peptides of SEQ ID NOs. 7-11 as detection agents. Lane 1 is a reference ladder; Lane 2 shows the results for SEQ ID NO. 7; Lanes 3, 7 and 8 show the results for SEQ ID NO. 8; Lane 4 shows the results for SEQ ID NO. 9; Lane 5 shows the results for SEQ ID NO. 10; Lanes 6 and 9 show the results for SEQ ID NO. 11; and Lane 10 show the results for a commercial MAPK antibody used as a control.

The purified antisera were screened against the peptides used to raise the antibodies using ELISA and Western Blot assays as described in Example 1. Briefly, rabbits were inoculated with each of the peptides set forth as SEQ ID NOs. 7-11, and the rabbit antisera were assayed, using the peptides as detection agents. The Western Blot results at a dilutions of 1:50 are shown in FIG. 9: Lane 1 is a molecular weight marker, Lane 2 shows the antibody immunoreactive with SEQ ID NO. 7; Lanes 3, 7 and 8 show the antibody immunoreactive with SEQ ID NO. 8; Lane 4 shows the antibody immunoreactive with SEQ ID NO. 9; Lane 5 shows the antibody immunoreactive with SEQ ID NO. 10; Lanes 6 and 9 show the antibody immunoreactive with SEQ ID NO. 11; and Lane 10 shows the results for a commercial MAPK antibody obtained from Cell Signaling Technology (www.cellsignal.ccom) used as a control.

Figure 10A:
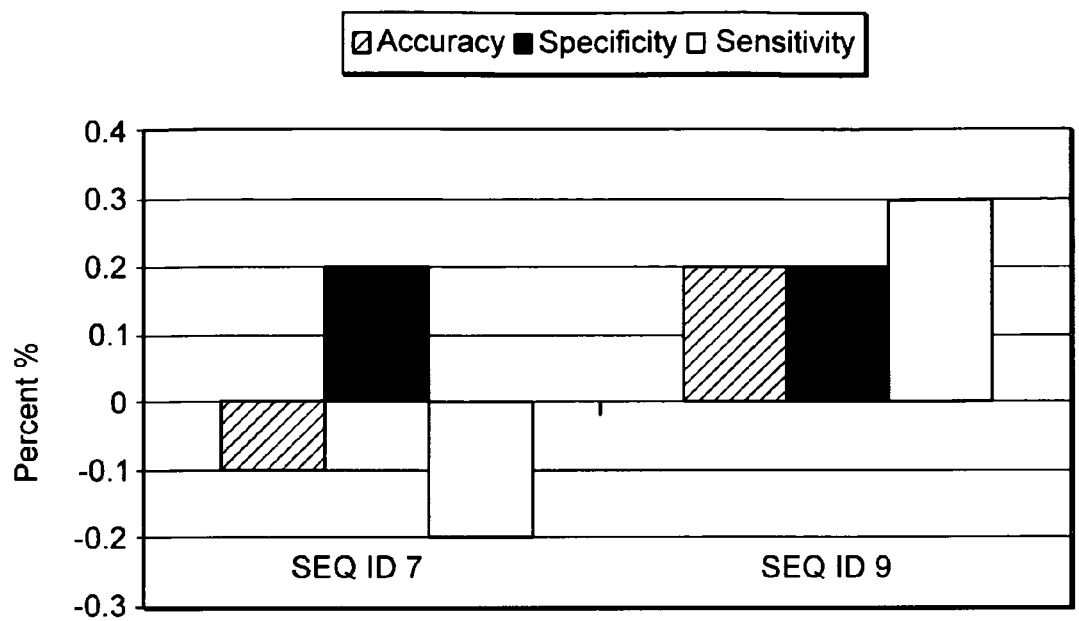
FIG. 10a shows the results for antibodies against SEQ ID NOs. 7 and 9 at dilutions of 1:50.
Figure 10B:
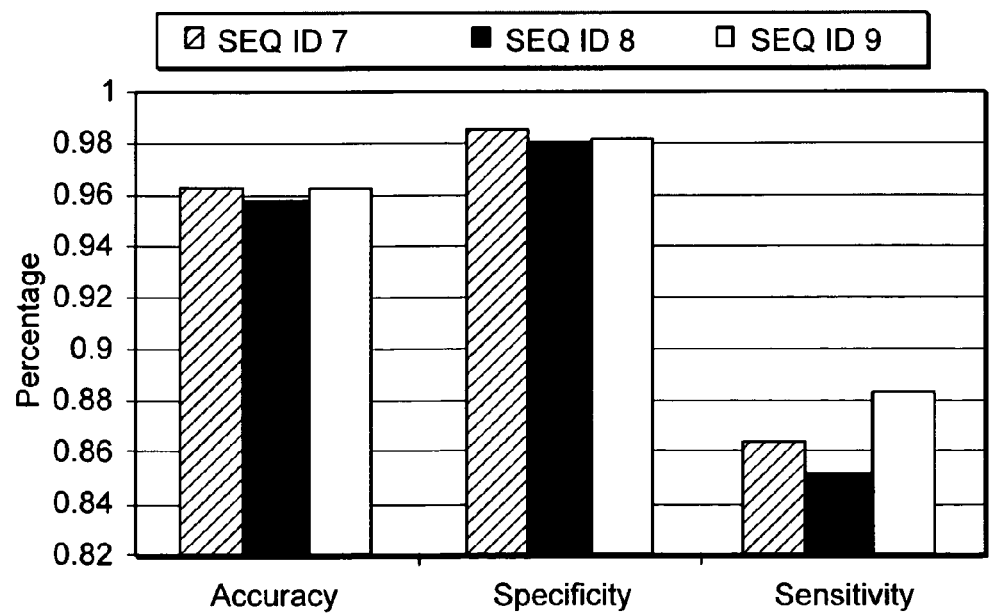
FIG. 10b shows the results for the antibodies against SEQ ID NOs. 7, 8 and 9 at dilutions of 1:250.
Figure 10C:
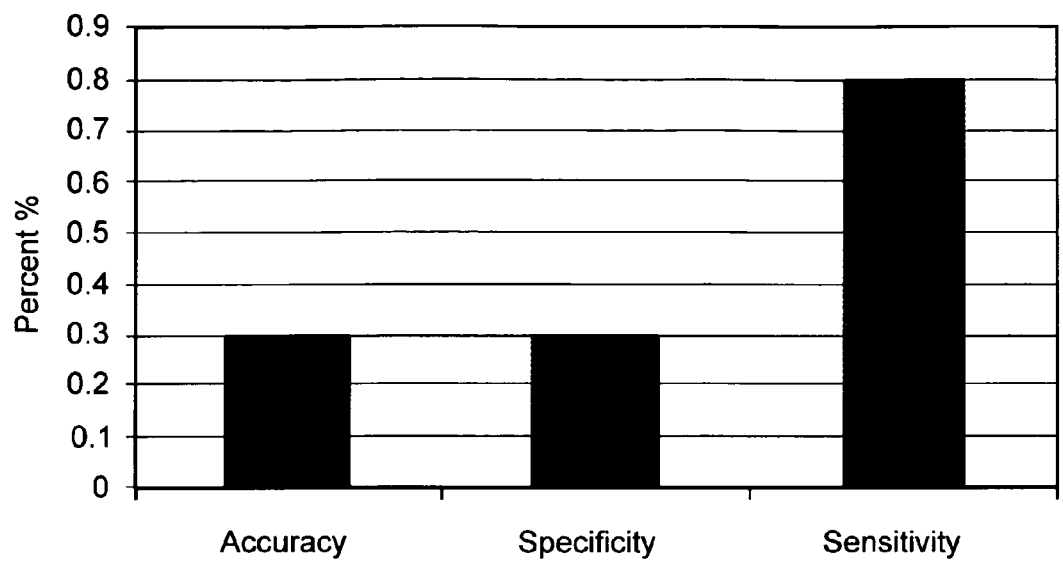
FIG. 10c shows the results for antibodies against SEQ ID NO. 11 at a dilution of 1:250.

The results of the ELISA assays for the antisera are shown schematically in FIGS. 10a-c. ELISA assays were performed using the following BSA-conjugated peptides (one assay per peptide) at dilutions of 1:50 and 1:250. The accuracy, specificity and sensitivity of the antibodies were measured using standard MS techniques. FIG. 10a is a graph showing the results for the antibodies against the peptides of SEQ ID. NOs. 7 and 9 at a dilution of 1:50; FIG. 10b shows the results for the antibodies against SEQ ID NOs. 7, 8 and 9 at dilutions of 1:250; and FIG. 10c shows the results for the antibody against SEQ ID NO. 11 at a dilution of 1:250. The ELISA assay results showed that the antibody against SEQ ID NO. 7 displayed positive sensitivity, and the antibodies against SEQ ID NOs. 8-11 all showed positive accuracy, specificity and sensitivity.

Example 4

Production and Characterization of Anti-PI3 Antibodies

Polyclonal antisera containing antibodies against the twelve PI3 peptides shown as SEQ ID NOs. 12-23 were produced in rabbits according to the procedure set forth in Example 1. Each rabbit was injected with one of the peptides of SEQ ID NOs. 12-23. The rabbits were bled, and the antisera were then affinity purified using the same epitopes against which they had been raised.

Figure 12A:
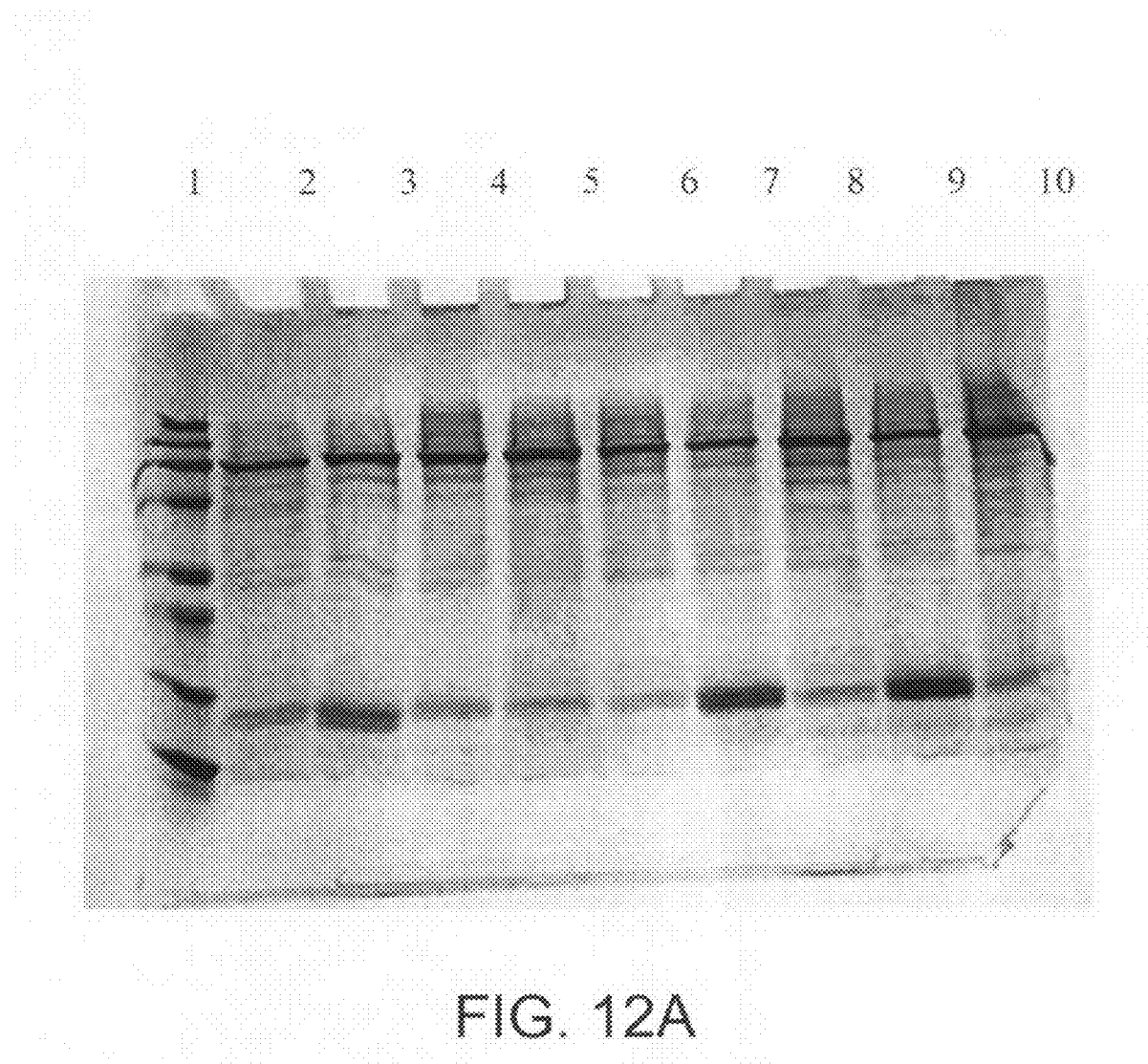
FIGS. 12a-b show the results of Western Blot assays confirming the antigenicity of antibodies raised against PI3 peptides SEQ ID NOs 12-23 in rabbit antisera, using the peptides of SEQ ID NOs. 12-23 as detection agents.
Figure 12B:
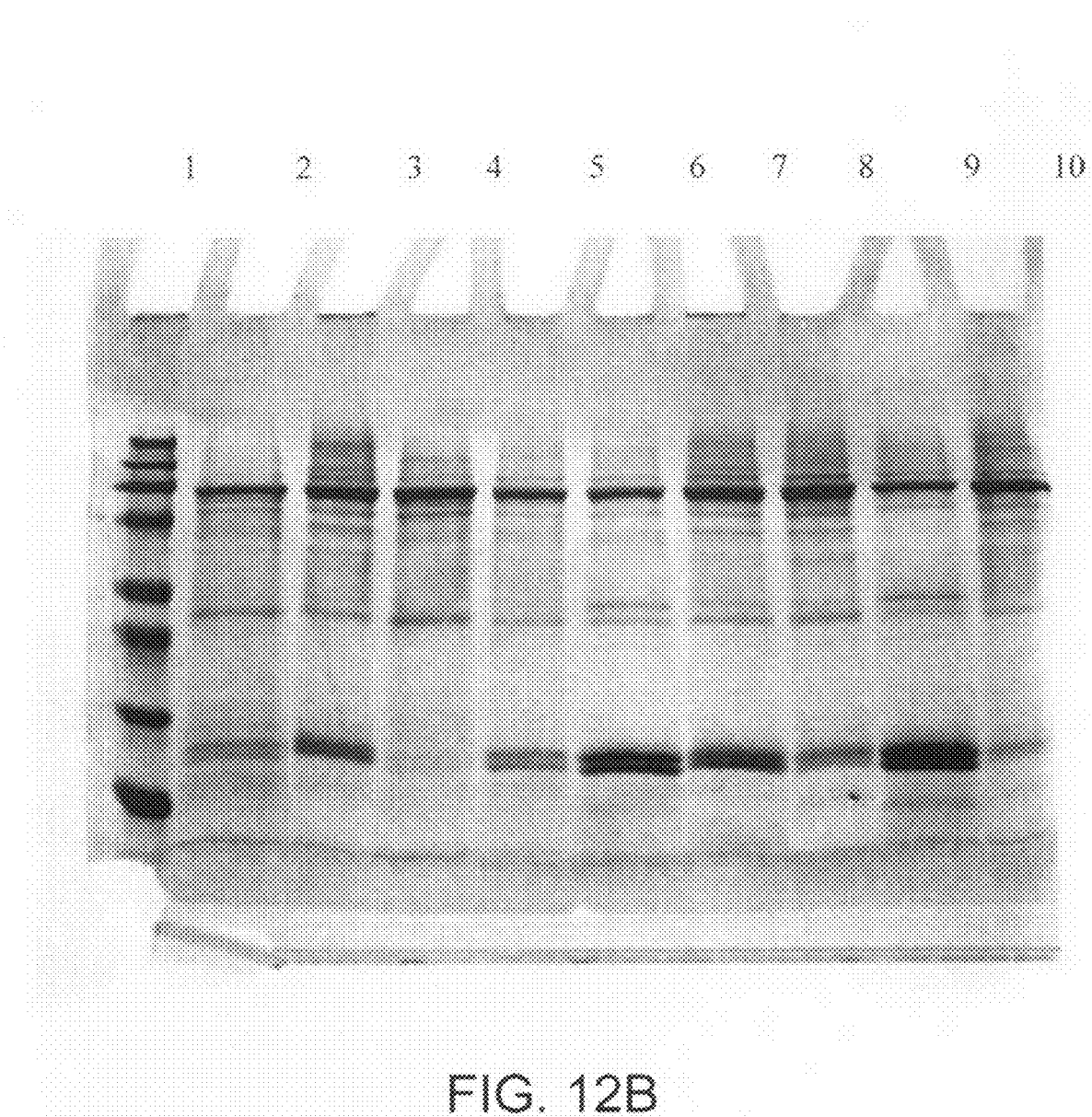

The purified antisera were screened against the peptides used to raise the antibodies using ELISA and Western Blot assays as described in Example 1. Briefly, rabbits were inoculated with each of the peptides set forth as SEQ ID NOs. 12-23, and the rabbit antisera were assayed, using the peptides as detection agents. The Western Blot results at a dilutions of 1:250 are shown in FIGS. 12a-b; in both Figures, Lane 1 is a molecular weight marker and Lane 10 is a commercial anti-MAPK antibody obtained from Cell Signaling Technologies used as a control. In FIG. 12a, Lane 2 shows the antibody immunoreactive with SEQ ID NO. 12; Lane 3 shows the antibody immunoreactive with SEQ ID NO. 13; Lane 4 shows the antibody immunoreactive with SEQ ID NO. 14; Lane 5 shows the antibody immunoreactive with SEQ ID NO. 15; Lane 6 shows the antibody immunoreactive with SEQ ID NO. 16; Lane 7 shows the antibody immunoreactive with SEQ ID NO. 17; Lane 8 shows the antibody immunoreactive with SEQ ID NO. 18; and Lane 9 shows the antibody immunoreactive with SEQ ID NO. 19. In FIG. 12b, Lane 2 shows the antibody immunoreactive with SEQ ID NO. 20; Lane 3 shows the antibody immunoreactive with SEQ ID NO. 21; Lane 4 shows the antibody immunoreactive with SEQ ID NO. 22; Lane 5 shows the antibody immunoreactive with SEQ ID NO. 23; Lane 6 shows the antibody immunoreactive with SEQ ID NO. 17; Lane 7 shows the antibody immunoreactive with SEQ ID NO. 18; Lane 8 shows the antibody immunoreactive with SEQ ID NO. 15; and Lane 9 shows the antibody immunoreactive with SEQ ID NO. 19.

Figure 11A:
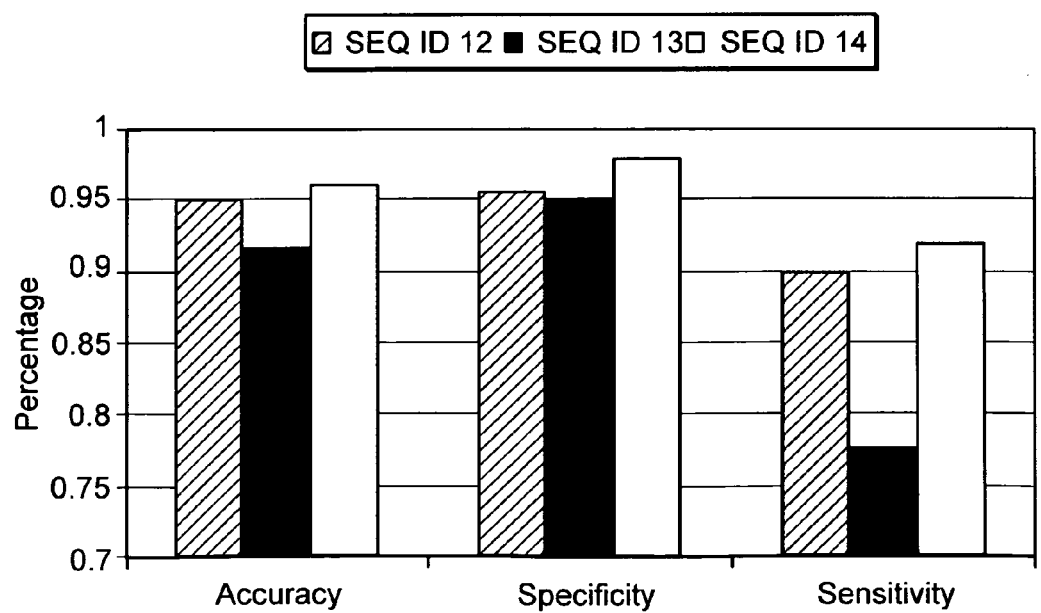
FIG. 11a shows the results for antibodies against SEQ ID NOs. 12, 13 and 14 at dilutions of 1:250.
Figure 11B:
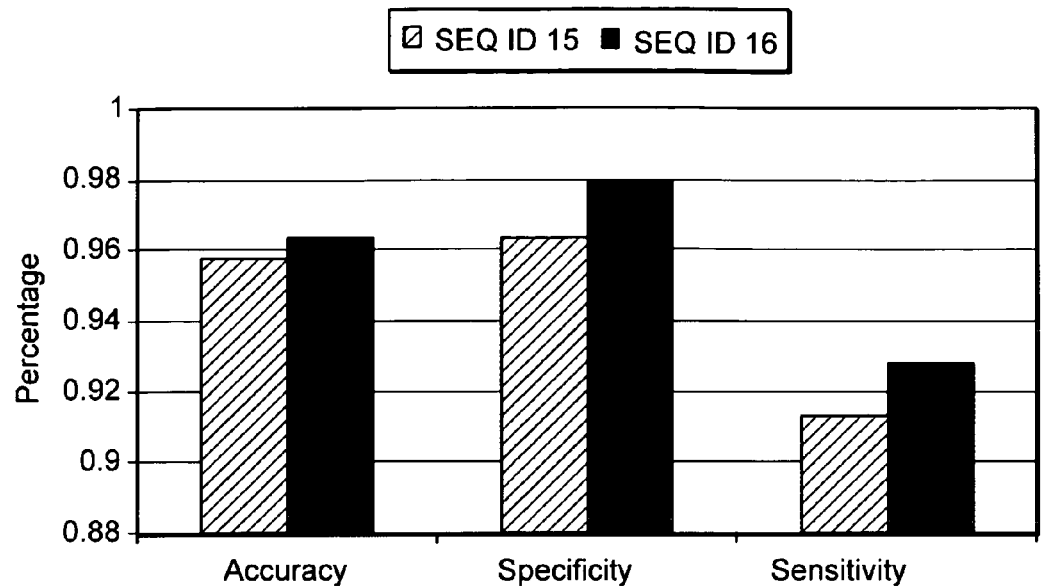
FIG. 11b shows the results for the antibodies against SEQ ID NOs. 15 and 16 at dilutions of 1:250.
Figure 11C:
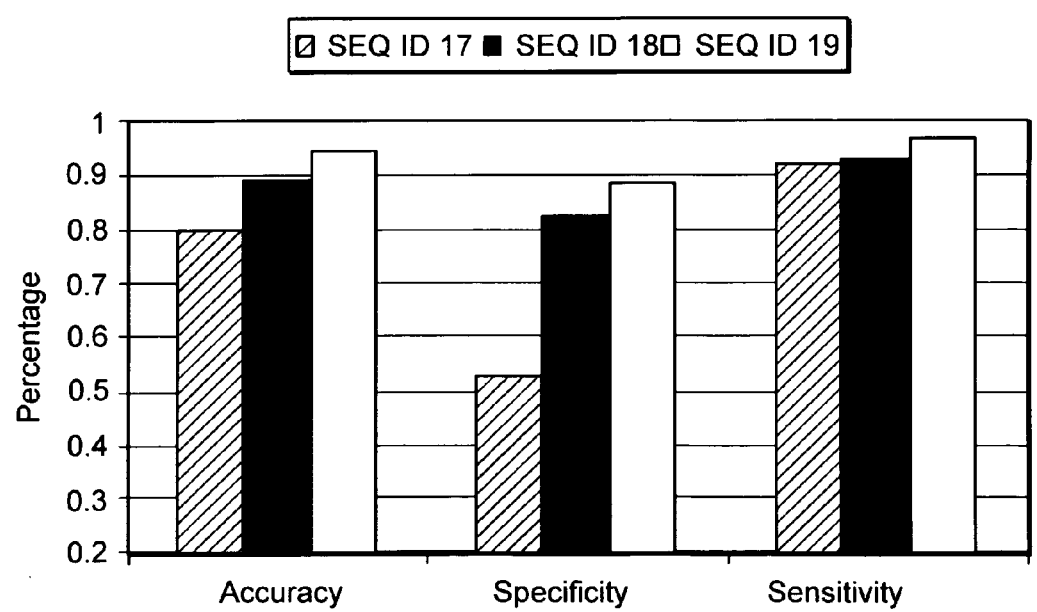
FIG. 11c shows the results for antibodies against SEQ ID NOs. 17, 18 and 19 at a dilution of 1:250.

The results of the ELISA assays for the antisera are shown schematically in FIGS. 11a-c. ELISA assays were performed using the following BSA-conjugated peptides (one assay per peptide) at dilutions of 1:250. The accuracy, specificity and sensitivity of the antibodies were measured using standard MS techniques. FIG. 11a is a graph showing the results for the antibodies against the peptides of SEQ ID. NOs. 12, 13 and 14; FIG. 11b shows the results for the antibodies against SEQ ID NOs. 15 and 16; and FIG. 11c shows the results for antibodies against SEQ ID NOs. 17, 18 and 19. The ELISA results for SEQ ID NOs. 20-23, not represented graphically, showed positive (>0) accuracy, specificity and sensitivity. The ELISA assay results showed that the antibodies against SEQ ID NOs. 12-23 all showed positive accuracy, specificity and sensitivity.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated polyclonal antibody specifically reactive with a kinase peptide consisting of a sequence selected from the group consisting of SEQ ID NOs. 8-13 and 16-23.

2. An isolated polyclonal antibody obtained by a method comprising the steps of:

a) contacting a mammal with at least one kinase peptide consisting of a sequence selected from the group consisting of SEQ ID NOs. 8-13 and 16-23; and b) collecting antiserum containing the polyclonal antibody from the mammal.

* * * * *

SEQUENCE LISTING

<160> NUMBER OF SEQ ID NOS: 23

<210> SEQ ID NO 1
<211> LENGTH: 14
<212> TYPE: PRT
<213> ORGANISM: Artificial
<220> FEATURE:
<223> OTHER INFORMATION: Artificial Receptor Tyrosine Kinase Peptide 1

<400> SEQUENCE: 1

Tyr Val His His Arg Asp Leu Ala Ala Ala Arg Asn Ile Leu
1               5                   10

<210> SEQ ID NO 2
<211> LENGTH: 14
<212> TYPE: PRT
<213> ORGANISM: Artificial
<220> FEATURE:
<223> OTHER INFORMATION: Artificial Receptor Tyrosine Kinase Peptide 2

<400> SEQUENCE: 2

Cys Ile His Arg Arg Asp Leu Ala Ala Arg Asn Asn Val Leu
1               5                   10

<210> SEQ ID NO 3
<211> LENGTH: 14
<212> TYPE: PRT
<213> ORGANISM: Artificial
<220> FEATURE:
<223> OTHER INFORMATION: Artificial Receptor Tyrosine Kinase Peptide 3

<400> SEQUENCE: 3

Phe Val His Arg Asp Leu Ala Ala Ala Arg Asn Asn Cys Met
1               5                   10

<210> SEQ ID NO 4
<211> LENGTH: 14
<212> TYPE: PRT
<213> ORGANISM: Artificial
<220> FEATURE:
<223> OTHER INFORMATION: Artificial Receptor Tyrosine Kinase Peptide 4

<400> SEQUENCE: 4

Leu Val His Arg Asp Asp Leu Leu Ala Ala Arg Asn Val Leu
1               5                   10

<210> SEQ ID NO 5
<211> LENGTH: 14
<212> TYPE: PRT
<213> ORGANISM: Artificial
<220> FEATURE:
<223> OTHER INFORMATION: Artificial Receptor Tyrosine Kinase Peptide 5

<400> SEQUENCE: 5

Phe Ile His His Arg Asp Ile Ala Ala Ala Arg Asn Cys Leu
1               5                   10

<210> SEQ ID NO 6
<211> LENGTH: 14
<212> TYPE: PRT
<213> ORGANISM: Artificial
<220> FEATURE:
<223> OTHER INFORMATION: Artificial Receptor Tyrosine Kinase Peptide 6

<400> SEQUENCE: 6

```
Phe Val His Arg Asp Asp Leu Ala Thr Arg Asn Cys Cys Leu
1               5                   10
```

```
<210> SEQ ID NO 7
<211> LENGTH: 10
<212> TYPE: PRT
<213> ORGANISM: Artificial
<220> FEATURE:
<223> OTHER INFORMATION: Artificial MAPKAP Kinase Peptide 1

<400> SEQUENCE: 7

Lys Lys Leu Asn Arg Thr Leu Ser Val Ala
1               5                   10
```

```
<210> SEQ ID NO 8
<211> LENGTH: 15
<212> TYPE: PRT
<213> ORGANISM: Artificial
<220> FEATURE:
<223> OTHER INFORMATION: Artificial MAPKAP Kinase Peptide 2

<400> SEQUENCE: 8

Cys Glu Gln Ile Lys Ile Lys Lys Ile Glu Asp Ala Ser Asn Pro
1               5                   10                  15
```

```
<210> SEQ ID NO 9
<211> LENGTH: 16
<212> TYPE: PRT
<213> ORGANISM: Artificial
<220> FEATURE:
<223> OTHER INFORMATION: Artificial MAPKAP Kinase Peptide 3

<400> SEQUENCE: 9

Lys Gln Ala Gly Ser Ser Ser Ala Ser Gln Gly Cys Asn Asn Gln Gly
1               5                   10                  15
```

```
<210> SEQ ID NO 10
<211> LENGTH: 10
<212> TYPE: PRT
<213> ORGANISM: Artificial
<220> FEATURE:
<223> OTHER INFORMATION: Artificial MAPKAP Kinase Peptide 4

<400> SEQUENCE: 10

Cys Ser His Asn Ser Leu Thr Pro Thr Pro
1               5                   10
```

```
<210> SEQ ID NO 11
<211> LENGTH: 15
<212> TYPE: PRT
<213> ORGANISM: Artificial
<220> FEATURE:
<223> OTHER INFORMATION: Artificial MAPKAP Kinase Peptide 5

<400> SEQUENCE: 11

Cys Asn Ser Ser Lys Pro Thr Pro Gln Leu Lys Pro Ile Glu Ser
1               5                   10                  15
```

```
<210> SEQ ID NO 12
<211> LENGTH: 13
<212> TYPE: PRT
<213> ORGANISM: Artificial
<220> FEATURE:
<223> OTHER INFORMATION: Artificial Phosphoinositide 3 Peptide 1

<400> SEQUENCE: 12

Cys Thr Glu Asp Arg Ile Gln His Ala Leu Glu Arg Arg
```

```
1               5                   10
```

<210> SEQ ID NO 13
<211> LENGTH: 14
<212> TYPE: PRT
<213> ORGANISM: Artificial
<220> FEATURE:
<223> OTHER INFORMATION: Artificial Phosphoinositide 3 Peptide 2

<400> SEQUENCE: 13

```
Cys Tyr Lys Pro Glu Lys Ser Asp Leu Leu Ser Ser Pro Pro
1               5                   10
```

<210> SEQ ID NO 14
<211> LENGTH: 10
<212> TYPE: PRT
<213> ORGANISM: Artificial
<220> FEATURE:
<223> OTHER INFORMATION: Artificial Phosphoinositide 3 Peptide 3

<400> SEQUENCE: 14

```
Lys Gly Leu His Glu Phe Asp Ser Leu Lys
1               5                   10
```

<210> SEQ ID NO 15
<211> LENGTH: 10
<212> TYPE: PRT
<213> ORGANISM: Artificial
<220> FEATURE:
<223> OTHER INFORMATION: Artificial Phosphoinositide 3 Peptide 4

<400> SEQUENCE: 15

```
Asn Glu Pro Leu Glu Phe Asp Ile Asn Ile
1               5                   10
```

<210> SEQ ID NO 16
<211> LENGTH: 10
<212> TYPE: PRT
<213> ORGANISM: Artificial
<220> FEATURE:
<223> OTHER INFORMATION: Artificial Phosphoinositide 3 Peptide 5

<400> SEQUENCE: 16

```
Leu Asn Ser Leu Ile Lys Leu Asn Ala Val
1               5                   10
```

<210> SEQ ID NO 17
<211> LENGTH: 10
<212> TYPE: PRT
<213> ORGANISM: Artificial
<220> FEATURE:
<223> OTHER INFORMATION: Artificial Phosphoinositide 3 Peptide 6

<400> SEQUENCE: 17

```
Glu Val Val Ser Thr Ser Glu Thr Ile Ala
1               5                   10
```

<210> SEQ ID NO 18
<211> LENGTH: 10
<212> TYPE: PRT
<213> ORGANISM: Artificial
<220> FEATURE:
<223> OTHER INFORMATION: Artificial Phosphoinositide 3 Peptide 7

<400> SEQUENCE: 18

```
Lys Gln Lys Phe Asp Glu Ala Leu Arg Glu
1               5                   10
```

```
<210> SEQ ID NO 19
<211> LENGTH: 10
<212> TYPE: PRT
<213> ORGANISM: Artificial
<220> FEATURE:
<223> OTHER INFORMATION: Artificial Phosphoinositide 3 Peptide 8

<400> SEQUENCE: 19

Lys Lys Gly Leu Glu Cys Ser Thr Leu Tyr
1               5                   10

<210> SEQ ID NO 20
<211> LENGTH: 10
<212> TYPE: PRT
<213> ORGANISM: Artificial
<220> FEATURE:
<223> OTHER INFORMATION: Artificial Phosphoinositide 3 Peptide 9

<400> SEQUENCE: 20

Ala Glu Trp Tyr Trp Gly Asp Ile Ser Arg
1               5                   10

<210> SEQ ID NO 21
<211> LENGTH: 10
<212> TYPE: PRT
<213> ORGANISM: Artificial
<220> FEATURE:
<223> OTHER INFORMATION: Artificial Phosphoinositide 3 Peptide 10

<400> SEQUENCE: 21

Asp Val Lys Leu Leu Tyr Pro Val Ser Lys
1               5                   10

<210> SEQ ID NO 22
<211> LENGTH: 10
<212> TYPE: PRT
<213> ORGANISM: Artificial
<220> FEATURE:
<223> OTHER INFORMATION: Artificial Phosphoinositide 3 Peptide 11

<400> SEQUENCE: 22

Ile Gln Arg Ile Met His Asn Tyr Asp Lys
1               5                   10

<210> SEQ ID NO 23
<211> LENGTH: 10
<212> TYPE: PRT
<213> ORGANISM: Artificial
<220> FEATURE:
<223> OTHER INFORMATION: Artificial Phosphoinositide 3 Peptide 12

<400> SEQUENCE: 23

Glu Asp Asp Glu Asp Leu Pro His His Asp
1               5                   10
```